United States Patent
Williams et al.

(10) Patent No.: US 10,996,208 B2
(45) Date of Patent: May 4, 2021

(54) ABALOPARATIDE FORMULATIONS AND METHODS OF TESTING, STORING, MODIFYING, AND USING SAME

(71) Applicant: Radius Health, Inc., Waltham, MA (US)

(72) Inventors: Greg Williams, Parsippany, NJ (US); Naveen Palwai, Parsippany, NJ (US); David Hanley, Parsippany, NJ (US)

(73) Assignee: Radius Health, Inc., Waltham, MA (US)

( * ) Notice: Subject to any disclaimer, the term of this patent is extended or adjusted under 35 U.S.C. 154(b) by 0 days.

(21) Appl. No.: 16/553,889

(22) Filed: Aug. 28, 2019

(65) Prior Publication Data

US 2020/0057041 A1 Feb. 20, 2020

Related U.S. Application Data

(63) Continuation of application No. 16/140,379, filed on Sep. 24, 2018, now abandoned, which is a continuation of application No. 15/967,504, filed on Apr. 30, 2018, now abandoned.

(60) Provisional application No. 62/492,022, filed on Apr. 28, 2017.

(51) Int. Cl.
*G01N 33/15* (2006.01)
*A61K 38/29* (2006.01)

(52) U.S. Cl.
CPC ............ *G01N 33/15* (2013.01); *A61K 38/29* (2013.01)

(58) Field of Classification Search
CPC ........ A61K 38/29; G01N 30/02; G01N 33/15; G01N 2030/027; G01N 30/34
See application file for complete search history.

(56) References Cited

U.S. PATENT DOCUMENTS

| | | | | |
|---|---|---|---|---|
| 6,770,623 B1 * | 8/2004 | Chang | ............... | A61K 9/0019 514/11.8 |
| 10,568,937 B2 * | 2/2020 | Hattersley | ............ | A61K 9/0021 |
| 2008/0287650 A1 * | 11/2008 | Tovi | ................. | C07K 1/20 530/317 |
| 2009/0105201 A1 * | 4/2009 | Blizzard | ............... | A61K 47/36 514/174 |
| 2014/0378382 A1 | 12/2014 | Gellman et al. | | |
| 2019/0091138 A1 * | 3/2019 | Hattersley | ............... | A61P 43/00 |
| 2020/0164045 A1 * | 5/2020 | Hattersley | .............. | A61K 38/29 |

FOREIGN PATENT DOCUMENTS

| | | | | |
|---|---|---|---|---|
| CN | 106146648 | * | 11/2016 | ............ C07K 14/635 |
| WO | WO2011139838 | * | 11/2011 | ............... A61K 9/08 |

OTHER PUBLICATIONS

CN106146648 Machine translation Chinese to English obtained from patents.google.com. 13 pages. (Year: 2016).*
Schellinger et al.Solubility of Buffers in Aqueous-Organic Eluents for Reversed-Phase Liquid Chromatography. LCGC North America, vol. 22, No. 6, pp. 544-548. (Year: 2004).*
ACE. A Guide To HPLC and LC-MS Buffer Selection, accessed online at https://www.hplc.eu/Downloads/ACE_Guide_BufferSelection.pdf on Apr. 23, 2019, 20 pages. (Year: 2019).*
Chambers et al. High sensitivity LC-MS/MS method for direct quantification of human parathyroid 1-34 (teriparatide) in human plasma. Journal of Chromatography B, No. 938, pp. 96-104 (Year: 2013).*

* cited by examiner

*Primary Examiner* — Marcela M Cordero Garcia
(74) *Attorney, Agent, or Firm* — Womble Bond Dickinson (US) LLP; Danielle L. Herritt

(57) ABSTRACT

Provided herein are newly discovered methods of analyzing abaloparatide samples for abaloparatide isomers. Additionally, methods of storing and treating with abaloparatide in view of the newly discovered abaloparatide isomers are described.

15 Claims, 50 Drawing Sheets

ABALOPARATIDE FORMULATIONS AND METHODS OF TESTING, STORING, MODIFYING, AND USING SAME

PRIORITY CLAIM

This application is a continuation of U.S. application Ser. No. 16/140,379, filed Sep. 24, 2018, which is a continuation of U.S. application Ser. No. 15/967,504, filed Apr. 30, 2018, which claims the benefit of U.S. Provisional Application No. 62/492,022, filed Apr. 28, 2017, the entire contents of each of which are incorporated herein by reference in their entirety, including drawings.

BACKGROUND

Conventionally, osteoporosis is treated by administration of antiresorptive agents to suppress bone resorption. The most common of these treatments is oral or intravenous administration of bisphosphonates. However, an undesirable side effect of bisphosphonate administration is reduced bone formation (MacLean 2008). This has led to the evaluation of anabolic agents as an alternative to antiresorptives.

Parathyroid hormone (PTH) is an anabolic agent that enhances osteoblastic bone formation. Teriparatide (Forteo®), a recombinant form of the N-terminal 34 residues of PTH (PTH-1-34), is currently the only anabolic agent approved for treatment of osteoporosis. Teriparatide acts by a mechanism that involves stimulating new bone formation (along with resorption) and reconstituting internal bone microarchitecture (Recker 2009; Dempster 2012; Ma 2011). Another anabolic agent, abaloparatide, is currently in late-stage clinical trials for treatment of osteoporosis. Abaloparatide is an analog of a secretory form of parathyroid hormone-related protein (PTHrP; UniProt Accession No. P12272). PTHrP and its other secretory forms (e.g., PTHrP (1-36), PTHrP(38-94), and osteostatin) and analogs thereof have also been investigated as potential treatments for osteoporosis in recent years. PTHrP and PTH share homology at their N-terminal ends, and both bind to the same G-protein coupled receptor, PTH receptor type-I (PTH1R). Despite this common receptor, PTH primarily acts as an endocrine regulator of calcium homeostasis, whereas PTHrP plays a fundamental paracrine role in the mediation of endochondral bone development (Kronenberg 2006). The differential effects of these proteins may be related not only to differential tissue expression, but also to distinct receptor binding properties (Pioszak 2009; Okazaki 2008; Dean 2008).

SUMMARY

As disclosed herein, improvements to the analytical procedures for evaluating abaloparatide formulation, including active pharmaceutical ingredient (API) and formulated drug product, have been developed. These improved procedures have resulted in the identification of previously unknown abaloparatide-derived or -related degradants and/or impurities (hereinafter collectively referred to as "related peptides" or "abaloparatide related peptides"): beta-Asp10, cyclo-Asp10, cyclo-Asp17, abaloparatide truncated peptide (3-34) ("ATP(3-34)"), and abaloparatide truncated peptide (4-34) ("ATP(4-34)"). The experimental results provided herein describe the identification, peak isolation, and characterization of these abaloparatide related peptides. Based on these findings, there is a need for methods of detecting the presence and/or measuring the actual or relative amount of these abaloparatide related peptides in abaloparatide formulations, formulating and storing abaloparatide in a manner that monitors and/or controls for these related peptides, and administering abaloparatide formulations in a manner that takes into account the actual or predicted presence and/or the actual or relative amount of the related peptides (as well as abaloparatide itself). The present disclosure provides each of these methods, as well as abaloparatide formulations comprising abaloparatide plus one or more of the related peptides, and the use of these formulations in the treatment of various conditions including, for example, osteoporosis, e.g., post-menopausal osteoporosis, glucocorticoid-induced osteoporosis, or male osteoporosis, osteoarthritis, or bone fracture healing.

Provided herein in certain embodiments are methods of detecting and quantifying the presence of one or more of abaloparatide, beta-Asp10, cyclo-Asp10, cyclo-Asp17, ATP (3-34), and ATP(4-34) in an abaloparatide formulation, including abaloparatide API or formulated abaloparatide drug product. In certain embodiments, these methods further comprise measuring the actual or relative amount (i.e., the amount as a percentage of total abaloparatide) of these peptides in an abaloparatide formulation at a given time. In certain embodiments the abaloparatide formulation is an aqueous abaloparatide formulation, and detection/measurement takes place immediately after the formulation is constituted, i.e., after API is constituted into an aqueous formulation suitable for drug delivery (t=0 of the formulated drug). In other embodiments, detection/measurement takes place after the aqueous abaloparatide formulation has been stored for one or more defined periods of time at one or more defined temperatures. In certain embodiments, the detection and measurement methods provided herein may be used to evaluate the degradation of an abaloparatide formulation and/or the levels of impurities, to determine or predict its total storage life or remaining storage life, or to evaluate storage conditions, methods, or timeframe conducive to use. In certain embodiments, the detection and measurement methods may also be used to determine the suitability of an abaloparatide formulation for administration to a subject or a patient population, to predict the therapeutic efficacy of an abaloparatide formulation, or to calculate the appropriate dosage of an abaloparatide formulation. In certain embodiments, the detection and measurement methods and the compositions provided herein may be incorporated into a method of treating an abaloparatide-addressable condition in a subject in need thereof, for example a method of treating osteoporosis, e.g., postmenopausal osteoporosis, glucocorticoid-induced osteoporosis, or male osteoporosis, osteoarthritis, or bone fractures.

Provided herein in certain embodiments are methods of analyzing an aqueous formulated abaloparatide drug product, including quantitating the presence of one or more of beta-Asp10, cyclo-Asp10, cyclo-Asp17, ATP(3-34), and ATP(4-34). In certain embodiments, these methods are used to evaluate storage conditions, and to determine whether the formulation is suitable for therapeutic administration, for example by determining whether the actual or relative amount of the peptide impurities/degradants are at or below a predetermined threshold value. In certain embodiments, the methods of analyzing and storing abaloparatide provided herein may be incorporated into a method of treating a condition in a subject in need thereof, for example a method of treating osteoporosis, e.g., postmenopausal osteoporosis, glucocorticoid-induced osteoporosis, or male osteoporosis, osteoarthritis, or bone fractures.

Provided herein in certain embodiments are methods of storing an abaloparatide formulation, including abaloparatide API and formulated abaloparatide drug product, in a manner that limits the amount of abaloparatide related peptides to at or below a predetermined threshold level (for a given time and/or conditions), as well as the therapeutic use of formulations stored according to these methods. In certain embodiments, these methods comprise storing the abaloparatide formulation for a specific period of time and/or at specific temperature. In certain embodiments, these methods comprise storing abaloparatide API and releasing API for further processing. In certain embodiments, the storage methods provided herein may be incorporated into a method of treating a condition in a subject in need thereof, for example a method of treating osteoporosis, e.g., post-menopausal osteoporosis, glucocorticoid-induced osteoporosis, or male osteoporosis, treating osteoarthritis, and/or accelerating the rate or improving the outcome of bone fracture healing. For example, in certain embodiments, the formulation may be administered to a subject for the first time at the end of the first period storage period, and in certain embodiments the formulation may be administered for a second time and any subsequent times over the course of the second storage period. In certain of these embodiments, the formulation is stored in a multi-injection pen, wherein the pen is used to inject a first dosage at the end of the first period and the beginning of the second period, and then to inject subsequent dosages over the course of the second period according to a particular dosage and/or schedule. In certain embodiments, an abaloparatide formulation stored in accordance with the methods provided herein may be subject to one or more of the methods of analyzing for beta-Asp10, cyclo-Asp10, cyclo-Asp17, ATP(3-34) and ATP(4-34) in an abaloparatide containing sample provided herein at one or more points over the course of the storage period. For example, the formulation may be subjected to a method of detecting and/or measuring the actual or relative amount of beta-Asp10, cyclo-Asp10, cyclo-Asp17, ATP(3-34) and ATP(4-34) in order to assess stability and/or suitability for administration. These methods may be performed at one or more predetermined intervals, at randomly selected intervals, or immediately prior to the first and/or any subsequent administrations. In certain of these embodiments, the stored formulation is only administered if the actual or relative amount of beta-Asp10, cyclo-Asp10, cyclo-Asp17, ATP(3-34) and ATP(4-34) is at or below a predetermined threshold value.

In certain embodiments, the detection, measurement, removal, and purification methods provided herein comprise subjecting an abaloparatide formulation, e.g., a sample or lot, to high performance liquid chromatography (HPLC) and/or ultra-high performance liquid chromatography (UPLC). In certain embodiments, the UPLC utilizes a column containing average mean particle diameters of less than 3.0 microns, or less than 2.5 microns, or less than 2.0 microns.

In certain embodiments, the HPLC and/or UPLC systems used in the methods provided herein utilize a buffer, for example a phosphate buffer, in the mobile phase. In certain of these embodiments, the phosphate buffer may be supplied as its ammonium phosphate salt. Phosphate salts with differing cationic counterions may be used (e.g., Na+, K+, and others known to those of ordinary skill in the art). In certain embodiments, a different ionic buffer (e.g., sulfonate) can be added to the HPLC/UPLC eluent to increase resolution between peaks, for example, the peaks from abaloparatide, beta-Asp10, cyclo-Asp10, cyclo-Asp17, ATP(3-34), and ATP(4-34). In certain embodiments, the buffer is used to establish and/or maintain the pH of the mobile phase. In certain embodiments, the pH of the buffer used in a binary eluent is about pH 6 to 10, 7 to 9, 7.5 to 8.5, or 7.6 to 8.0, for example about 7.8. In certain embodiments, the buffering agent is soluble in water at sufficient concentrations to retain the pH at the desired range in the aqueous solvent prior to mixing with another solvent. In other embodiments, the amount of buffering agent is sufficient to maintain the HPLC/UPLC solution phase (water plus any other solvent or combination of solvents) within the desired pH range, though generally it is more reliable to measure pH in the aqueous phase before mixing with a non-aqueous co-solvent. In certain embodiments, the desired pH range is established with a mono-basic phosphate buffer, for example $NaH_2PO_4$, $NH_4H_2PO_4$, or the like. In certain embodiments, a sulfonate buffer can be used to reach and buffer the desired pH range.

In certain embodiments, the HPLC and/or UPLC systems used in the methods provided herein utilize a predominately binary solvent system, and in certain of these embodiments the two solvents together comprise >90%, >95%, >98%, or >99% v/v of the mobile phase. In certain embodiments, one part of the mobile phase is aqueous and one part of the mobile phase is acetonitrile or methanol and in certain embodiments a third solvent (or combination of solvents) is used at a total of ≤10% v/v of the mobile phase. By way of non-limiting example, a predominately binary solvent system could contain 60% water, 30% acetonitrile, and up to 10% another solvent or combination of other solvents, e.g., 10% methanol, 5% methanol and 5% ethanol, or any other combination that meets the necessary guidelines. In certain embodiments, the above conditions are used in an UPLC system.

Provided herein in certain embodiments are formulations or API comprising abaloparatide plus one or more of beta-Asp10, cyclo-Asp10, cyclo-Asp17, ATP(3-34) and ATP(4-34). In other embodiments, abaloparatide API or aqueous formulations have been stored within specified periods of time under specific temperature conditions. In certain embodiments, the formulated drug products are aqueous and comprise between 1.8 mg/mL and 2.2 mg/mL of abaloparatide, or between 1.86 and 2.10 or between 1.90 and 2.10 or about 2.0 mg/mL. In certain embodiments, the formulation are pharmaceutical formulations comprising one or more pharmaceutically acceptable excipients in addition to the abaloparatide.

In certain embodiments, the abaloparatide API provided herein comprises ≤0.5% beta-Asp10, ≤0.5% cyclo-Asp10, ≤0.5% cyclo-Asp17 and where ATP(3-34) and ATP(4-34) are together ≤1.0% and wherein said API further comprises ≥97% of abaloparatide of the total peptide content in the API. In some embodiments, the API is stored at -20±2° C.

In some embodiments, an aqueous formulation of abaloparatide comprises ≤1.0% beta-Asp10, ≤0.5% cyclo-Asp10, ≤0.5% cyclo-Asp17, ≤0.5% ATP(3-34) and <0.5% ATP(4-34) and wherein said aqueous further comprises ≥97% of abaloparatide of the total peptide content in the aqueous abaloparatide formulation at t=0 (upon initial formulation of the API into an aqueous formulation).

In certain embodiments, the formulations provided herein are aqueous formulated drug products stored for 0-23 months or 0-35 months, at 2-8 °C., and about 0-1 month at room temperature, e.g., 20-25° C. or about 25±2° C., that comprise abaloparatide and beta-Asp10, and in certain of these embodiments beta-Asp10 represents ≤5% or between 0% to ≤5%, 0 to 4%, 0 to 3%, or 0.1% to 5%, or 0.5% to 4.5%, or 0.5% to 4.0%, or 0.1% to ≤5%, 0.5% to ≤5%, or 1.0% to ≤5% % of total peptide content in the formulation. In certain embodiments, the formulations provided herein are aqueous formulated drug products stored for 0-23 months or 0-35 months, at 2-8° C., and for about 0-1 month at room temperature, e.g., 20-25° C. or about 25±2° C. that also comprise cyclo-Asp10 and/or cyclo-Asp17 and/or ATP (3-34) and/or ATP(4-34), and in certain of these embodiments each of said cyclo-Asp10, cyclo-Asp17, ATP(3-34) and ATP(4-34) is present in an amount of ≤0.5% of peptide content in the formulation. In some embodiments, the abaloparatide content is ≥93% of the total of the peptide content in the sample. In some embodiments, a method of establishing suitability of an abaloparatide manufacturing process and drug product comprises formulating abaloparatide API into an aqueous vehicle, wherein said abaloparatide API is first analyzed and determined to contain ≤0.5% beta-Asp10, ≤0.5% cyclo-Asp10, ≤0.5% cyclo-Asp17 and where ATP(3-34) and ATP(4-34) are together ≤1.0% and wherein said API further comprises ≥97% of abaloparatide of the total peptide content in the API and further determining that the initially prepared aqueous abaloparatide containing formulation (t=0) comprises ≤1.0% beta-Asp10, ≤0.5% cyclo-Asp10, ≤0.5% cyclo-Asp17, ≤0.5% ATP(3-34) and ≤0.5% ATP(4-34) and wherein said aqueous further comprises ≥97% of abaloparatide of the total peptide content in the aqueous abaloparatide formulation and further embodiments, storing said aqueous abaloparatide formulation for 23 months and then storing at 25±2° C. for 1 month or 35 months and then storing at 25±2° C. for 1 month at 2-8° C. and then storing at 25±2° C. for 1 month and evaluating the drug product during and after said storage period and in certain of these embodiments each of said cyclo-Asp10, cyclo-Asp17, ATP (3-34) and ATP(4-34) is present in an amount of ≤0.5% of peptide content in the formulation and the abaloparatide content is ≥93% of the total of the peptide content in the sample.

In certain embodiments wherein a formulation provided herein is a formulated abaloparatide containing drug product, the formulation has a pH between 2-7, 3-6, 4-6, 4.5-5.5, or 4.7-5.5, and in certain of these embodiments the pH is about 5.1 or about 5.2. In certain embodiments, the formulation comprises a buffer, and in certain of these embodiments the buffer is an acetate buffer, for example acetic acid or sodium acetate, or a phosphate buffer, for example potassium phosphate. In certain embodiments, the buffer is in a concentration range sufficient to provide the desired level of buffer capacity, for example 0.1 mM to 60 mM, 0.5 to 50 mM, 1 to 10 mM, 4 to 8 mM, or about 6 mM.

In certain embodiments wherein a formulation provided herein is a formulated drug product, the formulation comprises an antimicrobial agent, for example a compound with a phenolic group such as chlorocresol or phenol, at a concentration sufficient to provide anti-microbial effect. In certain embodiments, the antimicrobial agent may be phenol at a concentration of ≤8.0 mg, for example ≤5.0 mg/mL or about 5.0 mg/mL. In certain embodiments, the antimicrobial agent further serves as an antioxidant preservative, increasing the integrity of abaloparatide in the formulation by reducing the rate of decomposition over the shelf-life of the formulation, for example over 23 months at 2 to 8° C. followed by 1 month at 20-25° C. or about 25±2° C., or over 35 months at 2 to 8° C. followed by 1 month at 20-25° C. or about 25±2° C. In certain embodiments, the antimicrobial agent may increase the integrity of abaloparatide in the formulation over longer time periods or wider temperature ranges. In certain embodiments, the antioxidant effect may be more measurably demonstrable over increased storage times, elevated temperatures, or other formulation variables.

Provided herein in certain embodiments are methods of treating a condition in a subject in need thereof, e.g., a method of treating osteoporosis such as postmenopausal osteoporosis, glucocorticoid-induced osteoporosis, or male osteoporosis, treating osteoarthritis, or accelerating the rate or improving the outcome of bone fracture healing, wherein said methods utilize one or more of the detection, measurement, removal, purification, or storage methods provided herein. For example, methods of treatment are provided that comprise measuring the actual or relative amount of abaloparatide related peptides in an abaloparatide formulation prior to administering the formulation to a subject, wherein the formulation is only administered to the subject if the actual or relative amount of abaloparatide related peptides are at or below a predetermined threshold value. In another example, methods of treatment are provided that utilize an abaloparatide formulation stored according to the storage methods provided herein, optionally wherein the abaloparatide formulation is subjected to one or more of the detection, measurement, removal, or purification methods provided herein prior to storage, after storage, and/or at one or more timepoints during storage, for example just before the first administration or a subsequent administration of the formulation. In certain embodiments, methods are provided for treating a patient with an abaloparatide formulation comprising administering a first dosage of abaloparatide formulation that has been stored for a first period of about 0-23 or about 0-35 months at about 2-8° C., then storing the remaining abaloparatide formulation at room temperature, e.g., 20-25° C., for a second period of about 30 days or 30 days. In certain embodiments, these methods may utilize a multi-injection pen, and the pen is stored at room temperature for about 30 days (or 30 days) after the first administration, with the subject receiving one injection per day over that period and in some embodiments the daily dosage of abaloparatide is 80 μg. In certain embodiments, the formulation is administered at approximately the same time each day, such that dosages are administered about 24 hours apart. In some embodiments the patient discards the multi-injection pen after 30 days from the first injection (after a total of up to 30 once daily injections).

Provided herein in certain embodiments are methods of treating a condition in a subject in need thereof, e.g., a method of treating osteoporosis such as post-menopausal osteoporosis, glucocorticoid-induced osteoporosis, or male osteoporosis, a method of treating osteoarthritis, or, and/or accelerating the rate or improving the outcome of bone fracture healing, using a formulation provided herein. In certain embodiments, these methods incorporate one or more of the detection, measurement, removal, purification, or storage methods provided herein. In certain embodiments, the abaloparatide formulation is administered once daily for about 30 days. In certain embodiments of the methods of treatment provided herein, the abaloparatide formulation is administered via subcutaneous injection, for example to periumbilicular region.

In general and unless stated otherwise, when percentages and percent ranges and percent limits are given for abaloparatide, impurities, degradants, the values are determined from HPLC and/or UPLC integration ratios where such HPLC and/or UPLC integration procedures are calibrated in accord with standard techniques known to one of ordinary skill in the art. A percentage of peptide impurities or degradants and/or abaloparatide are derived from the ratio of the particular impurity and/or degradant and/or abaloparatide divided by the total area of the total peptide content in the chromatogram (and multiplied by 100%), and the sum total of all peptide content from an abaloparatide-containing API or aqueous formulation should equal about 100%.

In certain embodiments of the methods of treatment provided herein, a multi-dose injection pen is used to administer the drug. In certain of these embodiments, the multi-dose injection pen is stored according to the methods of storage provided herein. In certain embodiments, the multi-dose injection pen initially contains enough formulated abaloparatide drug product to allow for about 30 days of once daily injections, for example at a daily dosage of about 80 µg abaloparatide. For example, the pen may initially contain 2.4 mg or more of abaloparatide. In certain embodiments, the multi-dose injection pen may contain about 1.2 mL of formulated abaloparatide drug product at a concentration of about 2.0 mg/mL. In other embodiments, the multi-injection pen may contain more than enough formulated abaloparatide drug product for 30 days of once daily injections. For example, the pen may initially contain about 3.12 mg abaloparatide. In certain embodiments, the pen may contain about 1.56 mL of formulated abaloparatide drug formulation at an abaloparatide concentration of about 1.8-2.2 mg/mL, 1.86-2.10, 1.90-2.10 or about 2 mg/mL. In certain of these embodiments wherein the pen contains excess abaloparatide formulation for 30 days of once daily injections, the pen may nonetheless be indicated for disposal at the end of 30 days at room temperature. In certain embodiments, the injection pen is disposed after 30 days at room temperature regardless of how many injections (up to 30) have been administered and in certain embodiments the disposed pen still contains some aqueous formulated abaloparatide.

BRIEF DESCRIPTION OF THE DRAWINGS

(FIG. 9A) Resolution standard solution. (FIG. 9B) Overlay spiked truncated peptides with unspiked abaloparatide sample. (FIG. 9C) Beta-Asp10 isomer peak (RDS-001-A01) resolved from abaloparatide in API abaloparatide reference standard.

(FIG. 10A) Formulated drug product batch analysis (BEJH09b) by Method 1. (FIG. 10B) Formulated drug product batch analysis (BEJH09b) by Method 3.

(FIG. 11A) Testing of API sample 8AK1 by Method 1. (FIG. 11B) Testing of API sample 8AK1 by Method 2.

(FIG. 12A) Truncated peptides by UPLC conditions related to Method 4: phosphate/C18. Partially resolved abaloparatide and ATP (3-34) and ATP (4-34). (FIG. 12U) Phosphate/C4—0.3 ml/min—8AG1.

(FIG. 13A) Method 1—Acid stress HCl 1N. (FIG. 13B): Method 2—Acid stress HCl 1N. (FIG. 13C) Method 1—Base stress NaOH 0.01N. (FIG. 13D) Method 2—Base stress NaOH 0.01N. (FIG. 13E) Method 1—Heat stress+80° C. (FIG. 13F) Method 2 —Heat stress+80° C. (FIG. 13G) Method 3 —Acid Stress HCl 1N. (FIG. 13H) Method 4 —Acid Stress HCl 1N. (FIG. 13I) Method 3 —Base Stress NaOH 0.01N. (FIG. 13J) Method 4 —Base Stress NaOH 0.01N. (FIG. 13K) Method 3 —Heat stress+80° C. (FIG. 13L) Method 4 —Heat stress+80° C.

DETAILED DESCRIPTION

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

Abbreviations

API: active pharmaceutical ingredient; DP: drug product; HPLC: high performance liquid chromatography; MS: mass spectroscopy; NLT: not less than; NMT: not more than; RRT: relative retention time; RT: room temperature; TFA: trifluoroacetic acid; and UPLC: ultra-high performance liquid chromatography.

Definitions

The term "abaloparatide" as used herein refers to [$Glu^{22,25}$, $Leu^{23,28,31}$ $Aib^{29}$, $Lys^{26,30}$]hPTHrP(1-34)NH$_2$) (Ala-Val-Ser-Glu-His-Gln-Leu-Leu-His-Asp-Lys-Gly-Lys-Ser-Ile-Gln-Asp-Leu-Arg-Arg-Arg-Glu-Leu-Leu-Glu-Lys- Leu-Leu-Aib-Lys-Leu-His-Thr-Ala, SEQ ID NO:1), a peptide analog of PTHrP(1-34). Each of the 34 amino acids in abaloparatide are alpha amino acids. Aib is 2-aminoisobutyric acid, also known as α-aminoisobutyric acid or dimethylglycine.

Figure 1A:
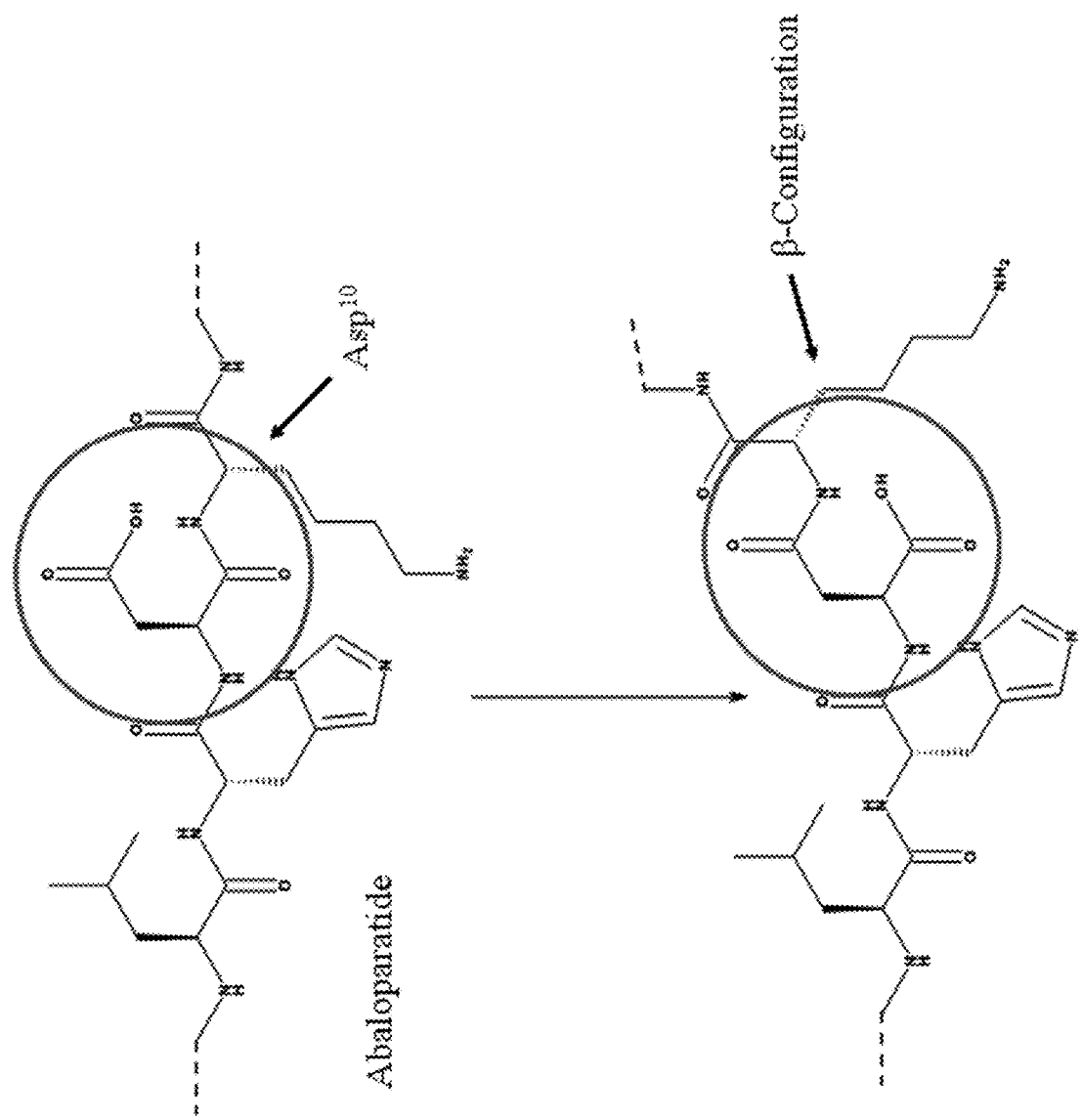
FIG. 1A: Rearrangement of Asp residue at position 10 of abaloparatide to generate beta-Asp10 abaloparatide.

The terms "beta-Asp-abaloparatide," "beta-Asp10," "beta isomer," and "(beta-Asp10) abaloparatide" as used herein refer to an isomer of abaloparatide in which the Asp at position 10 (Asp10) has been isomerized to beta Asp: [b-Asp$^{10}$, Glu$^{22,25}$, Leu$^{23,28,31}$, Aib$^{29}$, Lys$^{26,30}$]hPTHrP(1-34)NH2) (Ala-Val-Ser-Glu-His-Gln-Leu-Leu-His-b-Asp-Lys-Gly-Lys-Ser-Ile-Gln-Asp-Leu-Arg-Arg-Arg-Glu-Leu-Leu-Glu-Lys-Leu-Leu-Aib-Lys-Leu-His-Thr-Ala, SEQ ID NO:2). FIG. 1A shows a comparison of abaloparatide fragment (8-11) and (beta-Asp10) abaloparatide fragment (8-11).

Figure 1B:
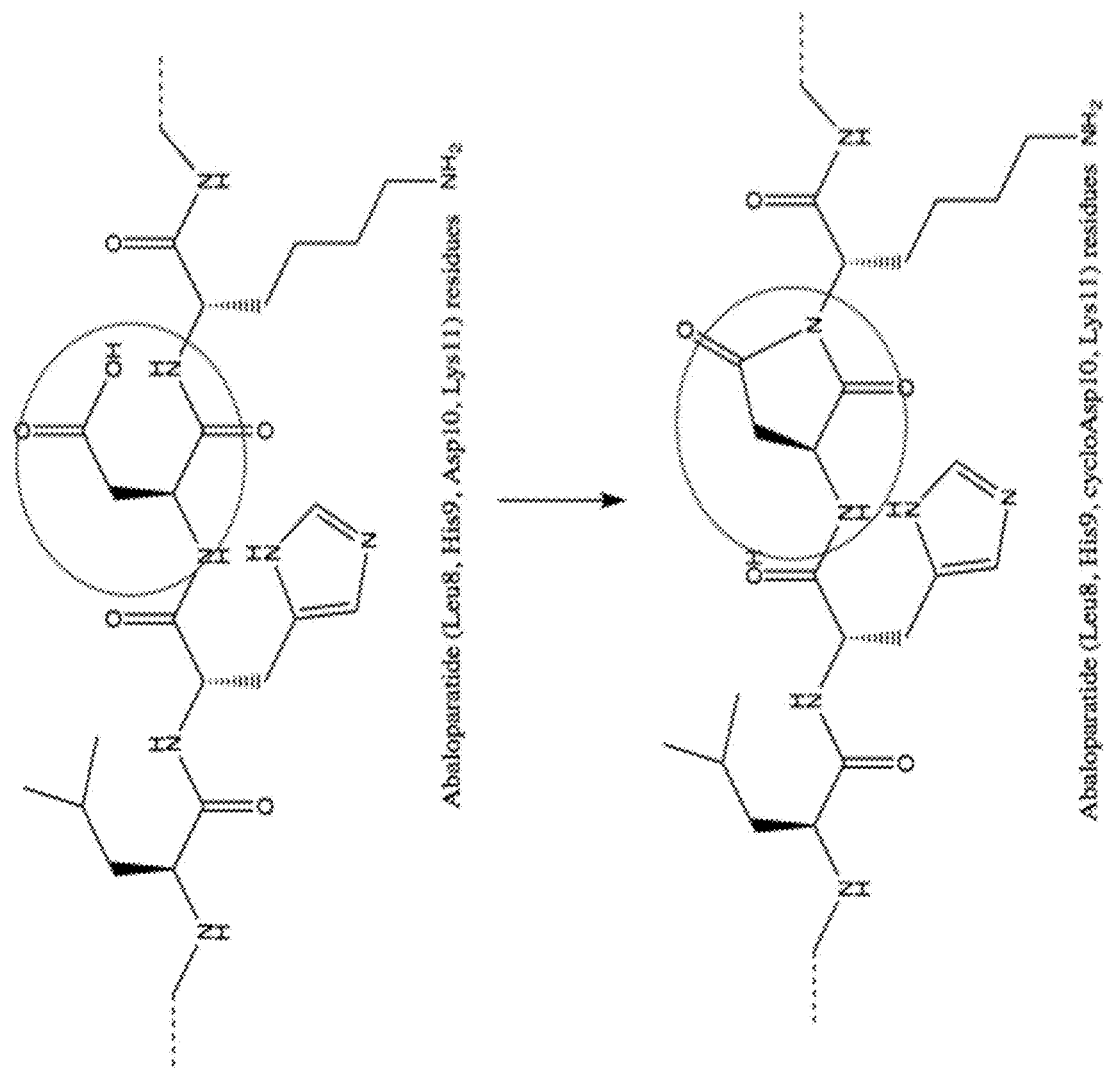
FIG. 1B: Rearrangement of Asp residue at position 10 of abaloparatide to generate cyclo-Asp10 abaloparatide.
Figure 1C:
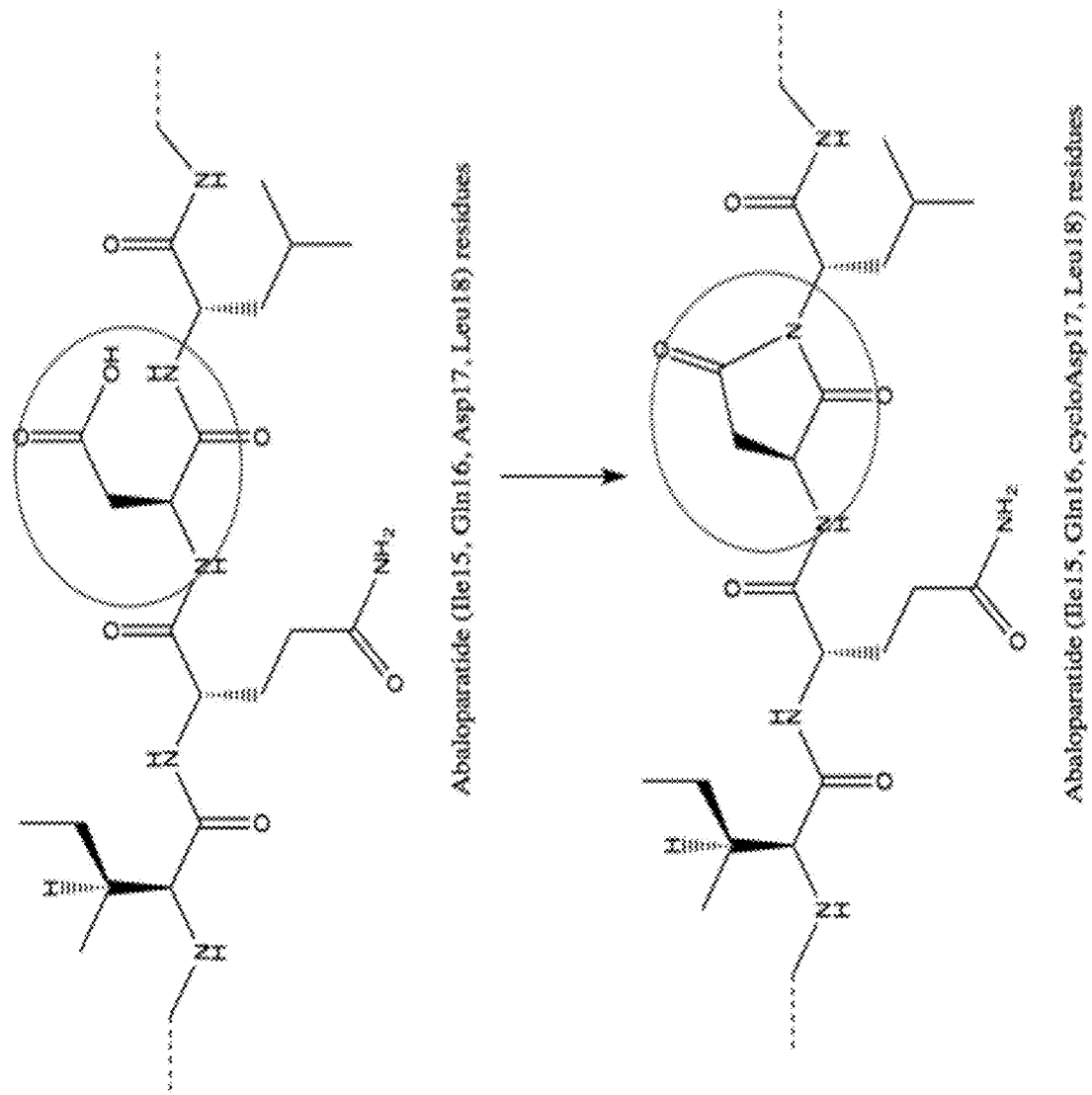
FIG. 1C: Rearrangement of Asp residue at position 17 of abaloparatide to generate cyclo-Asp17.

The terms "cyclo-Asp10" and "(cyclo-Asp10) abaloparatide" as used herein refer to an isomer of abaloparatide in which the Asp at position 10 (Asp10) has been cyclized to form an imide. The terms "cyclo-Asp17" and "(cyclo-Asp17) abaloparatide" as used herein refer to an isomer of abaloparatide in which the Asp at position 17 (Asp17) has been cyclized to form an imide. FIGS. 1B and 1C show comparisons of abaloparatide (8-11) with (cyclo-Asp10) abaloparatide (8-11), and abaloparatide (16-19) with (cyclo-Asp17) abaloparatide (16-19)), respectively.

The term "abaloparatide API" as used herein refers to an abaloparatide formulation that has undergone final manufacture and purification of the peptide, but has not yet been formulated in an aqueous vehicle suitable for drug delivery. In certain embodiments, the abaloparatide API contains only abaloparatide, or, i.e., there are no significant additional or added components.

The term "formulated abaloparatide drug product" as used herein refers to an abaloparatide formulation in which the abaloparatide API has been formulated in an aqueous vehicle suitable for drug delivery.

The term "abaloparatide formulation" as used herein refers to an API or formulated drug product comprising abaloparatide. Such a formulation may comprise one or more additional components, including both active (e.g., additional therapeutic agents) and inactive (e.g., excipients, buffers, etc.) components.

The term "about" as used herein with regard to a stated value means within 10% of the stated value.

The term "essentially" as used herein with regard to a stated value means within 5% of the stated value.

The terms "truncated abaloparatide (3-34)" and "truncated abaloparatide (4-34)" (abbreviated herein as "ATP(3-34)" and "ATP(4-34)," respectively) refer to abaloparatide sequences wherein the first two (i.e., Ala-Val) or three (i.e., Ala-Val-Ser) N-terminal amino acids, respectively, are missing.

Description

Abaloparatide is currently in clinical trials for the treatment of osteoporosis in postmenopausal women. Two different dosage forms are currently under development, a subcutaneous (SC) formulation (abaloparatide-SC) for self-injection via a multi-dose injector pen and a transdermal (TD) formulation (abaloparatide-TD) for delivery via a microneedle patch. For the abaloparatide-SC formulation, the recommended dosage is 80 µg once daily for a total continuous duration of 18 months.

As disclosed herein, it has been discovered that under certain conditions, abaloparatide can undergo an intramolecular rearrangement that results in formation of the beta-Asp10 isomer. Numerous batches of abaloparatide API, mixtures, and formulations had been evaluated previously using a variety of techniques, but none of those techniques had identified the presence of the (beta-Asp10) isomer. As discussed in detail in the Examples section below, the existence of the (beta-Asp10) isomer was discovered through application of new particular liquid chromatography separation and purification methods. Some of these new chromatography methods resulted in remarkably clean baseline or near-baseline separation between abaloparatide and the (beta-Asp10) isomer, as well as other abaloparatide-related impurities such as cyclo-Asp10, cyclo-Asp17, ATP (3-34), and ATP(4-34). The fortuitous identification and subsequent isolation and characterization of (beta-Asp10) isomer has allowed for the development of improved methods of storing, analyzing, controlling and administering abaloparatide.

Accordingly, provided herein in certain embodiments are (beta-Asp10) abaloparatide, as well as compositions, pharmaceutical formulations, and kits comprising (beta-Asp10) abaloparatide. In certain embodiments, compositions and pharmaceutical formulations comprising (beta-Asp10) abaloparatide and abaloparatide in predetermined and established ranges. In addition, provided herein are methods of analyzing a sample of abaloparatide for the presence of (beta-Asp10) abaloparatide. Also included are the use of (beta-Asp10) abaloparatide in analytic methods used for the detection of (beta-Asp10) abaloparatide in lots of abaloparatide API and/or aqueous formulated abaloparatide. Furthermore, (beta-Asp10) abaloparatide is provided as a composition per se, for example, a material sample comprising >50% by weight, >60%, >70%, >80%, >90%, >95% (beta-Asp10) abaloparatide. In certain embodiments of this invention, an abaloparatide (beta-Asp10) sample is provided wherein said sample comprises also abaloparatide wherein the sample is w/w (beta-Asp10) abaloparatide to abaloparatide >50% by weight, >60%, >70%, >80%, >90%, >95%, respectively. Compositions of (beta-Asp10) have utility for analytical determinations but also are active per se as an agonist on PTH receptors providing credible evidence of utility for use in the treatment of osteoporosis, as a standalone treatment or in combination with one or more other drugs. For example, also included are embodiments providing methods of treating osteoporosis comprising the administration of abaloparatide together with (beta-Asp10) abaloparatide in a predetermined range. Also included are embodiments wherein a method of treating osteoporosis is provided comprising a first step of analyzing a lot of abaloparatide for the presence of beta-Asp10 and if said lot has beta-10Asp in a concentration ≤5%, or between 0.01% and ≤5% then proceeding to administer 80 µG of abaloparatide to a subject in need thereof.

As described herein, it has been discovered that the ratio of abaloparatide to (beta-Asp10) isomer within an abaloparatide formulation can be affected by a number of factors. These factors include, but are not limited to: (1) purity of original abaloparatide manufacturing lot (i.e., the presence and amount of any beta-Asp10 isomer in the original abaloparatide lot); and (2) storage conditions, e.g., storage temperature of abaloparatide formulation(API, aqueous drug formulation), and storage time at particular temperatures.

Provided in certain embodiments of the disclosure are abaloparatide API samples comprising ≤0.5% (beta-Asp10) abaloparatide of the total peptide content. Provided in certain embodiments of the disclosure are abaloparatide API samples comprising ≤1.0% ATP(3-34) plus ATP(4-34) of the total peptide content. Provided in certain embodiments of the disclosure are abaloparatide API samples comprising ≤0.5% w/w (beta-Asp10) abaloparatide and <1% ATP(3-34) plus ATP(4-34) of the total peptide content. Provided in certain embodiments of the disclosure are abaloparatide API samples comprising ≤0.5% beta-Asp10, ≤0.5% cyclo-Asp10, ≤0.5% cyclo-Asp17 and where ATP(3-34) and ATP(4-34) are together ≤1.0% of the total peptide content and wherein said API further comprises ≥97% of abaloparatide of the total peptide content in the API. In some embodiments, the API is stored at −20±2° C.

Provided in certain embodiments of the disclosure are aqueous abaloparatide formulations comprising ≤1.0% w/w (beta-Asp10), ≤0.5% ATP(3-34), ≤0.5% ATP(4-34), ≤0.5% (cyclo-Asp10), and ≤0.5% (cycloAsp17) of the total peptide content, and an aqueous buffer having a pH of from 4.5-5.5, wherein said formulation has an abaloparatide concentration of between about 1.8 mg/mL and about 2.2 mg/mL, between about 1.86 and about 2.10 mg/mL, between about 1.90 mg/mL and about 2.10 mg/mL, or about 2.0 mg/mL.

Provided in certain embodiments of the disclosure are aqueous formulations of abaloparatide comprising ≤1.0% beta-Asp10, ≤0.5% cyclo-Asp10, ≤0.5% cyclo-Asp17, ≤0.5% ATP(3-34) and ≤0.5% ATP(4-34) of the total peptide content and wherein said aqueous further comprises ≥97% of abaloparatide of the total peptide content in the aqueous abaloparatide formulation at t=0 (upon initial formulation of the API into an aqueous formulation).

In certain embodiments, the aqueous abaloparatide formulations disclosed herein are stored for 0-23 months or 0-35 months, at 2-8 ° C., and about 0-1 month at room temperature, e.g., 20-25° C. or about 25±2° C., that comprise abaloparatide and beta-Asp10, and in certain of these embodiments beta-Asp10 represents ≤5% or between 0% to ≤5%, 0 to 4%, 0 to 3%, or 0.1% to 5%, or 0.5% to 4.5%, or 0.5% to 4.0%, or 0.1% to ≤5%, 0.5% to ≤5%, or 1.0% to ≤5% % of total peptide content in the formulation. In certain embodiments, the aqueous abaloparatide formulations disclosed herein are stored for 0-23 months or 0-35 months, at 2-8° C., and for about 0-1 month at room temperature, e.g., 20-25° C. or about 25±2° C. that also comprise cyclo-Asp10 and/or cyclo-Asp17 and/or ATP(3-34) and/or ATP(4-34), and in certain of these embodiments each of said cyclo-Asp10, cyclo-Asp17, ATP(3-34) and ATP(4-34) is present in an amount of ≤0.5% of peptide content in the formulation. In some embodiments, the abaloparatide content is ≥93% of the total of the peptide content in the aqueous abaloparatide formulations.

Provided in certain embodiments of the disclosure are abaloparatide aqueous formulations comprising abaloparatide and ≤0.5% w/w (beta-Asp10) abaloparatide and <1% ATP(3-34) plus ATP(4-34) of the total peptide content. In certain embodiments, the abaloparatide aqueous formulations has an abaloparatide concentration between about 1.8 and about 2.2 mg/mL. In certain embodiments, the abaloparatide aqueous formulations has a pH between about 2 to about 7, about 3 to about 6, about 4 to about 6, about 4.5 to about 5.5, about 4.7 to about 5.5, about 5.1, or about 5.2. In certain embodiments, the abaloparatide aqueous formulation comprises a buffer. Examples of the buffer include, without limitation, an acetate buffer comprising, e.g., acetic acid or sodium acetate; and a phosphate buffer comprising, e.g., potassium phosphate. In certain embodiments, the buffer is in a concentration range sufficient to provide the desired level of buffer capacity, for example about 0.1 mM to about 60 mM, about 0.5 mM to about 50 mM, about 1 to about 10 mM, about 4 to about 8 mM, or about 6 mM. The abaloparatide aqueous formulations may further comprise an antimicrobial agent (e.g., a compound with a phenolic group such as chlorocresol or phenol) at a concentration sufficient to provide anti-microbial effect. In certain embodiments, the antimicrobial agent may be phenol at a concentration of ≤8.0 mg, for example ≤5.0 mg/mL or about 5.0 mg/mL. In certain embodiments, the antimicrobial agent further serves as an antioxidant preservative, increasing the integrity of abaloparatide in the formulation by reducing the rate of decomposition over the shelf-life of the formulation, for example over 23 months at 2 to 8° C. followed by 1 month at 20-25° C. or about 25±2° C., or over 35 months at 2 to 8° C.) followed by 1 month at 20-25° C. or about 25±2° C. In certain embodiments, the antimicrobial agent may increase the integrity of abaloparatide in the formulation over longer time periods or wider temperature ranges. In certain embodiments, the antioxidant effect may be more measurably demonstrable over increased storage times, elevated temperatures, or other formulation variables Provided in some embodiments of this disclosure are methods of analyzing an abaloparatide API sample or an abaloparatide aqueous formulation disclosed herein comprising using a HPLC and/or UPLC. In certain embodiments, the analyzing method comprises using a mobile phase comprising an aqueous base (e.g., an aqueous buffer). The pH of the aqueous buffer may be about 6 to about 10, about 7 to about 9, about 7.5 to about 8.5, about 7.6 to about 8.0 or about 7.8. In certain embodiments, the pH of the aqueous buffer is at RT or about 25 ° C. The aqueous buffer may comprise phosphate, sulfonate, or combinations thereof. The aqueous buffer may comprise one or more cationic counterions such as $Na^+$, $K^+$, $NH_4^+$, and combinations thereof. In certain embodiments, the aqueous buffer is ammonium phosphate buffer. In certain embodiments, the aqueous buffer comprises $NH_4H_2PO_4$ and/or $NaH_2PO_4$. In certain embodiments, the analyzing method uses predominately binary mobile phases, e.g., two mobile phases together comprise >90%, >95%, >98%, or >99% v/v of the mobile phase. In certain embodiments, one mobile phase is an aqueous mobile phase, and one mobile phase is an organic mobile phase comprising, e.g., acetonitrile and/or methanol. In certain embodiments, the mobile phases further comprise a third mobile phase (e.g., one solvent or combination of solvents) that is ≤10% v/v of the mobile phase. By way of non-limiting example, a predominately binary solvent system could contain 60% water, 30% acetonitrile, and up to 10% another solvent or combination of other solvents, e.g., 10% methanol, 5% methanol and 5% ethanol, or any other combination that meets the necessary guidelines. In certain embodiments, the above conditions are used in an UPLC system. In certain embodiments, the analyzing method comprises using a Cx-Silicon based reversed phase column. In certain embodiments, x is 4, 8, or 16. In certain embodiments, the carbon components of the column are 16 carbons, 8 carbons or 4 carbons in linear length. In certain embodiments, the linear chain is further branched with varying alkyl groups (e.g., isopropyl). In certain embodiments, the UPLC utilizes a column containing average mean particle diameters of less than 3.0 microns, or less than 2.5 microns, or less than 2.0 microns. In certain embodiments, the column temperature is above RT, e.g., about 40 to about 90° C., about 40 to about 80° C., about 40 to about 70° C., about 40 to about 60° C., about 40° C., about 45° C., about 50° C., about 55° C., or about 60° C.

Provided in some embodiments of this disclosure are methods of analyzing an abaloparatide formulation for use in treating patients comprising:
(a) storing an aqueous abaloparatide formulation initially comprising ≤1.0% w/w (beta-Asp10), ≤0.5% ATP(3-34), ≤0.5% ATP(4-34), ≤0.5%(cyclo-Asp10), and ≤0.5% (cycloAsp17) of the total peptide content, an aqueous buffer having a pH of from 4.5-5.5, and an abaloparatide concentration of between 1.8 mg/mL and 2.2 mg/mL, for a first period of 23 months at between 2-8° C. and a second period of 1 month at 20-25° C., optionally 25±2° C., and
(b) analyzing said formulation by an analyzing method disclosed herein. For example, using HPLC and/or UPLC with a mobile phase comprising an aqueous phase and a buffer.

Provided in some embodiments of this disclosure are methods of treating a subject (e.g., human) with an abaloparatide formulation disclosed herein comprising (a) a first subcutaneous administration to the periumbilical area using a multi-dose injector pen, (b) a second and subsequent once-daily subcutaneous administrations to the periumbilical area using the same injector pen, wherein the subsequent administrations continue until 30 days has passed from the first administration, wherein said injector pen is stored at 20-25° C. from the first administration to the end of the 30 day administration period, and wherein the first, second, and subsequent administration all utilize the same dosage. In certain embodiments, said injector pen is discarded after the 30 day period. In certain embodiments, said dosage is about 80 µg abaloparatide. In certain embodiments, said abaloparatide formulation comprises a buffer. In certain embodiments, said abaloparatide formulation has a pH of about 4.5 to about 5.5. In certain embodiments, the second and subsequent administrations occur at approximately the same time of day as the first administration. In certain embodiments, the administration site is varied each day to different sites within the periumbilicular area. In certain embodiments, the subject has osteoporosis. In certain embodiments, the subject has severe osteoporosis. In certain embodiments, the subject is a postmenopausal woman at high risk for fracture. In certain embodiments, the subject has a history of osteoporotic fracture and/or multiple risk factors for fracture or who have failed or are intolerant of previous osteoporosis therapy.

Provided in some embodiments of this disclosure are methods of increasing bone mineral density in the hip, wrist, femoral neck or spine of a patient with osteoporosis comprising the administration of abaloparatide according to the treating methods disclosed herein.

Provided in some embodiments of this disclosure are methods of increasing bone mass in a male subject with primary or hypogonadal osteoporosis who are at high risk for fracture comprising the administration of abaloparatide according to the treating methods disclosed herein. In certain embodiments, the male subject has a history of osteoporotic fracture, or multiple risk factors for fracture, or has failed or are intolerant to previous osteoporosis therapy.

Provided herein in certain embodiments are methods of treating a condition in a subject in need thereof, e.g., a method of treating osteoporosis such as postmenopausal osteoporosis, glucocorticoid-induced osteoporosis, or male osteoporosis, treating osteoarthritis, or accelerating the rate or improving the outcome of bone fracture healing, wherein said methods utilize one or more of the detection, measurement, removal, purification, or storage methods provided herein. For example, methods of treatment are provided that comprise measuring the actual or relative amount of abaloparatide related peptides in an abaloparatide formulation prior to administering the formulation to a subject, wherein the formulation is only administered to the subject if the actual or relative amount of abaloparatide related peptides are at or below a predetermined threshold value. In another example, methods of treatment are provided that utilize an abaloparatide formulation stored according to the storage methods provided herein, optionally wherein the abaloparatide formulation is subjected to one or more of the detection, measurement, removal, or purification methods provided herein prior to storage, after storage, and/or at one or more timepoints during storage, for example just before the first administration or a subsequent administration of the formulation. In certain embodiments, methods are provided for treating a patient with an abaloparatide formulation comprising administering a first dosage of abaloparatide formulation that has been stored for a first period of about 0-23 or about 0-35 months at about 2-8° C., then storing the remaining abaloparatide formulation at room temperature, e.g., 20-25° C., for a second period of about 30 days or 30 days. In certain embodiments, these methods may utilize a multi-injection pen, and the pen is stored at room temperature for about 30 days (or 30 days) after the first administration, with the subject receiving one injection per day over that period and in some embodiments the daily dosage of abaloparatide is 80 µg. In certain embodiments, the formulation is administered at approximately the same time each day, such that dosages are administered about 24 hours apart. In some embodiments the patient discards the multi-injection pen after 30 days from the first injection (after a total of up to 30 once daily injections).

Provided herein in certain embodiments are methods of treating a condition in a subject in need thereof, e.g., a method of treating osteoporosis such as post-menopausal osteoporosis, glucocorticoid-induced osteoporosis, or male osteoporosis, a method of treating osteoarthritis, or , and/or accelerating the rate or improving the outcome of bone fracture healing, using a formulation provided herein. In certain embodiments, these methods incorporate one or more of the detection, measurement, removal, purification, or storage methods provided herein. In certain embodiments, the abaloparatide formulation is administered once daily for about 30 days. In certain embodiments of the methods of treatment provided herein, the abaloparatide formulation is administered via subcutaneous injection, for example to periumbilicular region.

In certain embodiments of the methods of treatment provided herein, a multi-dose injection pen is used to administer the drug. In certain of these embodiments, the multi-dose injection pen is stored according to the methods of storage provided herein. In certain embodiments, the multi-dose injection pen initially contains enough formulated abaloparatide drug product to allow for about 30 days of once daily injections, for example at a daily dosage of about 80 µg abaloparatide. For example, the pen may initially contain 2.4 mg or more of abaloparatide. In certain embodiments, the multi-dose injection pen may contain about 1.2 mL of formulated abaloparatide drug product at a concentration of about 2.0 mg/mL. In other embodiments, the multi-injection pen may contain more than enough formulated abaloparatide drug product for 30 days of once daily injections. For example, the pen may initially contain about 3.12 mg abaloparatide. In certain embodiments, the pen may contain about 1.56 mL of formulated abaloparatide drug formulation at an abaloparatide concentration of about 1.8-2.2 mg/mL, 1.86-2.10, 1.90-2.10 or about 2 mg/mL. In certain of these embodiments wherein the pen contains excess abaloparatide formulation for 30 days of once daily injections, the pen may nonetheless be indicated for disposal at the end of 30 days at room temperature. In certain embodiments, the injection pen is disposed after 30 days at room temperature regardless of how many injections (up to 30) have been administered and in certain embodiments the disposed pen still contains some aqueous formulated abaloparatide.

Provided in some embodiments of this disclosure are methods of establishing suitability of an abaloparatide manufacturing process and abaloparatide aqueous formulation comprising formulating abaloparatide API into an aqueous vehicle, wherein said abaloparatide API is first analyzed and determined to contain ≤0.5% beta-Asp10, ≤0.5% cyclo-Asp10, ≤0.5% cyclo-Asp17 of the total peptide content and where ATP(3-34) and ATP(4-34) are together ≤1.0% of the total peptide and wherein said API further comprises ≥97% of abaloparatide of the total peptide content in the API and further determining that the initially prepared aqueous abaloparatide containing formulation (t=0) comprises ≤1.0% beta-Asp10, ≤0.5% cyclo-Asp10, ≤0.5% cyclo-Asp17, ≤0.5% ATP(3-34) and ≤0.5% ATP(4-34) of the total peptide and wherein said aqueous further comprises ≥97% of abaloparatide of the total peptide content in the aqueous abaloparatide formulation and further embodiments, storing said aqueous abaloparatide formulations for 23 months and then storing at 25±2° C. for 1 month or 35 months and then storing at 25±2° C. for 1 month at 2-8° C. and then storing at 25±2° C. for 1 month and evaluating the drug product during and after said storage period and in certain of these embodiments each of said cyclo-Asp10, cyclo-Asp17, ATP (3-34) and ATP(4-34) is present in an amount of ≤0.5% of peptide content in the formulation and the abaloparatide content is ≥93% of the total of the peptide content in the sample. The following examples are provided to better illustrate the claimed invention and are not to be interpreted as limiting the scope of the invention. To the extent that specific materials or methods are mentioned, they are merely for purposes of illustration and are not intended to limit the invention. One skilled in the art may develop equivalent means without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Example 1

Identification of beta-Asp10 in Samples Containing Abaloparatide

The presence of (beta-Asp10) isomer in abaloparatide API, mixtures, and formulations was unexpectedly discovered using modifications to pre-existing liquid abaloparatide chromatography methods. It was found that resolution of the (beta-Asp10) abaloparatide peak could be accomplished with certain buffer systems using HPLC or UPLC. Identification and isolation of (beta-Asp10) abaloparatide isomer was complicated by the fact that the buffer system needed to resolve the mixture was incompatible with mass spectroscopy (MS), while the eluent solvent system that was compatible with MS was unable to resolve the isomer from its parent. This led to the development of a method whereby beta-Asp10 was separated from abaloparatide using HPLC with buffer embodiments described herein. Since MS coupled to the HPLC could not be used with the buffer, a physical quantity of beta-Asp10 was isolated and its structure was elucidated with MS and peptide degradation, and finally by comparison to a prepared sample of the beta-Asp10 isomer. Accordingly, the combined use of HPLC and UPLC with a phosphate buffer allowed for both the identification and optimization of chromatography analyses including the identification of several enumerated abaloparatide related impurities and/or degradants.

In order to understand the results obtained, (Methods 1-4 described below) comprising two different mobile phases (buffer and no buffer) applied to both an HPLC system and an UPLC system will be juxtaposed and discussed in detail below.

Method I: HPLC Using a Binary Solvent System with Trifluoroacetic Acid (TFA) to Analyze a Sample of Abaloparatide API.

Solubilization solvent (0.1N acetic acid) was prepared by adding 3.00 g±0.05 of acetic acid 100% to a 500 mL volumetric flask, bringing to volume with processed water, and sonicating for two minutes.

Mobile phase A (0.1% TFA (HPLC grade or equivalent) in processed water) was prepared by introducing about 900 mL processed water in a 1.0 L volumetric flask, then adding 1.0 mL TFA and bringing to volume with processed water. Mobile phase B (0.1% TFA in processed water/acetonitrile 20/80) was prepared by introducing 800 mL acetonitrile (HPLC grade), in a 1.0 L flask, then adding 200 mL processed water and 1.0 mL TFA (HPLC grade). Both mobile phases were sonicated for two minutes. If necessary for longer analyses, larger quantities of mobile phase were prepared by multiplying the weights and volumes above.

Test (actual test sample) and reference standard solutions were prepared using an analytical balance with a minimum weight of at least 5.0 mg. For test solution, 5.0 to 6.0 mg of abaloparatide API test sample was added to a clean vial and dissolved in the solubilization solvent to obtain a 1.0 mg/mL solution. Two sample solutions were prepared. For reference standard solution, 5.00 to 6.00 mg of abaloparatide API reference standard was added to a clean vial and dissolved in solubilization solvent to obtain a 1.00 mg/mL solution. Two reference standard solutions were prepared. The water content of the reference standard was determined on the same day as sample analysis. The same container was used for both water and abaloparatide API content determination. Identification admixture was prepared by mixing 250 μL of reference solution and 250 μL of test sample solution.

This method utilized a Zorbax 300SB C8 5 μm 250×4.6 mm Agilent Technologies #880995-906 (or equivalent) analytical HPLC column, and a liquid chromatographic system capable of gradient elution, e.g., an Agilent Series 1100 or equivalent, equipped with the following:

Pumps, column oven, Waters on-line mixer cat #WAT051518 (or equivalent) for baseline noise reduction;
Variable volume sample injector;
Thermostated sample injector;
Variable wavelength UV detector equipped with a standard flowcell (10 mm, 13 μL, maximum pressure 120 bar); and
Electronic integrator device such as Empower CDS or equivalent.

Detection was performed at UV 220 nm. The column temperature was +50° C. and the autosampler temperature was +10° C. The injection volume was 20 µL, the flow rate was 0.9 mL/min, and the analysis stop time was 35 minutes. Elution conditions are set forth in Table 1.

TABLE 1

Elution conditions of Method 1

| Time (min) | % mobile phase A | % mobile phase B |
|---|---|---|
| 0.0 | 71 | 29 |
| 25.0 | 65 | 35 |
| 35.0 | 65 | 35 |
| 36.0 | 71 | 29 |
| 45.0 | 71 | 29 |

The column was equilibrated by passing mobile phase through under the chromatographic conditions as set forth above until a stable baseline was achieved. The initial mobile phase composition could be adjusted ±1% B or the initial flow rate ±0.1 mL/min, keeping the same gradient slope, in order to obtain a retention time for abaloparatide API of about 18.2 minutes ±1 minute.

Five replicates of reference solution were injected for a system suitability test. The following parameters should be calculated according to the United States Pharmacopeia and the National Formulary (USP-NF).

The mean theoretical plates calculated by the CDS according to Empower standard field EP Plate Count for abaloparatide peak should be NLT 3000;

The mean tailing factor calculated by the CDS according to Empower standard field USP Tailing for abaloparatide peak should be NMT 4.5; and RSD % on abaloparatide peak area should be NMT 2.0%.

The injection sequence was as follows:

Run 1: Baseline (solubilization solvent)

Run 2: Reference standard solution (preparation 1- replicate 1)

Run 3: Reference standard solution (preparation 1- replicate 2)

Run 4: Reference standard solution (preparation 2- replicate 1)

Run 5: Test solution (preparation 1)

Run 6: Test solution (preparation 2)

Run 7: Reference standard solution (preparation 1)

Run 8: Reference standard solution (preparation 2- replicate 2)

Run 9: Reference standard solution (preparation 2- replicate 3)

Run 10: Identification admixture

Runs 2-4 and 7-9 could be skipped when abaloparatide API content was not being analyzed. If the identification was not required (e.g., retest, stability studies, . . . ) then Run 10 was not performed. The analytical sequence bracketed by reference standard solutions (e.g. runs 5-6) should not exceed 8 injections (4 test samples).

Any peaks observed in run 1 were subtracted from sample chromatograms. The peak area reject was set to 0.05% of the mean from the abaloparatide peak area obtained for the five reference standard injections from the system suitability test.

Figure 2:
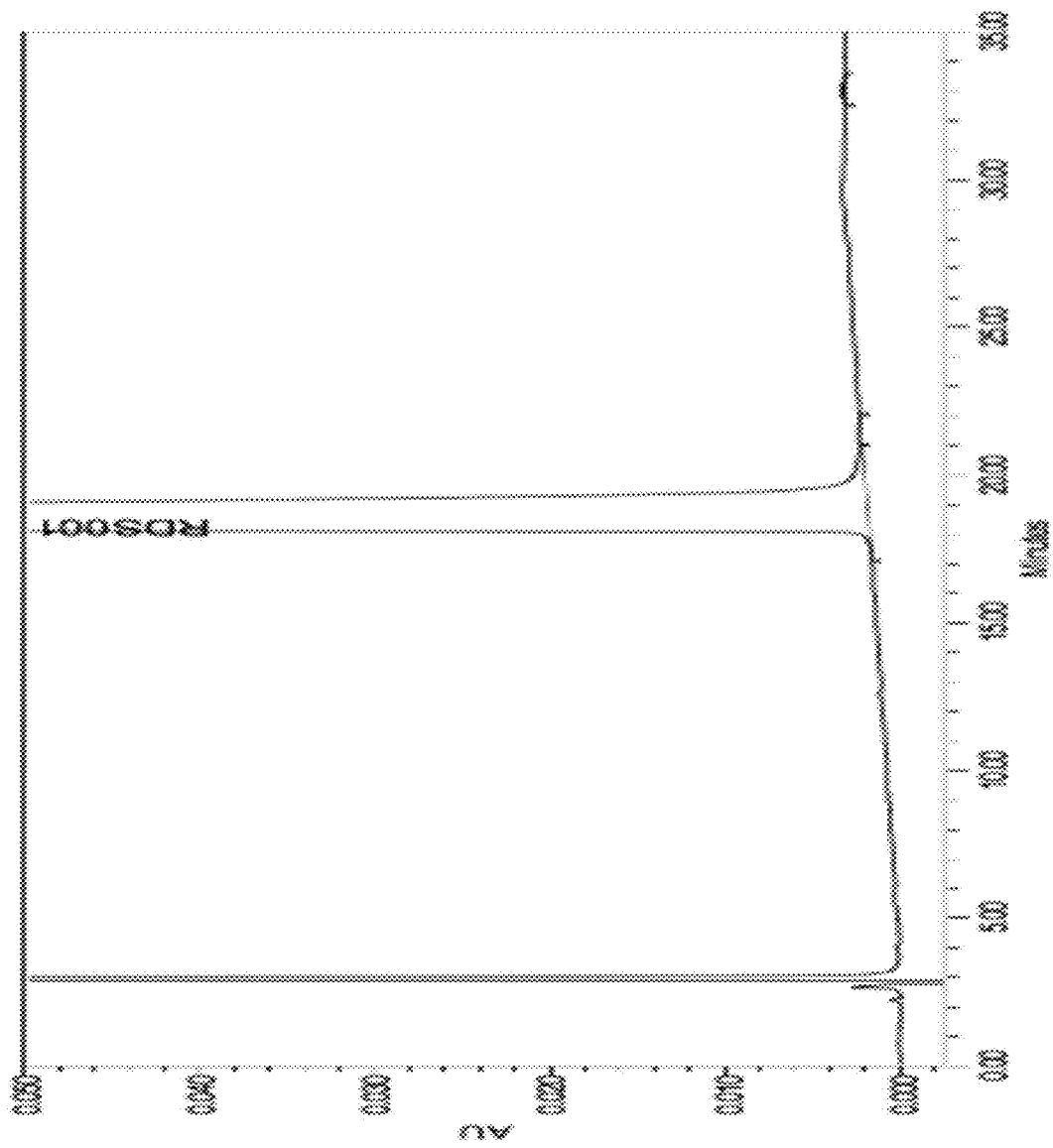
FIG. 2: Typical HPLC chromatogram of an abaloparatide sample (aqueous formulation at t=0) of abaloparatide using Method 1 (mobile phase of TFA, acetonitrile, and chromatography water).
Figure 3:
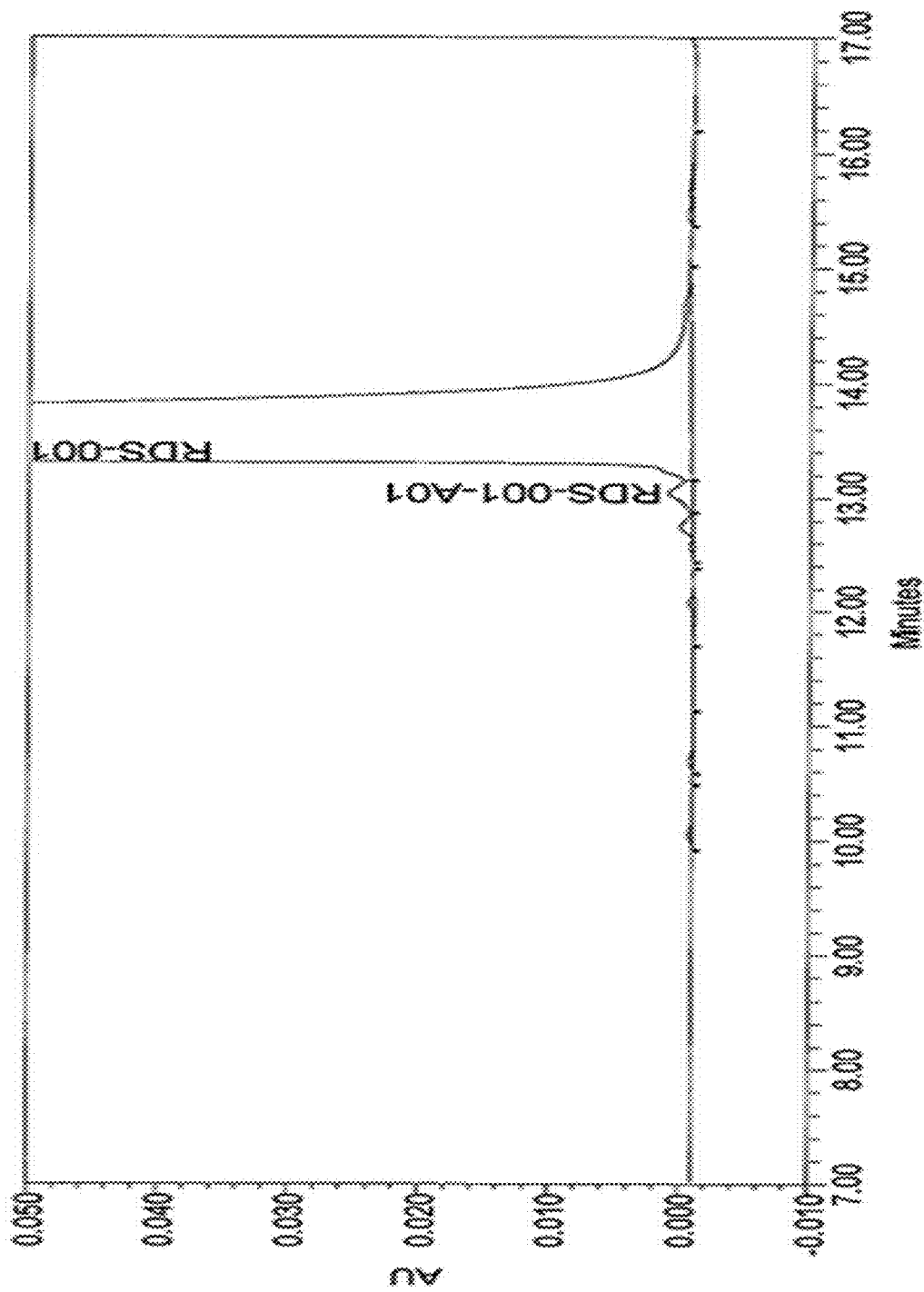
FIG. 3: Representative chromatogram from buffered LC run showing the beta-Asp10 impurity (RRT approximately 0.97 relative to abaloparatide (large peak)).

The chromatogram run according to method 1 conditions on the API showed a single significant peak (see FIG. 2).

Sample purity for each test solution chromatogram was calculated by area normalization % according to the following formula $$\text{Overall Purity (area \%, 1 decimal)} = \frac{\text{Peak area of Abaloparatide}}{\text{Total area of all peaks in the chromatogram}} \times 100$$

The level of each impurity in each test solution chromatogram was calculated by area normalization % according to the following formula $$\text{Impurity level (area \%, 1 decimal)} = \frac{\text{Related substance peak area}}{\text{Total area of all peaks in the chromatogram}} \times 100$$

The relative retention time (RRT) of impurities was calculated using the following formula:

$$RRT \text{ (2 decimals)} = \frac{RT_{imp}}{RT_{Abaloparatide} \text{ in the same chromatogram}}$$

where $RT_{imp}$ was retention time of the related impurity in minutes and $RT_{abaloparatide}$ was retention time of the abaloparatide peak in minutes.

Any peak corresponding to an unspecified impurity was reported to one decimal with its corresponding RRT.

The level of total impurities was calculated using the following formula

Total impurities(area %, decimal)=100−overall purity

The abaloparatide content in each test solution chromatogram was calculated according to the formula:

$$\text{Abaloparatide content } (w/w \text{ \%, 1 decimal}) = \frac{As \times Qr \times Cref}{Ar \times Qs \times 100} \times 100$$

wherein As was the abaloparatide peak area obtained in the test solutions, Ar was the mean of abaloparatide peak areas in the six bracketing injections of reference standard, Qr was the injected quantity of reference standard (µg), Qs was the injected quantity of sample (µg), Cref was the abaloparatide content of the reference standard determined by the formula:

$$\frac{\left(100 - H_2O\left(\% \frac{w}{w}\right) - AcOH\left(\% \frac{w}{w}\right) - \text{residual } TFA\left(\% \frac{w}{w}\right)\right) \times HPLC \text{ purity (area \%)}}{100}$$

(content determined on the same day that reference standard solution was prepared). A typical chromatogram from Method 1 is shown in FIG. 2, and results are summarized in Table 2.

TABLE 2

| | Name | RT | Area | % Area | Height (µV) | Relative_RT |
|---|---|---|---|---|---|---|
| 1 | RDS0001* | 18.255 | 7904259 | 99.83 | 187529 | 1.000 |
| 2 | | 21.217 | 6248 | 0.08 | 156 | 1.162 |
| 3 | | 32.955 | 7466 | 0.09 | 250 | 1.805 |
| Sum | | | 7917973 | | | |

*RDS0001 = abaloparatide

Method 2: UPLC Using a Binary Solvent System with TFA to Analyze a Sample of Abaloparatide API and a Partially Degraded Test Solution of Abaloparatide API.

This method utilized a UPLC procedure for evaluating overall purity, major single impurity, and total impurities of abaloparatide, API. The level of purity and impurities in abaloparatide, API were quantitated by area normalization.

Processed water was filtered through 0.22 in Simplicity Millipore or equivalent. Solvent (processed water/acetonitrile 50/50 (v/v)) was prepared by adding 140 mL of processed water and 140 mL of UPLC grade acetonitrile to a 500 mL bottle, homogenizing, and sonicating for two minutes. Mobile phase A2 (0.05% TFA in processed water) was prepared by adding 125 µL of UPLC grade TFA to about 100 mL of processed water in a 250 mL volumetric flask and bringing to volume with processed water. Mobile phase B2 (0.05% TFA in processed water/acetonitrile 50/50) was prepared by adding 125 µL of TFA to about 100 mL of solvent in a 250 mL volumetric flask and bringing to volume with solvent. Both mobile phases were homogenized and sonicated for two minutes. 250 mL of mobile phase A2 and 250 mL of mobile phase B2 were enough for 80 injections. If necessary for long analyses, larger quantity of mobile phase could be prepared by multiplying weights and volumes required.

Injector weak wash solution was processed water/acetonitrile (90/10), injector strong wash solution was processed water/acetonitrile (10/90). HCl 0.5N was prepared by adding 4.1 mL of HCl 37% to about 50 mL of water in a 100 mL volumetric flask, bringing to volume with processed water, homogenizing, and sonicating for two minutes. Tris(hydroymethyl)-aminomethane 0.05N (Tris) was prepared by adding 50 mL processed water to a 100 mL volumetric flask containing 0.60 g±0.02 g of Tris, bringing to volume with processed water, and homogenizing.

Test and resolution standard solutions were prepared using an analytical balance with a minimum weight of at least 5.00 mg in a humidity controlled area set to 30%±10% relative humidity. For test solution, 5.00 to 6.00 mg of abaloparatide sample was added to a clean vial and dissolved in processed water to obtain a 1.0 mg/mL solution. Two sample solutions (2-6.2.a and 2-6.2.b) were prepared. For resolution standard solution (1.0 mg/mL HCl 0.5N buffered with Tris 0.05N), 5.0 to 6.0 mg of abaloparatide reference standard was added to a clean vial and dissolved in HCl 0.5N to obtain a 10.0 mg/mL solution. After 90-120 minutes reaction time at +25° C. (RRT 1.02 impurity must be greater than 0.5% and less than 2%), nine volumes of Tris 0.05N were added to obtain a 1.0 mg/mL solution. The chromatographic profile must match the graph in FIG. 5.

This method utilized a Waters Acquity CSH C18 1.7 µm, 100×2.1 mm UPLC column. Detection was performed at UV 220 nm (20Hz). The column temperature was +40° C.±2° C. and the autosampler temperature was +10° C.±2° C. The injection volume was 2 µL, the flow rate was 300 µL/min, and the analysis stop time was 14.5 minutes. Elution conditions are set forth in Table 3.

TABLE 3

Elution conditions of Method 2

| Time (min) | % mobile phase A2 | % mobile phase B2 |
|---|---|---|
| 0.0 | 68 | 32 |
| 0.5 | 68 | 32 |
| 14.5 | 40 | 60 |
| 15.0 | 20 | 80 |
| 15.5 | 20 | 80 |
| 15.6 | 68 | 32 |
| 18.0 | 68 | 32 |

The initial mobile phase composition may be adjusted, keeping the same gradient slope, in order to obtain abaloparatide retention time between 8.5 and 9.5 minutes.

The injection sequence was as follows:
Run 1: Baseline process water (wash)
Run 2: Resolution standard solution
Run 3-7: Test solution (preparation 1)
Run 8: Baseline process water
Run 9: Test solution (preparation 1)
Run 10: Test solution (preparation 2)

Runs 2-8 would not be started unless the System Suitability Test (SST) parameters were met.

Figure 5:
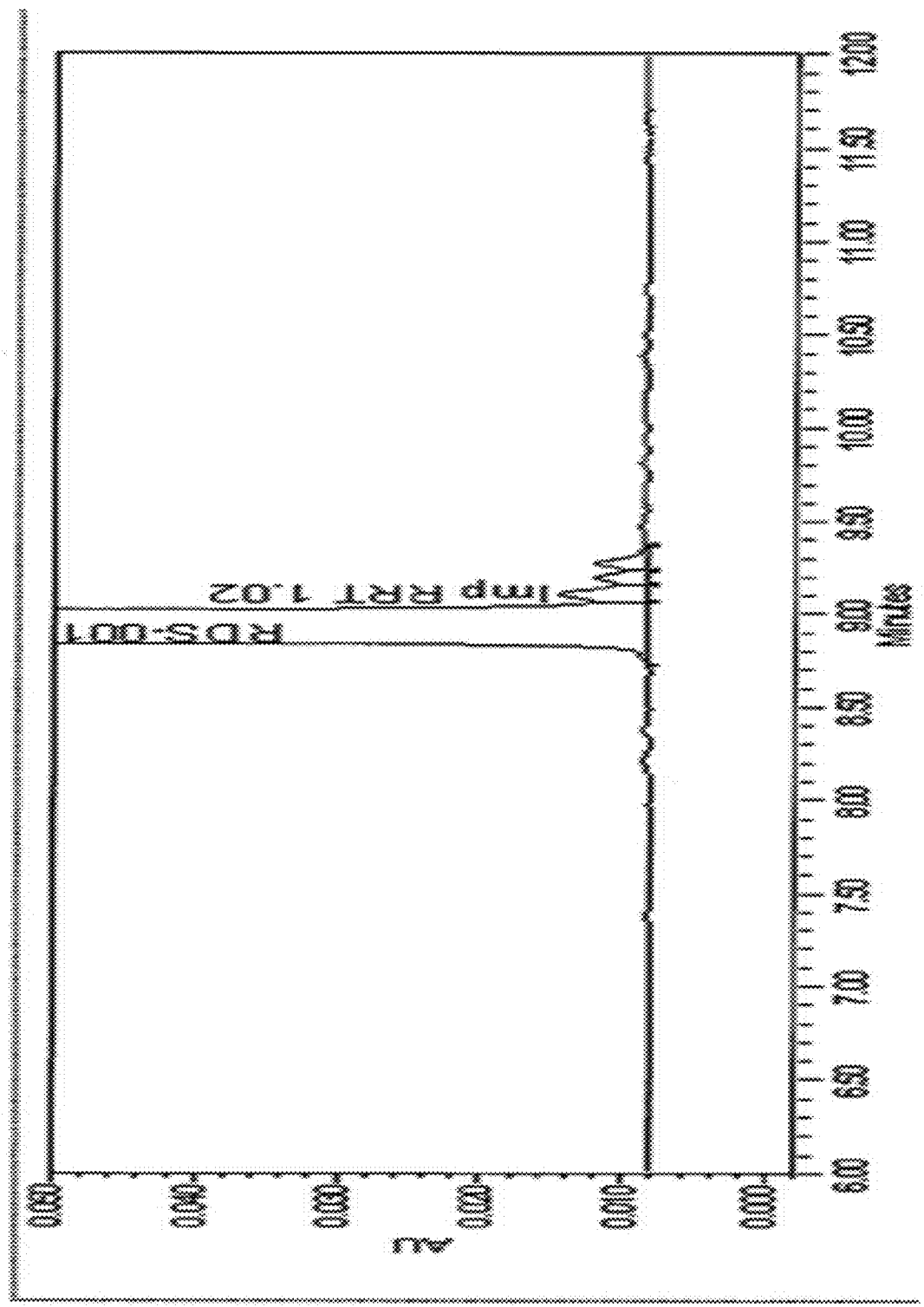
FIG. 5: Typical chromatogram from Method 2 for a resolution standard solution.

For run #2, the chromatographic profile must match the graph in FIG. 5 with 3 distinct peaks after main peak. The first impurity (RRT 1.02) must be between 0.5% and 2%.

For runs 2-7, the relative standard deviation (RSD) of abaloparatide peak area must be <2.0%. and RSD of abaloparatide retention time must be <2.0%.

For run 8, the area of any peak with a peak retention time corresponding to that of abaloparatide must be <2.0% of the mean peak area from runs 3-7.

Any peaks observed in run 8 were subtracted from sample chromatograms. The peak area reject was set to 0.05% of the mean from the abaloparatide peak area obtained for the duplicate injections from the sample.

Sample purity for runs 9 and 10 was calculated by area normalization % according to the following formula:

$$\text{Sample overall purity (area \%, 1 decimal)} = \frac{\text{Peak area of Abaloparatide}}{\text{Total area of all peaks in the chromatogram}} \times 100$$

The level of each impurity was calculated by area normalization % according to the following formula:

$$\text{Unspecified Impurity level (area \%, 1 decimal)} = \frac{\text{Related substance peak area}}{\text{Peak area of all peaks in the chromatogram}} \times 100$$

The level of total impurities was calculated using the following formula:

$$\text{Total impurities(area \%, decimal)} = 100 - \text{overall purity}$$

Figure 6:
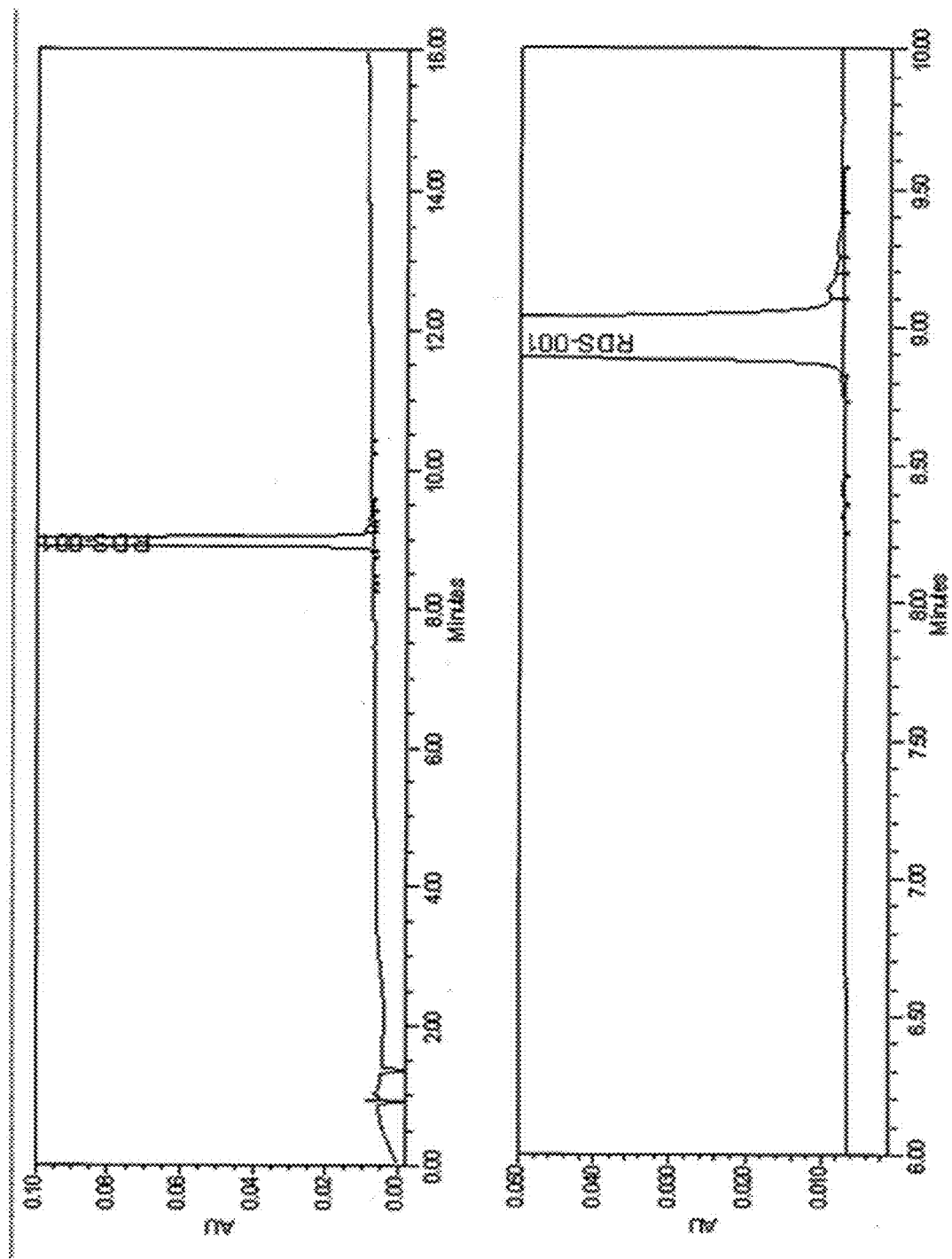
FIG. 6: Typical chromatogram from Method 2 for abaloparatide (aqueous formulation, t=0).

Typical chromatograms from Method 2 are shown in FIG. 5 and FIG. 6. Comparing FIG. 2 using HPLC vs FIG. 5 and FIG. 6 that use UPLC (neither with buffer) some additional peaks appear right after the abaloparatide (main) peak in the UPLC method, indicating it has increased resolution compared to HPLC. Notably, (b-Asp10) is identified in neither Method 1 or Method 2.

Method 3: HPLC Using a Binary Solvent System with Ammonium Phosphate (($NH_4$)$_2$$PO_4$) to Analyze a Sample of Abaloparatide API Against a Partially Degraded Test Solution This method utilized a HPLC procedure for identification, overall purity, major single impurity, total impurities, and assay determination of abaloparatide, API. The level of purity and impurities in abaloparatide, API are quantitated by area normalization.

Stock solution 3-5.1 (0.8 M $H_3PO_4$ in processed water) was prepared by adding 28 mL of 85% o-phosphoric acid (analytical grade or equivalent) to 200 mL of processed water (MAP -067/187 or equivalent) in a 500 mL volumetric flask and bringing to volume with processed water. Stock solution 3-5.2 (320 mM ($NH_4$)$_2$$HPO_4$ in processed water) was prepared by adding 400 mL of stock solution 3-5.1 and 100 mL processed water to a 1 liter flask, adjusting the pH to 7.8 using $NH_4OH$ (30% ammonia solution analytical grade or equivalent), transferring the solution in a volumetric flask and bringing to 1.0 L with processed water, and sonicating for two minutes.

Mobile phase A (128 mM ($NH_4$)$_2$$HPO_4$ in processed water) was prepared by adding 600 mL of processed water to 400 mL of stock solution 3-5.2 in a 1 liter flask and sonicating for two minutes. Mobile phase B ((70% 320 mM ($NH_4$)$_2$$HPO_4$/30% processed water)/acetonitrile (50/50)) was prepared by adding 150 mL of processed water and 500 mL of HPLC grade acetonitrile to 350 mL of stock solution 3-5.2 in a 1 liter flask and sonicating for two minutes.

For test solution, 9.50 to 10.50 mg of abaloparatide, API test sample was added to a clean vial and dissolved in processed water to obtain a 2.0 mg/mL solution. Two test solutions were prepared. For reference standard solution, 9.50 to 10.50 mg of abaloparatide, API reference was added to a clean vial and dissolved in processed water to obtain a 2.0 mg/mL solution. Two reference standard solutions are prepared . Identification admixture was prepared by mixing 250 µL of reference solution and 250 µL of test sample solution.

For resolution test solution, 9.50 to 10.50 mg of abaloparatide, API reference standard was added to a clean vial and dissolved in 0.01N sodium hydroxide to obtain a 4.0 mg/mL solution. This solution was heated at +40° C. for four hours, and then one volume of 0.01N hydrochloric acid was added to neutralize. Abaloparatide reference standard and degraded solution (2 mg/mL) were injected successively following the method. The appropriate volumes from both solutions were mixed to obtain an area percent content for RRT 1.07 degradation impurity between 2.0 and 2.5%. The solution was stored at −20° C.

This method utilized an X-Bridge C18 5 µm 150×4.6 mm Waters #186003116 (or equivalent) analytical HPLC column, and an HPLC system capable of gradient elution, e.g., an Agilent Series 1100 or equivalent, equipped with the following:
  Pumps, column oven, Waters on-line mixer cat #WAT051518 (or equivalent) for baseline noise reduction;
  Variable volume sample injector;
  Thermostated sample injector;
  Variable wavelength UV detector equipped with a standard flowcell (10 mm, 13 µL, maximum pressure 120 bar); and
  Electronic integrator device such as Empower CDS or equivalent.

Detection was performed at UV 214 nm. The column temperature was +60° C. and the autosampler temperature was +15° C. The injection volume was 20 µL, the flow rate was 0.8 mL/min, and the analysis stop time was 60 minutes. Elution conditions are set forth in Table 4.

TABLE 4

Elution conditions of Method 3

| Time (min) | % mobile phase A | % mobile phase B |
|---|---|---|
| 0.0 | 77 | 23 |
| 12.0 | 53 | 47 |
| 46.0 | 53 | 47 |
| 56.0 | 43 | 57 |
| 58.0 | 0 | 100 |
| 63.0 | 0 | 100 |
| 65.0 | 77 | 23 |
| 75.0 | 77 | 23 |

The initial mobile phase composition may be adjusted ±1% B or the initial flow rate ±0.1 mL/min, keeping the same gradient slope, in order to obtain a retention time for abaloparatide API between 32 and 36 minutes.

The column was equilibrated by passing mobile phase through under the chromatographic condition defined above until a stable baseline was achieved.

Five replicates of test solution were injected for a system suitability test. The following parameters was calculated according to USP-NF:
  The mean theoretical plates calculated by the CDS according to Empower standard field EP Plate Count for abaloparatide peak must be NLT 16000;
  The mean tailing factor calculated by the CDS according to Empower standard field USP Tailing for abaloparatide peak must be NMT 1.8; and
  RSD % on abaloparatide peak area must be NMT 1.0%.

Resolution test solution was further injected for the system suitability test, and the Empower CDS custom filed "Peak-to-valley-front-ratio" was used to report the Height/Valley ratio between abaloparatide and RRT 1.07 impurity peaks. This ratio should be not lower than 1.43.

The injection sequence was as follows:
  Run 1: Baseline (processed water)
  Run 2: Reference standard solution (preparation 1 replicate 1)
  Run 3: Reference standard solution (preparation 1 replicate 2)
  Run 4: Reference standard solution (preparation 2 replicate 1)
  Run 5: Test solution (preparation 1)
  Run 6: Test solution (preparation 2)
  Run 7: Reference standard solution (preparation 1 replicate 3)
  Run 8: Reference standard solution (preparation 2 replicate 2)
  Run 9: Reference standard solution (preparation 2 replicate 3)
  Run 10: Identification admixture Runs 2-4 and 7-10 may be skipped when abaloparatide identification and assay are not requested. Identification of abaloparatide is confirmed by the chromatogram obtained from Run 10 showing a single significant peak.

The individual related substance content and sample purity from Runs 5 and 6, excluding any peak observed in Run 1, were determined. Sample purity for each test solution chromatogram was calculated by area normalization % according to the following formula:

$$\text{Sample overall purity (area \%, 1 decimal)} = \frac{\text{Peak area } RDS\text{-}001}{\text{Peak area of all peaks in the chromatogram}} \times 100$$

The level of each impurity was calculated by area normalization % according to the following formula:

$$\text{Impurity level (area \%, 1 decimal)} = \frac{\text{Related substance peak area}}{\text{Peak area of all peaks in chromatogram}} \times 100$$

The level of total impurities was calculated using the following formula:

Total impurities(area %, 1 decimal)=100−overall purity

Figure 4:
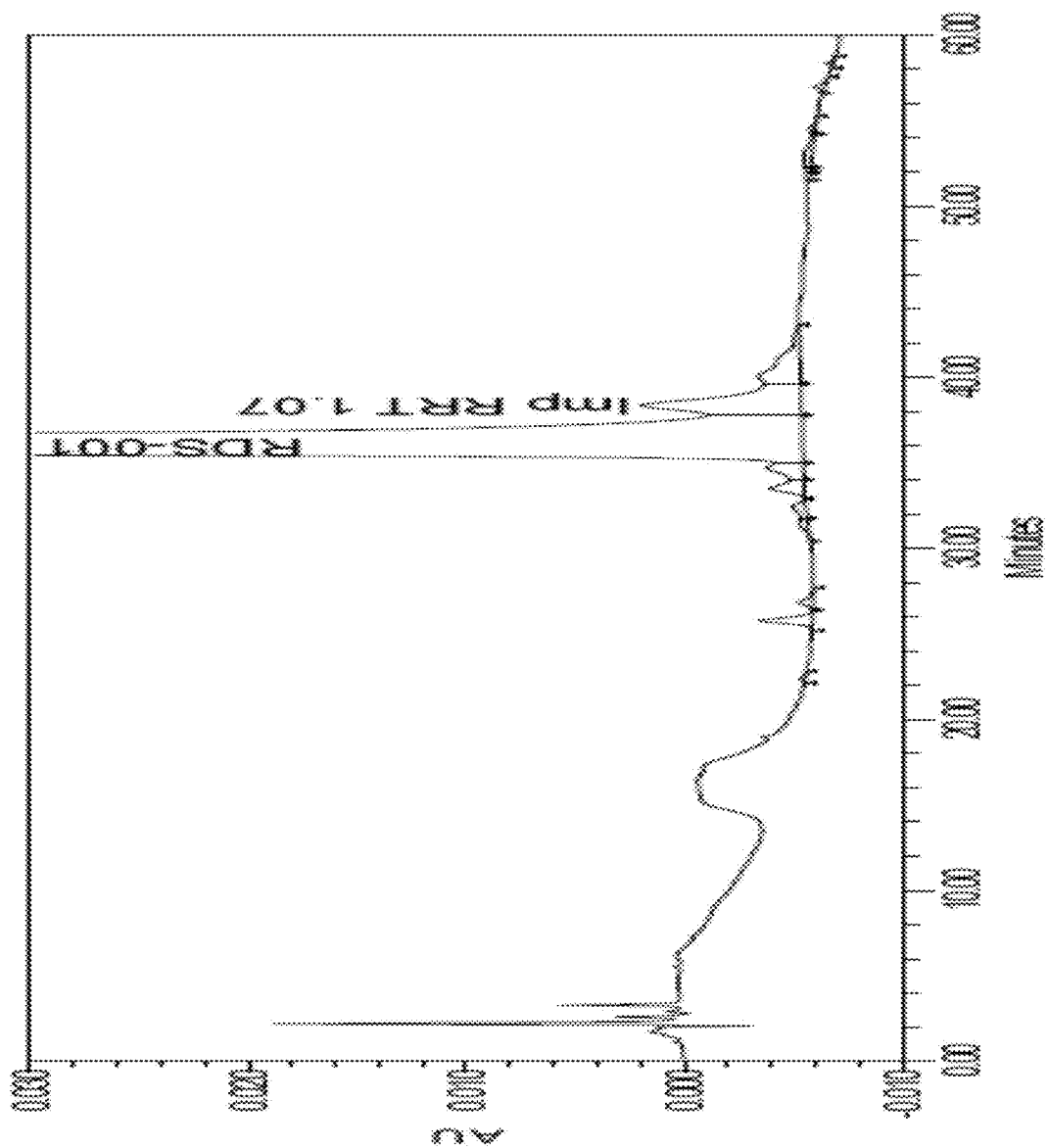
FIG. 4: Chromatogram from buffered LC of a chemically degraded (resolution test standard) abaloparatide aqueous formulation.

The assay of abaloparatide was calculated according to the formula: Abaloparatide assay $$(m/m\ \%,\ 1\ \text{decimal}) = \frac{A sample \times Qref \times CRDS\text{-}001ref \times PRDS\text{-}001ref}{Aref \times Qsample \times 100 \times 100} \times 100$$

wherein Asample was the mean of the abaloparatide peak areas in the two injections of test sample, Qref was injected quantity of reference standard (μg), CRDS-001ref was the abaloparatide peptide content of the reference standard calculated as (100%-% water-% acetic acid), PRDS-001ref was the mean purity (area percent) of the abaloparatide in the six bracketing injections of reference standard, Aref was the mean of the abaloparatide peak areas in the six bracketing injections of reference standard (Runs 2-4 and 7-9), and Qsample was the injected quantity of sample (m). A chromatogram of the partially degraded reference standard using the conditions described is shown in FIG. 4.

Method 4: UPLC Using a Binary Solvent System with Ammonium Phosphate $((NH_4)_2PO_4)$ to Analyze a Sample of Abaloparatide API Against a Partially Degraded Test Solution This method utilized a UPLC procedure for identification, overall purity, individual impurity, total impurities, and content determination of abaloparatide, API. The level of purity and impurities in abaloparatide, API are quantitated by area normalization.

Stock solution (97 mM $(NH_4)_2HPO_4$ in processed water) was prepared by adding 5.6 g of 85% phosphoric acid (the same as used in Method 3) to 450 mL of processed water (the same as used in Method 2) in a 500 mL bottle, adjusting the pH to 7.8 by adding $NH_4OH$ (the same as used in Method 3), transferring the solution to a volumetric flask, and bringing to 500 mL volume with processed water.

Mobile phase A2 (39 mM $(NH_4)_2HPO_4$ in processed water) was prepared by adding 100 mL of stock solution and 150 mL of processed water to a 250 mL bottle, mixing, and sonicating for two minutes. Mobile phase B2 ((70% 97 mM $(NH_4)_2HPO_4$/30% processed water)/acetonitrile (50/50)) was prepared by adding 140 mL of stock solution, 60 mL processed water, and 200 mL acetonitrile (the same as used in Method 2) to a 500 mL volumetric flask, mixing, and sonicating for two minutes.

Injector weak wash solution was processed water/acetonitrile (90/10), injector strong wash solution was processed water/acetonitrile (10/90). HCl 1N was prepared by adding 4.1 mL of HCl 37% to about 20 mL of water in a 50 mL volumetric flask, bringing to volume with processed water, homogenizing, and sonicating for two minutes. HCl 0.01N was prepared by adding 1 mL of HCl 1N to about 20 mL of water in a 100 mL volumetric flask, bringing to volume with processed water, homogenizing, and sonicating for two minutes. NaOH 0.01N was prepared by 1 mL of NaOH 1N to about 20 mL of processed water in a 100 mL volumetric flask, mixing, bringing to volume with processed water, and sonicating for two minutes.

Test and resolution standard solutions were prepared using an analytical balance with a minimum weight of at least 5.00 mg in a humidity controlled area set to 30%±10% relative humidity. For test solution, 5.00 to 6.00 mg of abaloparatide sample was added to a clean vial and dissolved in processed water to obtain a 1.0 mg/mL solution. Two sample solutions (4-6.3.a and 4-6.3.b) were prepared.

For reference standard solution (RSS 1.0 mg/mL, $H_2O$), 5.00 to 6.00 mg of abaloparatide (RDS-001) reference standard was added to a clean vial and dissolved in processed water to obtain a 1.0 mg/mL solution. Two reference standard solutions (4-6.1.a and 4-6.1.b) were prepared.

For resolution standard solution (1.0 mg/mL 0.01N NaOH/neutralized by 0.01N HCl), 5.00 to 6.00 mg of abaloparatide, API reference standard was added to a clean vial and dissolved in 0.01N sodium hydroxide to obtain a 2.0 mg/mL solution. The solution was heated at +40° C. for four hours, and the same volume of 0.01N hydrochloric acid was added to neutralize and produce a 1.0 mg/mL degraded solution (4-6.2.1). For resolution standard solution dilution, reference standard solution (4-6.1.a) and degraded solution (4-6.2.1) were injected successively as follows:

Integrate and determinate respectively area percent content for RRT 1.07 degradation impurity.

Calculate the appropriate volume of each solution to be mixed to obtain an area percent content for RRT 1.07 degradation impurity between 2.0 and 2.5%.

Make the mixing and inject the Resolution standard solution to check the content for RRT 1.07 degradation impurity. If necessary, adjust the mixing.

Identification admixture (4-6.4) was prepared by mixing 250 μL of reference solution (4-6.1.a) and 250 μL of test sample solution 4-6.3.a.

This method utilized a Waters Acquity BEH300 C4 1.7 μm, 150×2.1 mm analytical HPLC column (Part No. 186004497). Detection was performed at UV 220 nm. The column temperature was +60° C.±2° C. and the autosampler temperature was +10° C.±2° C. The injection volume was 5 μL, the flow rate was 300 μL/min, and the analysis stop time was 21.0 minutes. Elution conditions are set forth in Table 5.

TABLE 5

| Elution conditions of Method 4 | | |
|---|---|---|
| Time (min) | % mobile phase A2 | % mobile phase B2 |
| 0.0 | 52 | 48 |
| 1.5 | 52 | 48 |
| 18.5 | 39 | 61 |

TABLE 5-continued

Elution conditions of Method 4

| Time (min) | % mobile phase A2 | % mobile phase B2 |
|---|---|---|
| 19.0 | 1 | 99 |
| 21.0 | 1 | 99 |
| 21.5 | 52 | 48 |
| 25.0 | 52 | 48 |

The initial mobile phase composition may be adjusted within 0.0 and 18.5 minutes, keeping the same gradient slope, in order to obtain an abaloparatide retention time between 12.5 and 13.5 minutes. The mobile phase composition at 19.0 and 21.0 minutes must be kept unchanged to wash the column with 99% mobile phase B2.

The injection sequence was as follows:

Run 1: Baseline process water (wash)
Run 2: Resolution standard solution 4-6.2
Runs 3-7: Test solution 4-6.3.a
Run 8: Baseline process water
Run 9: Reference standard solution 4-6.1.a replicate 1
Run 10: Reference standard solution 4-6.1.a replicate 2
Run 11: Reference standard solution 4-6.1.b
Run 12: Test solution 4-6.3.a
Run 13: Test solution 4-6.3.b
Run 14: Reference standard solution 4-6.1.a
Run 15: Reference standard solution 4-6.1.b replicate 1
Run 16: Reference standard solution 4-6.1.b replicate 2
Run 17: Identification admixture 4-6.4

A maximum of five samples (10 injections) was allowed between two bracketing standards. Runs 2-15 are skipped when identification was not requested. Runs 9-11 and 14-17 were skipped when content determination is not requested.

Runs 2-8 would not be started unless the §9.1 System Suitability Test (SST) parameters were met.

Resolution standard solution (Run 2) was injected for the system suitability test, and the Empower CDS custom filed "Peak-to-valley-front-ratio" was used to report the Height/Valley ratio between abaloparatide and RRT 1.07 impurity peaks. This ratio should be not lower than 1.43.

Test solution injections(Runs 3-7) were further injected for the system suitability test, the following parameters must be calculated:

The relative standard deviation (RSD) of abaloparatide peak area must be <2.0%.

The RSD of abaloparatide retention time must be <2.0%

Run 8 (blank injection) was carried out also for the system suitability test, the area of any peak with a peak retention time corresponding to that of abaloparatide must be <2.0% of the mean peak area of Runs 3-7 injections.

The sample chromatograms were subtracted with any peak observed in the blank chromatogram (Run 8). The peak area reject was set to 0.05% of the mean from abaloparatide peak area obtained for the duplicate injections from the sample.

Chromatogram obtained from Run 17 showed a single significant peak.

The individual related substance content and the sample purity were determined from Runs 12 and 13.

For each sample solution chromatogram, the sample purity in area normalization was calculated according to the formula:

$$\text{Sample overall purity (area \%, 1 decimal)} = \frac{\text{Peak area } RDS\text{-}001}{\text{Peak area of all peaks in chromatogram}} \times 100$$

"Any unspecified impurity" term corresponds to the highest individual impurity, excluding the known impurities such as the truncated peptides and the beta-asp 10 isomer.

The level of total impurities was calculated according to the formula:

$$\text{Total impurities(area \%, 1 decimal)} = 100 - \text{overall purity}$$

The beta-Asp10 isomer (RDS-001-A01) was eluted at approximately RRT 0.97. For each sample solution chromatogram, the beta-Asp10 isomer level was calculated in area normalization according to the formula:

$$\text{Beta-}asp10 \text{ isomer(\% area, 1 decimal)} = \frac{\text{Peak area Beta-}asp10 \text{ isomer}}{\text{peak area of all peaks in chromatogram}} \times 100$$

The truncated peptides were eluted at approximately at RRT 0.92 (RDS-001-106; ATP (3-34) and RRT 0.93 (RDS-001-105; ATP(4-34)). For each sample solution chromatogram, the RDS-001-105 and RDS-001-106 levels were calculated in area normalization according to the formula:

$$\text{Truncated peptides (\% area, 1 decimal)} = \frac{\text{Peak area } RDS\text{-}001\text{-}105 \text{ and } RDS\text{-}001\text{-}106}{\text{peak area of all peaks in chromatogram}} \times 100$$

The abaloparatide content in each test solution chromatogram as calculated according to the formula below and as final result the mean content from the two sample preparations $$RDS-001 \text{ content } (w/w \text{ \% area, 1 decimal)} = \frac{As \times Qr \times Cref \times Pref}{Ar \times Qs \times 100 \times 100} \times 100$$

where:
As: Abaloparatide peak area obtained in the test solutions
Ar: Mean of abaloparatide peak areas in the six bracketing injections of reference standard
Qr: Injected quantity of reference standard (μg)
Qs: Injected quantity of sample (μg)
Cref: peptide content of the reference standard calculated as per following formula:

$$Cref = 100 - H_2O(\% \text{ w/w}) - AcOH(\%w/w) - \text{residual TFA } (\%w/w)$$

(Water content determined the same day as the reference standard solution is prepared).

Figure 9A:
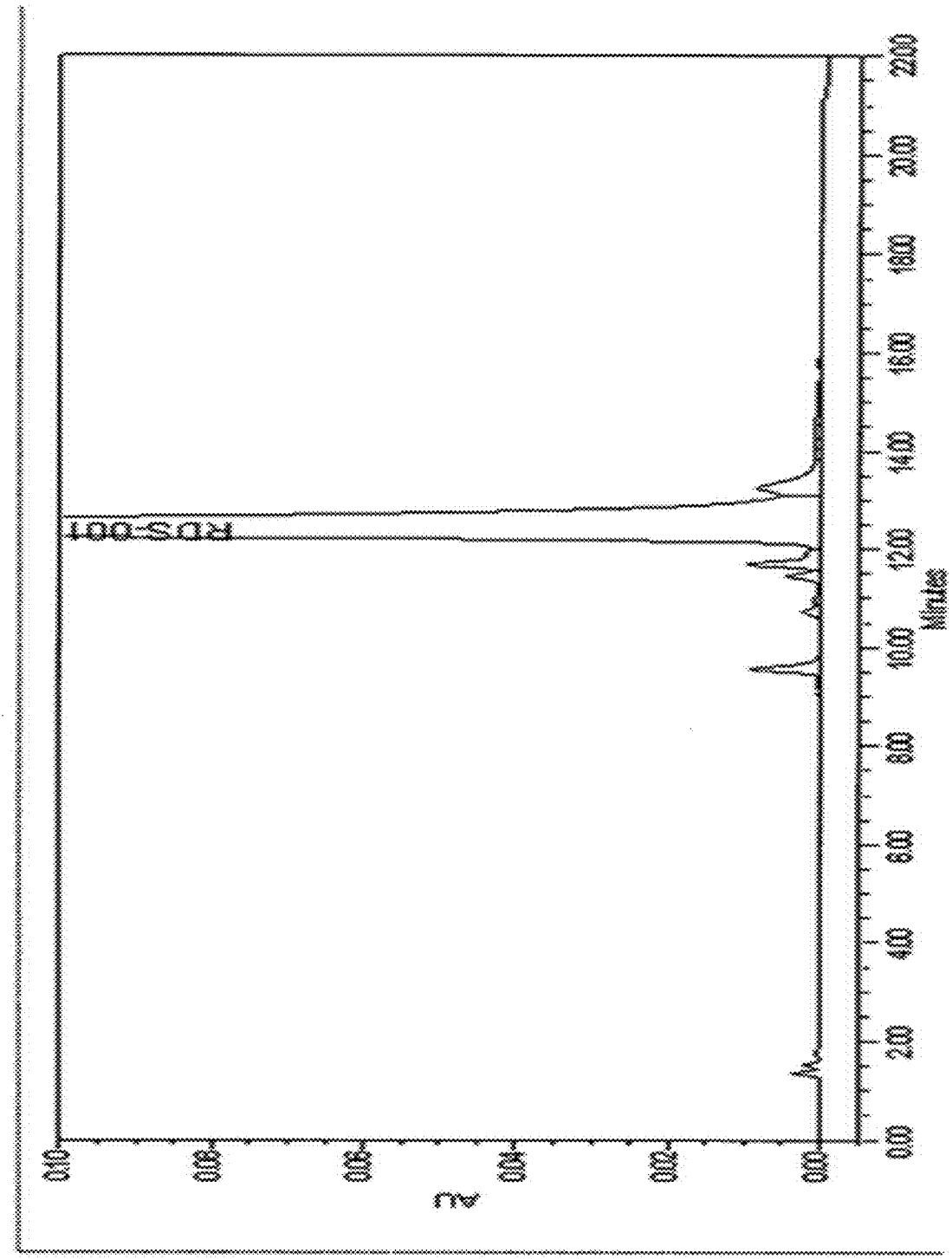
FIGS. 9A-9C: Chromatograms from Method 4.
Figure 9B:
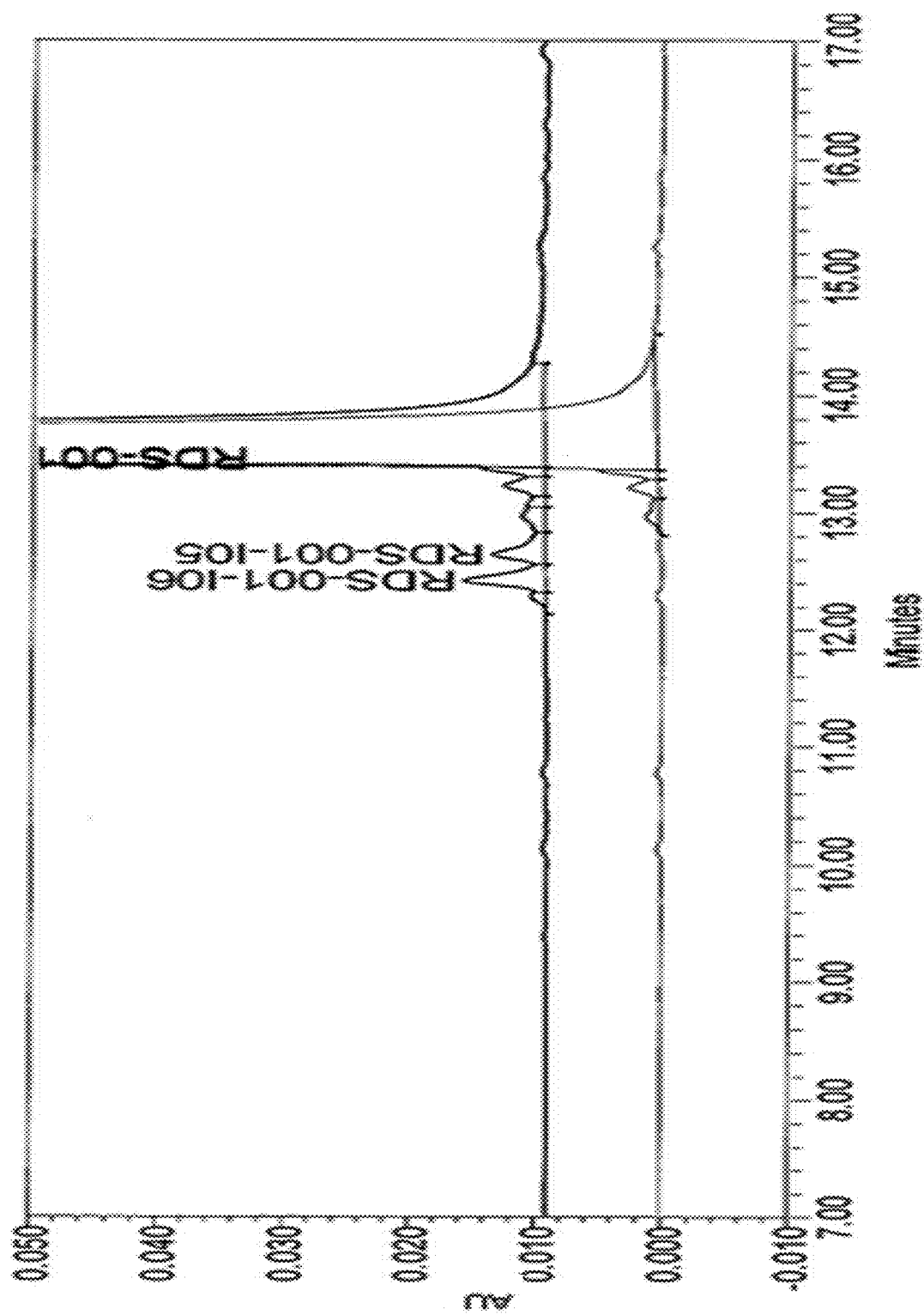
Figure 9C:
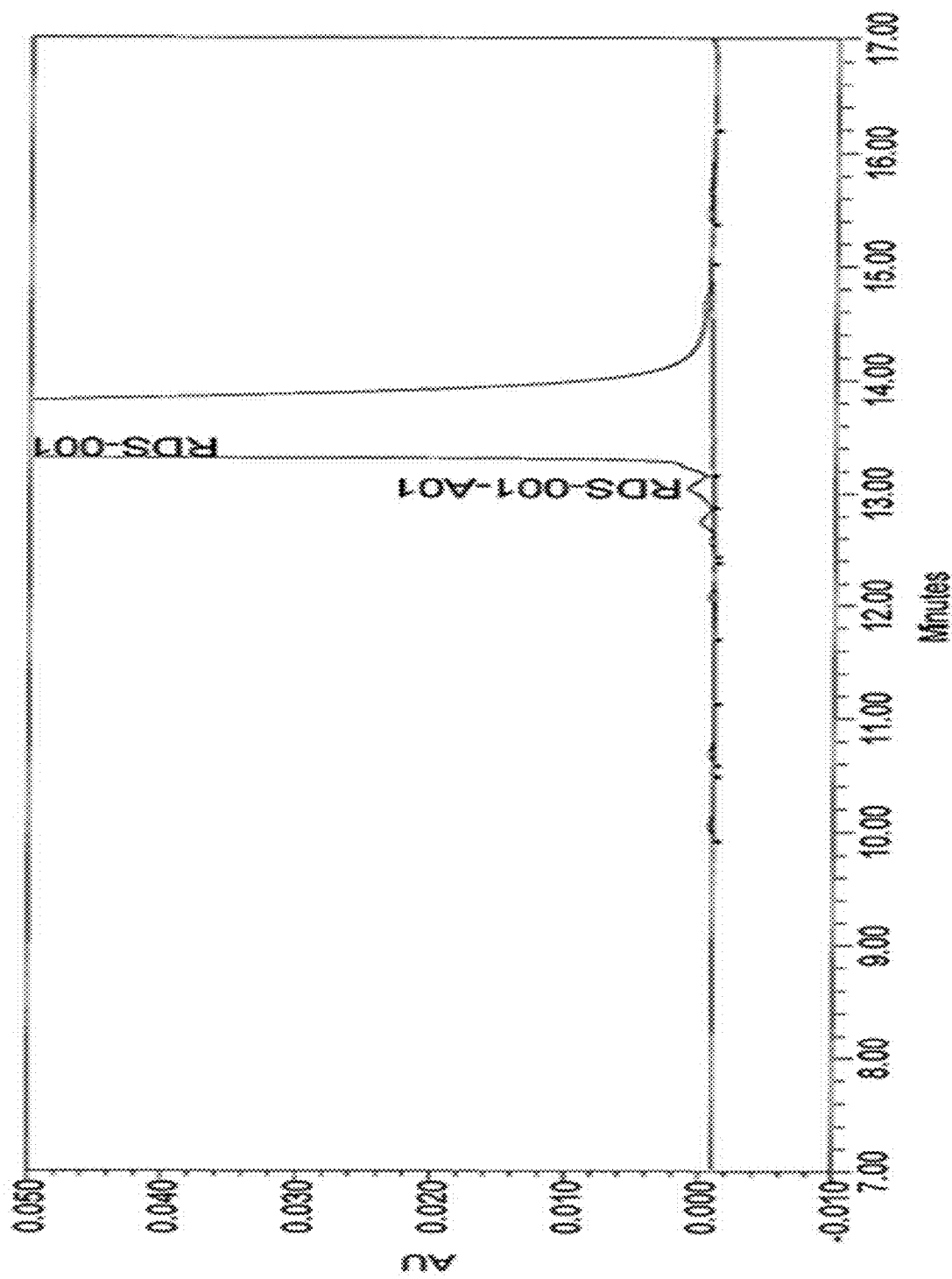

Pref: Mean of abaloparatide peak purity in the six bracketing injections of reference standard
100: factor for conversion of content expressed as mg/mL.
Chromatograms from Method 4 are shown in FIGS. 9A-C.

Example 2

Comparison of Methods 1 and Method 3 on Formulated Drug

Figure 10A:
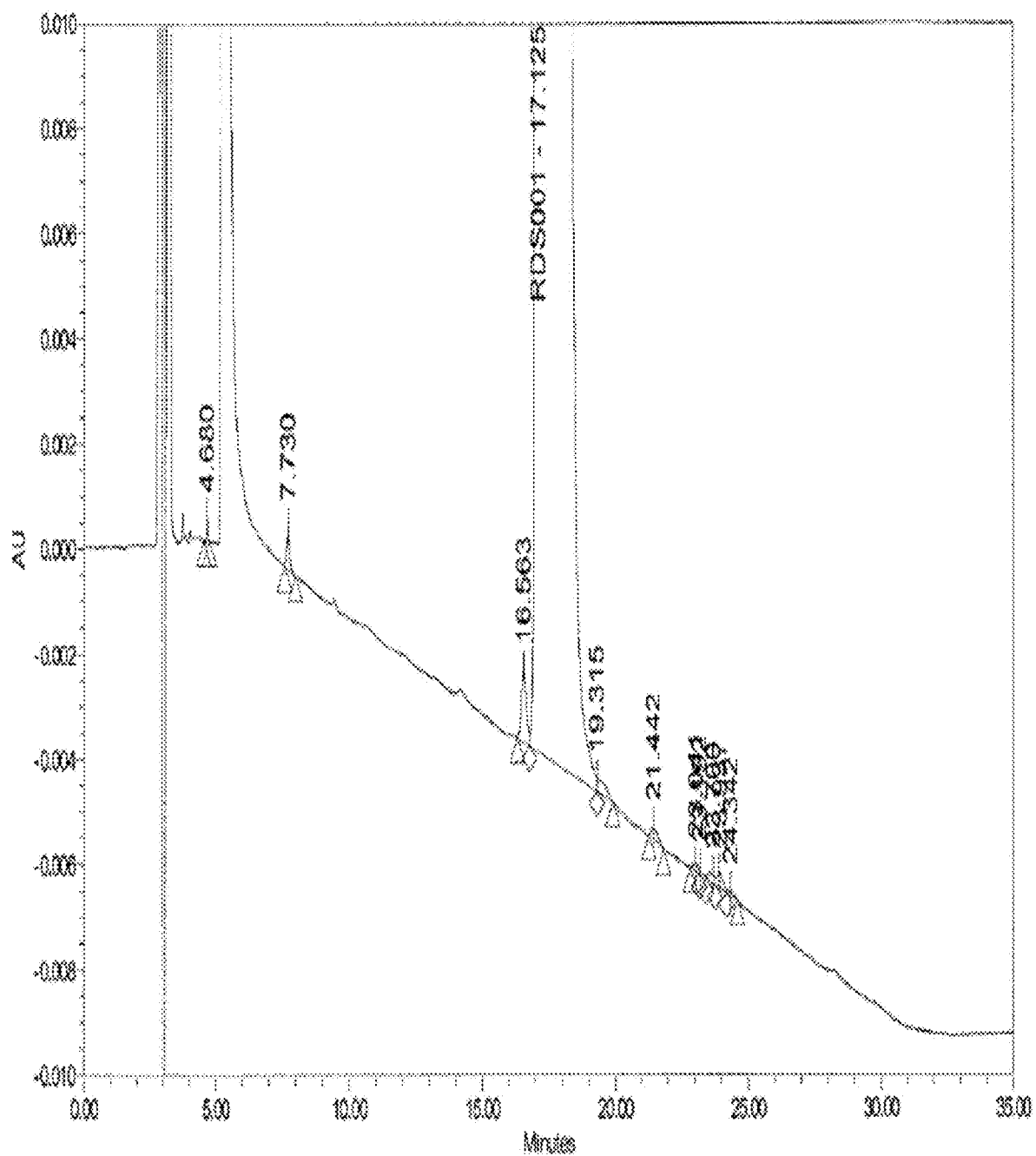
FIGS. 10A-10B: Formulated abaloparatide drug product chromatograms.
Figure 10B:
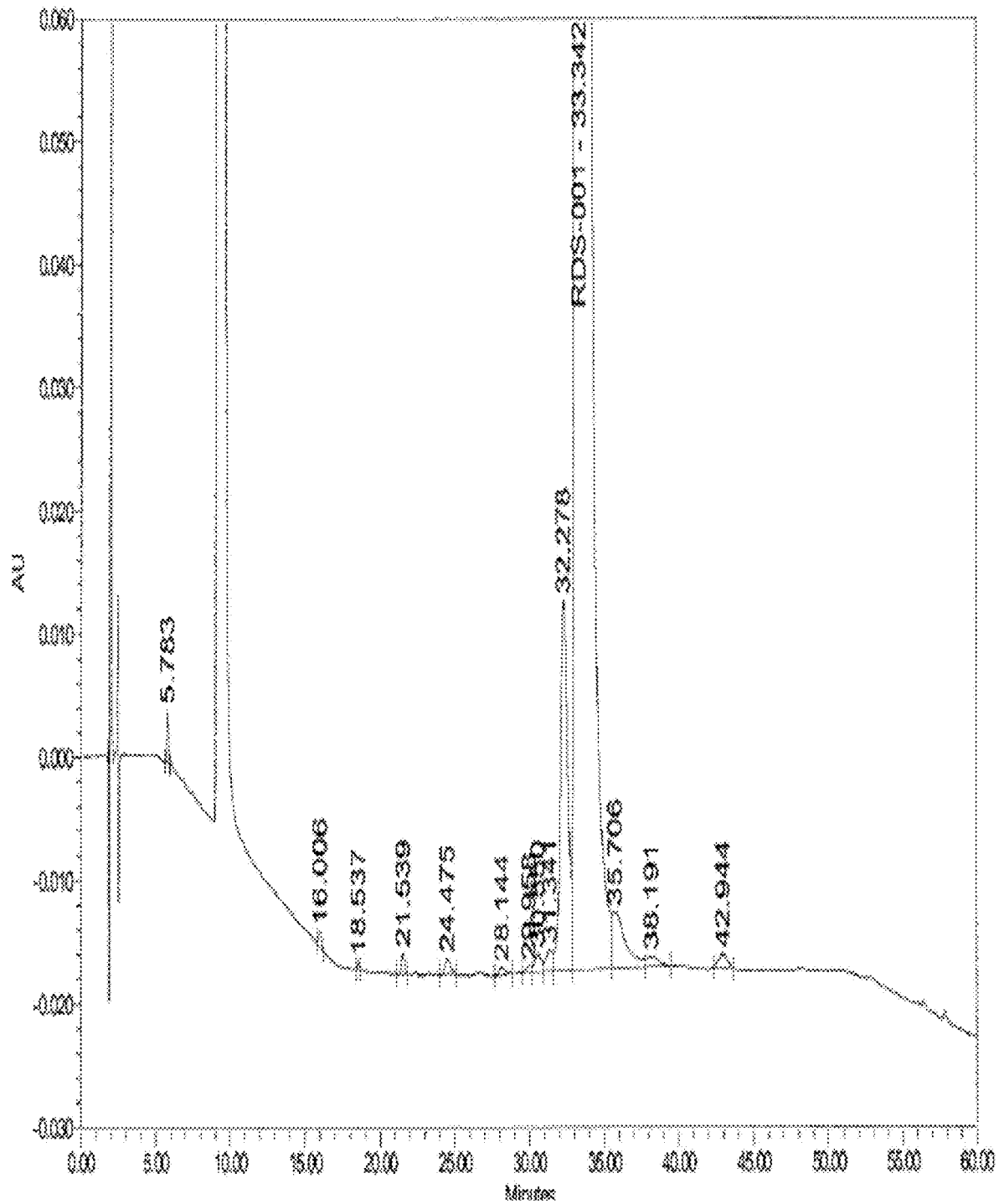

The HPLC method in TFA solvent system was validated and implemented as described in Method 1. In addition, Method 3 describes a phosphate-buffered mobile phase. Method 1 and Method 3 were compared for the same abaloparatide formulated drug sample. These results are shown in FIGS. 10A-B. A front running impurity peak not previously seen when using Method 1 (or 2) was separated out using Method 3. In addition, the two truncated peptides (ATP(3-34) and ATP(4-34)) were resolved using the UPLC method as described below.

TABLE 6

Formulated drug product batch analysis by Method 1. Purity areas and relative retention times ("RRT"; abaloparatide = 1)

| BEJH09 a | | BEJH09 b | | BEJJ12 a | | BEJJ12 b | | BEJH09 c | |
|---|---|---|---|---|---|---|---|---|---|
| RRT | % area | RRT | % area | RRT | % area | RRT | % area | RRT | % area |
| 0.45 | 0.05 | 0.45 | 0.06 | 0.45 | 0.05 | 0.45 | 0.05 | 0.45 | 0.06 |
| 0.97 | 0.18 | 0.97 | 0.17 | 0.97 | 0.19 | 0.97 | 0.18 | 0.97 | 0.19 |
| 1.00 | 99.6 | 1.00 | 99.6 | 1.00 | 99.5 | 1.00 | 99.5 | 1.00 | 99.5 |
| 1.14 | 0.13 | 1.13 | 0.05 | 1.14 | 0.07 | 1.13 | 0.07 | 1.13 | 0.06 |
| — | — | — | — | — | — | — | — | 1.25 | 0.05 |
| — | — | — | — | — | — | — | — | 1.40 | 0.05 |

The front running peak at RRT 0.97 under using Method 3 was subsequently identified as (beta-Asp10) abaloparatide, whose characterization will be described in detail later. Given the surprising and beneficial separation conferred by the use of a phosphate buffer in the mobile phase, it was decided to take a detailed look at the relative performance of HPLC vs UPLC using first, non-buffered mobile phase (Example 3) and buffered.

Example 3

Comparison of Methods 1 and 2 in Purifying Abaloparatide Samples

Figure 11A:
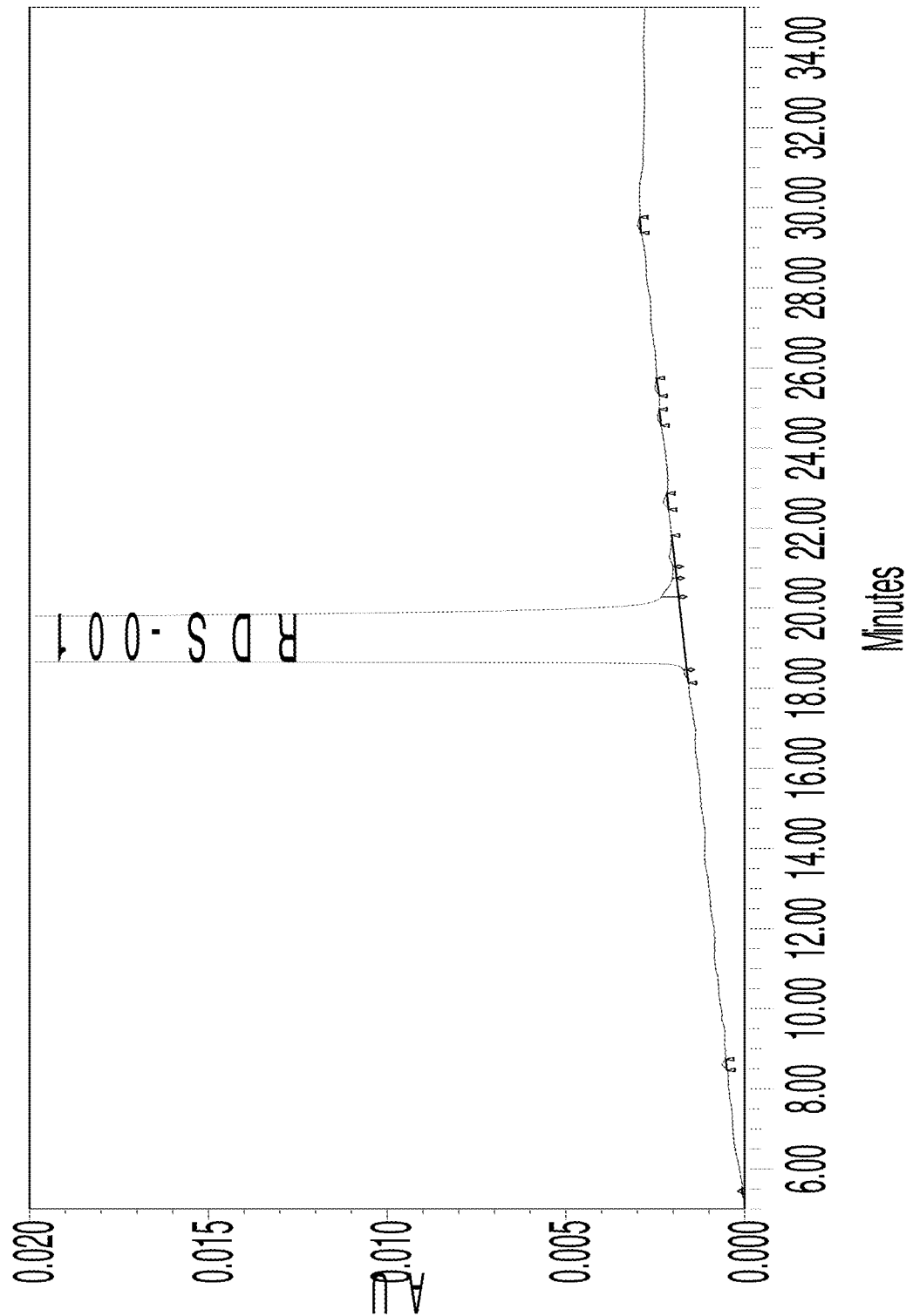
FIGS. 11A-11B: Testing of API sample 8AK1 by Methods 1 and 2.
Figure 11B:
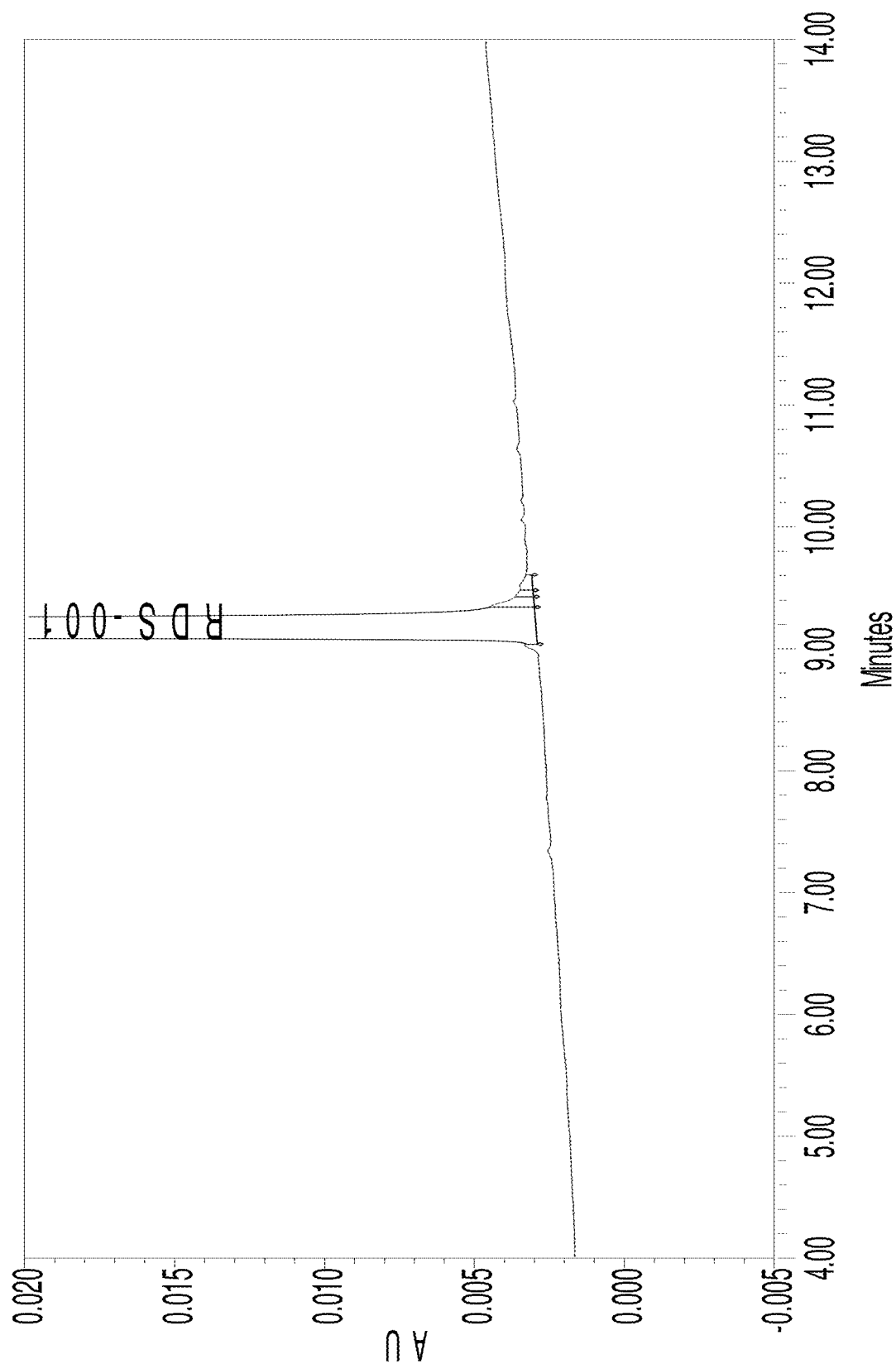

Method 2 (UPLC, no buffer) was compared to Method 1 (HPLC, no buffer) on an API sample manufactured in 2012 ("8AK1"). The results are juxtaposed in FIG. 11A and FIG. 11B.

Several batches were analysed using Method 1 and Method 2 and the impurity profiles have been compared (as shown for 1 batch in Table 8 below). The impact on the impurity profiles was acceptable regarding the comparison between HPLC and UPLC results for Methods 1 and 2, the results from UPLC version provided at least the same level of quality and furthermore provide better resolution of impurities and API main peak.

TABLE 8

| Abaloparatide API batches | | |
|---|---|---|
| Batch | Nature | Year of production |
| 4AI1 | API | 2010 |
| 4AI2 | API | 2010 |
| 4AI1R | RS | 2010 |

TABLE 7

Formulated drug product batch analysis by Method 3. Purity areas and relative retention times ("RRT"; abaloparatide = 1)

| BEJH09 a | | BEJH09 b | | BEJJ12 a | | BEJJ12 b | | BEJH09 c | |
|---|---|---|---|---|---|---|---|---|---|
| RRT | % area | RRT | % area | RRT | % area | RRT | % area | RRT | % area |
| 0.17 | 0.12 | 0.17 | 0.06 | 0.17 | 0.08 | 0.17 | 0.08 | 0.17 | 0.09 |
| 0.65 | 0.07 | 0.63 | 0.07 | 0.64 | 0.07 | 0.64 | 0.06 | 0.65 | 0.07 |
| 0.73 | 0.09 | 0.72 | 0.08 | 0.73 | 0.08 | 0.73 | 0.08 | 0.73 | 0.09 |
| — | — | 0.83 | 0.06 | — | — | — | — | 0.84 | 0.05 |
| — | — | 0.89 | 0.05 | — | — | — | — | — | — |
| 0.92 | 0.13 | 0.91 | 0.15 | 0.91 | 0.14 | 0.91 | 0.13 | 0.92 | 0.14 |
| 0.94 | 0.16 | 0.94 | 0.18 | 0.94 | 0.17 | 0.94 | 0.17 | 0.94 | 0.15 |
| 0.97 | 3.08 | 0.97 | 3.16 | 0.97 | 3.06 | 0.97 | 3.05 | 0.97 | 3.15 |
| 1.00 | 95.1 | 1.00 | 94.9 | 1.00 | 95.2 | 1.00 | 95.2 | 1.00 | 95.0 |
| 1.07 | 0.78 | 1.08 | 0.81 | 1.07 | 0.66 | 1.07 | 0.71 | 1.07 | 0.87 |
| 1.11 | 0.17 | 1.12 | 0.09 | 1.10 | 0.15 | 1.10 | 0.16 | 1.15 | 0.13 |
| — | — | 1.15 | 0.15 | 1.15 | 0.08 | 1.15 | 0.09 | — | — |
| — | — | 1.17 | 0.06 | — | — | — | — | — | — |
| 1.29 | 0.15 | 1.30 | 0.11 | 1.29 | 0.17 | 1.29 | 0.15 | 1.29 | 0.14 |

TABLE 8-continued

Abaloparatide API batches

| Batch | Nature | Year of production |
|---|---|---|
| 3AJ1 | API | 2011 |
| 8AK1 | API | 2012 |
| 8AK1R | RS | 2012 |
| 3AL1 | API | 2013 |
| 7AL1 | API | 2013 |
| 10AL1 | API | 2013 |
| 10AL2 | API | 2013 |

TABLE 9

Impurity profiles according to Method 1

% area Method 1-TFA - HPLC

| RRT | 4AI1 | 4AI2 | 4AI1R | 3AJ1 | 8AK1R | 8AK1 | 3AL1 | 7AL1 | 10AL1 | 10AL2 |
|---|---|---|---|---|---|---|---|---|---|---|
| 0.82 | — | — | — | — | — | — | 0.07 | — | — | — |
| 1.00 | 99.74 | 99.51 | 99.52 | 99.86 | 99.73 | 99.77 | 99.79 | 99.94 | 99.70 | 99.89 |
| 1.07-1.08 | — | 0.15 | 0.18 | 0.10 | 0.08 | 0.09 | 0.08 | — | 0.20 | — |
| 1.11-1.13 | 0.10 | 0.13 | 0.15 | — | 0.06 | — | — | — | — | 0.11 |
| 1.15 | — | — | — | — | — | — | — | — | 0.10 | — |
| 1.31 | — | 0.09 | 0.08 | — | — | — | — | — | — | — |

TABLE 10

Impurity profiles according to Method 2

% area Method 2-TFA - UPLC

| RRT | 4AI1 | 4AI2 | 4AI1R | 3AJ1 | 8AK1R | 8AK1 | 3AL1 | 7AL1 | 10AL1 | 10AL2 |
|---|---|---|---|---|---|---|---|---|---|---|
| 0.94 | — | — | — | 0.05 | — | — | 0.10 | — | — | — |
| 0.99 | — | — | — | — | — | — | — | — | 0.06 | 0.05 |
| 1.00 | 99.07 | 99.12 | 99.23 | 99.50 | 99.72 | 99.63 | 99.30 | 99.51 | 99.15 | 99.50 |
| 1.02-1.03 | 0.37 | 0.42 | 0.34 | 0.29 | 0.22 | 0.21 | 0.30 | 0.29 | 0.52 | 0.27 |
| 1.03 | 0.11 | 0.13 | 0.12 | 0.10 | — | 0.06 | 0.11 | 0.09 | 0.08 | 0.12 |
| 1.04 | 0.16 | 0.17 | 0.13 | 0.06 | 0.06 | 0.10 | 0.19 | 0.11 | 0.13 | 0.05 |
| 1.05 | — | — | 0.06 | — | — | — | — | — | — | — |
| 1.06 | — | — | 0.08 | — | — | — | — | — | — | — |
| 1.07 | 0.10 | 0.08 | 0.05 | — | — | — | — | — | — | — |
| 1.09-1.10 | 0.07 | 0.07 | — | — | — | — | — | — | 0.06 | — |
| 1.12 | 0.06 | — | — | — | — | — | — | — | — | — |
| 1.16 | 0.06 | — | — | — | — | — | — | — | — | — |

Injected volume: 5 μl
Sample concentration: 5 μg/5 μl H₂O
Truncated Peptides

Figure 12A:
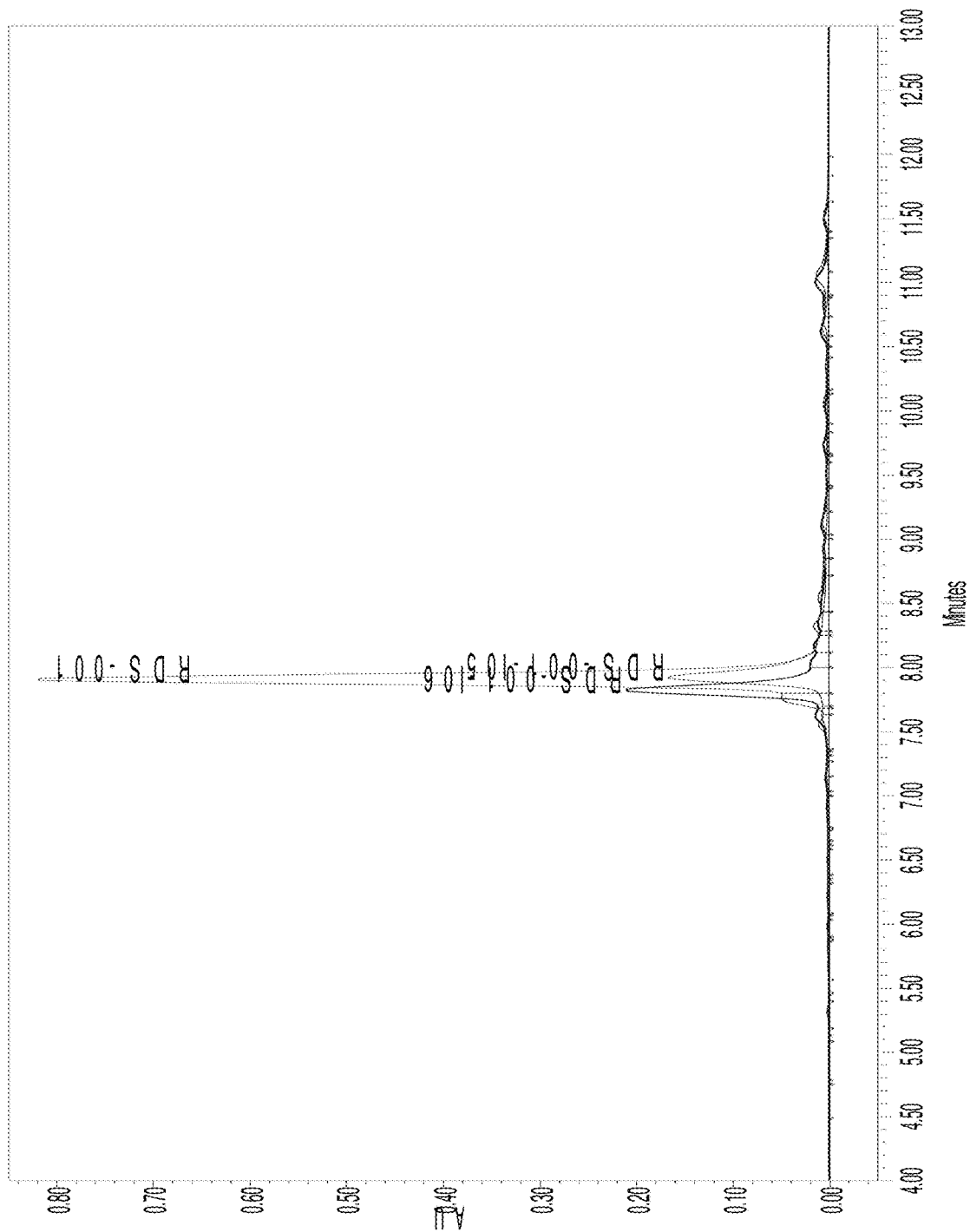
FIGS. 12A-12U: Optimization of Method 4.
Figure 12B:
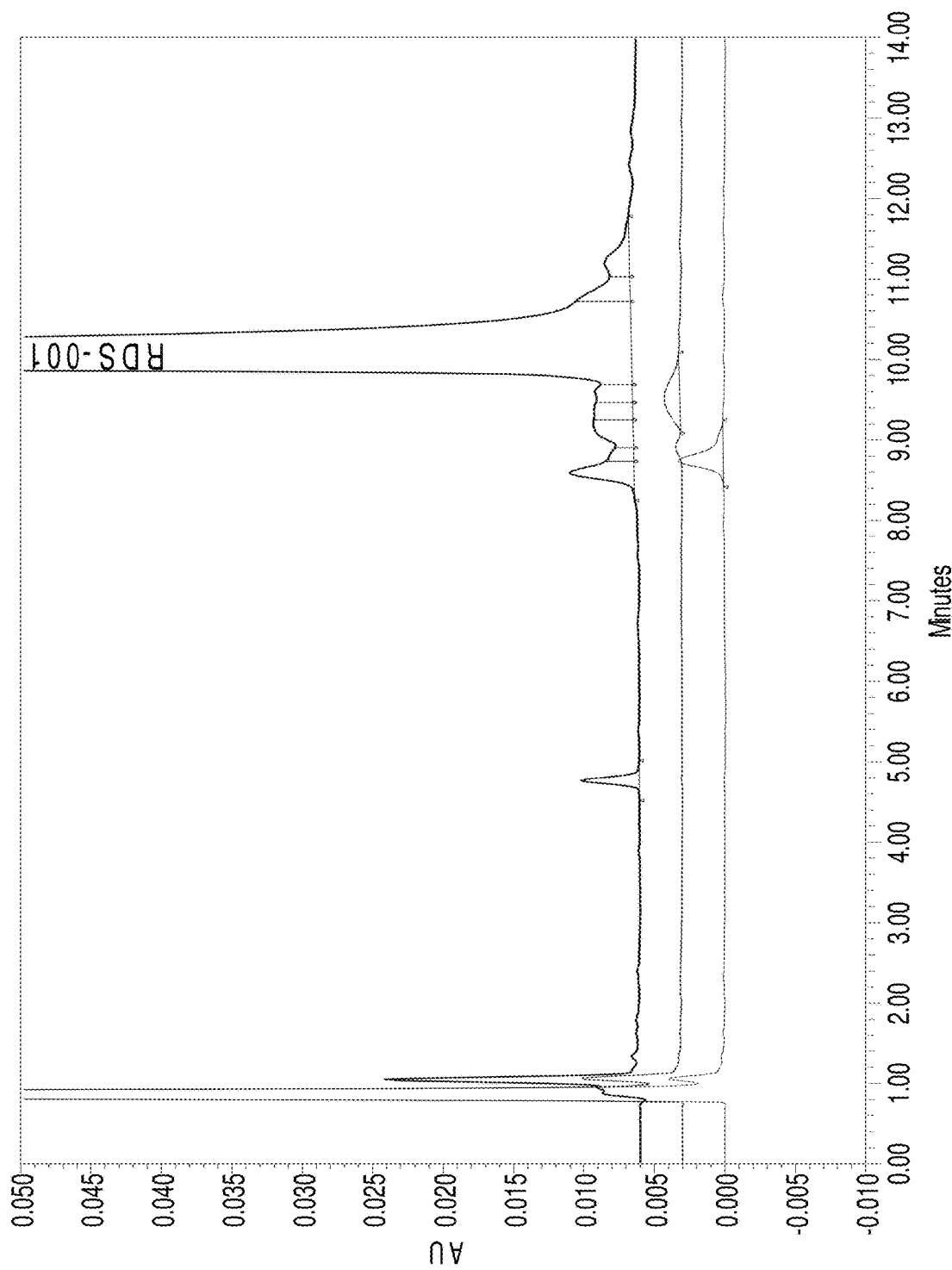
(FIG. 12B) Truncated peptides by phosphate/C18. Resolved but peak broadened abaloparatide and ATP (3-34) and ATP (4-34).
Figure 12C:
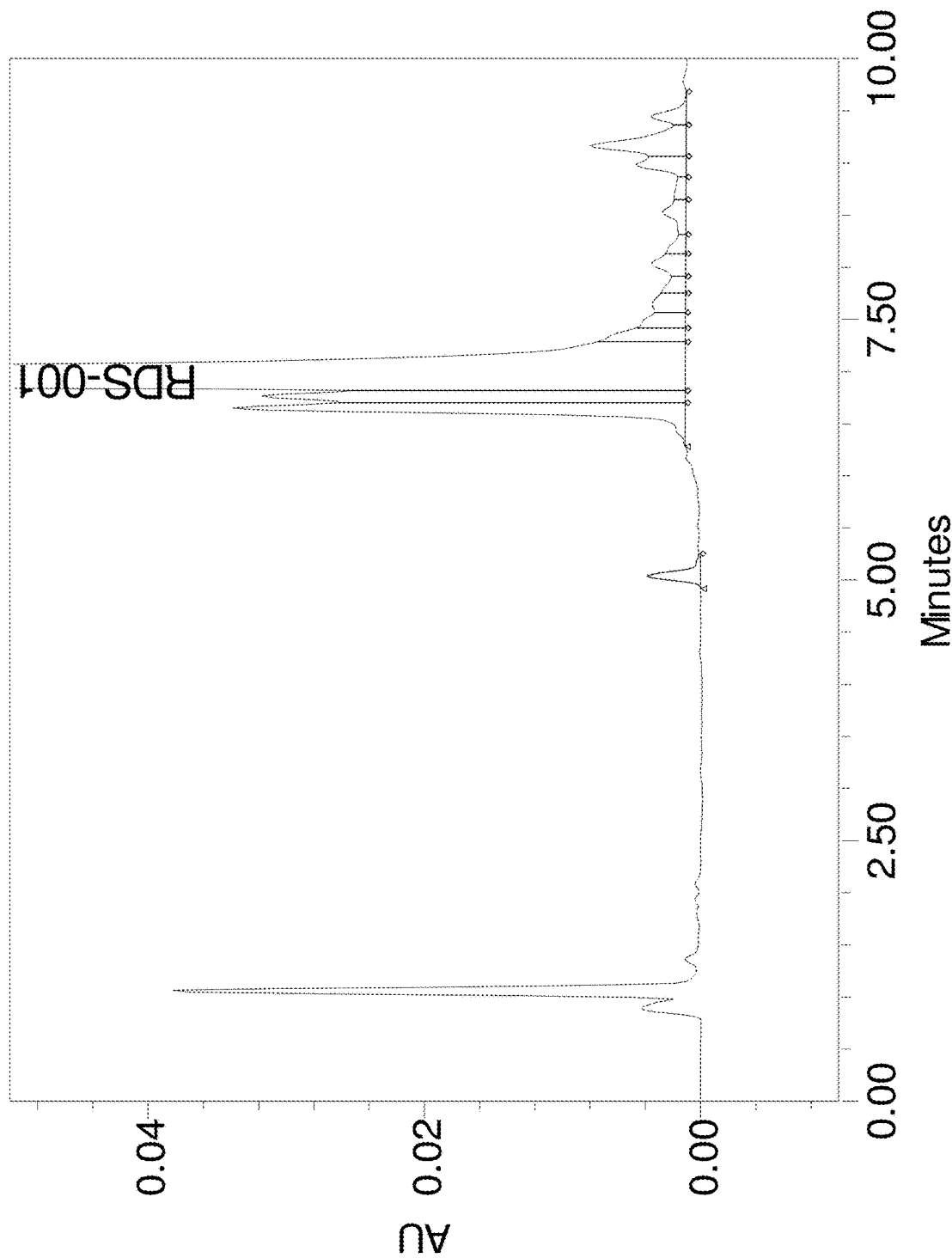
(FIG. 12C)+55° C.
Figure 12D:
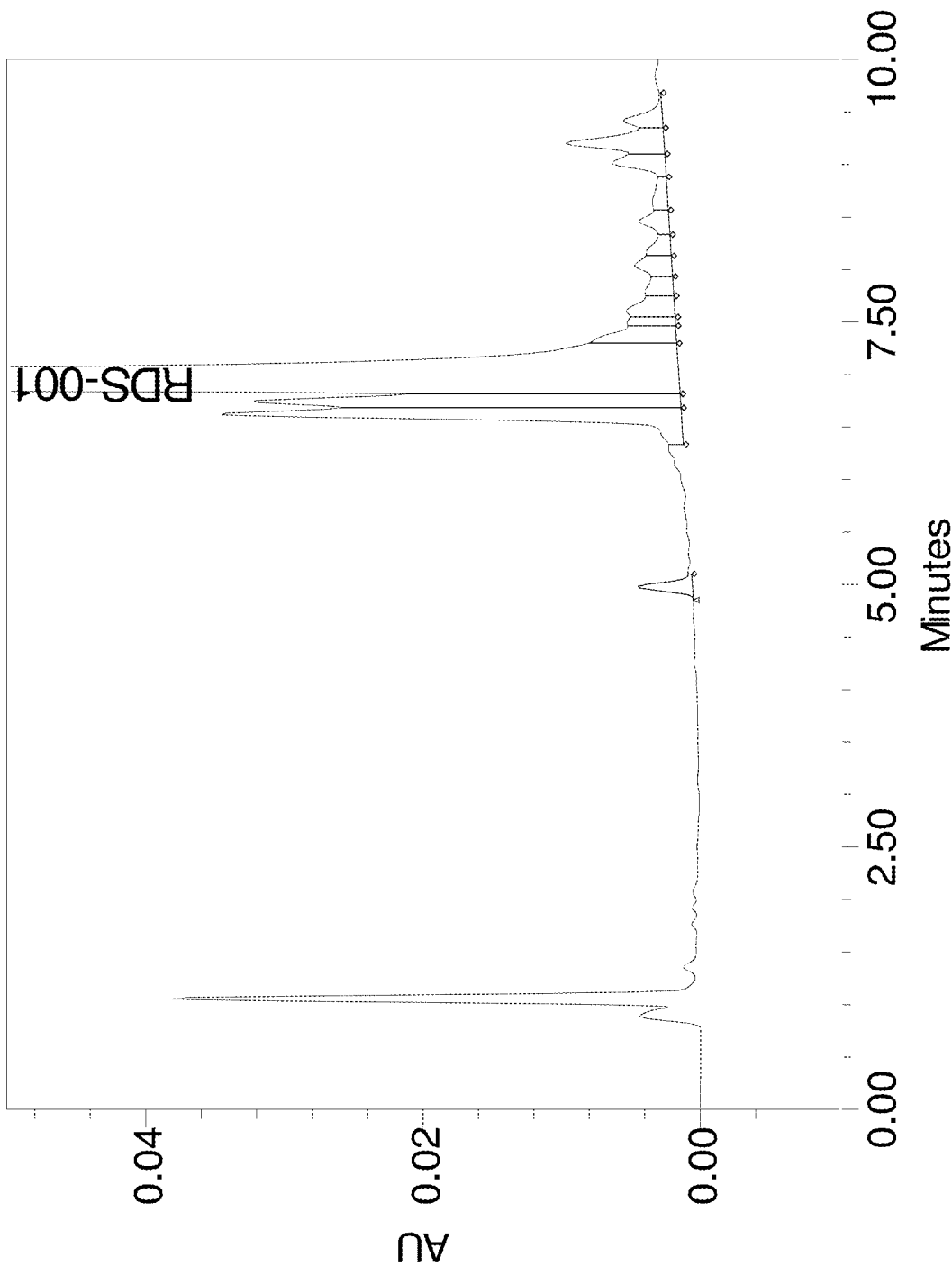
(FIG. 12D)+60° C.
Figure 12E:
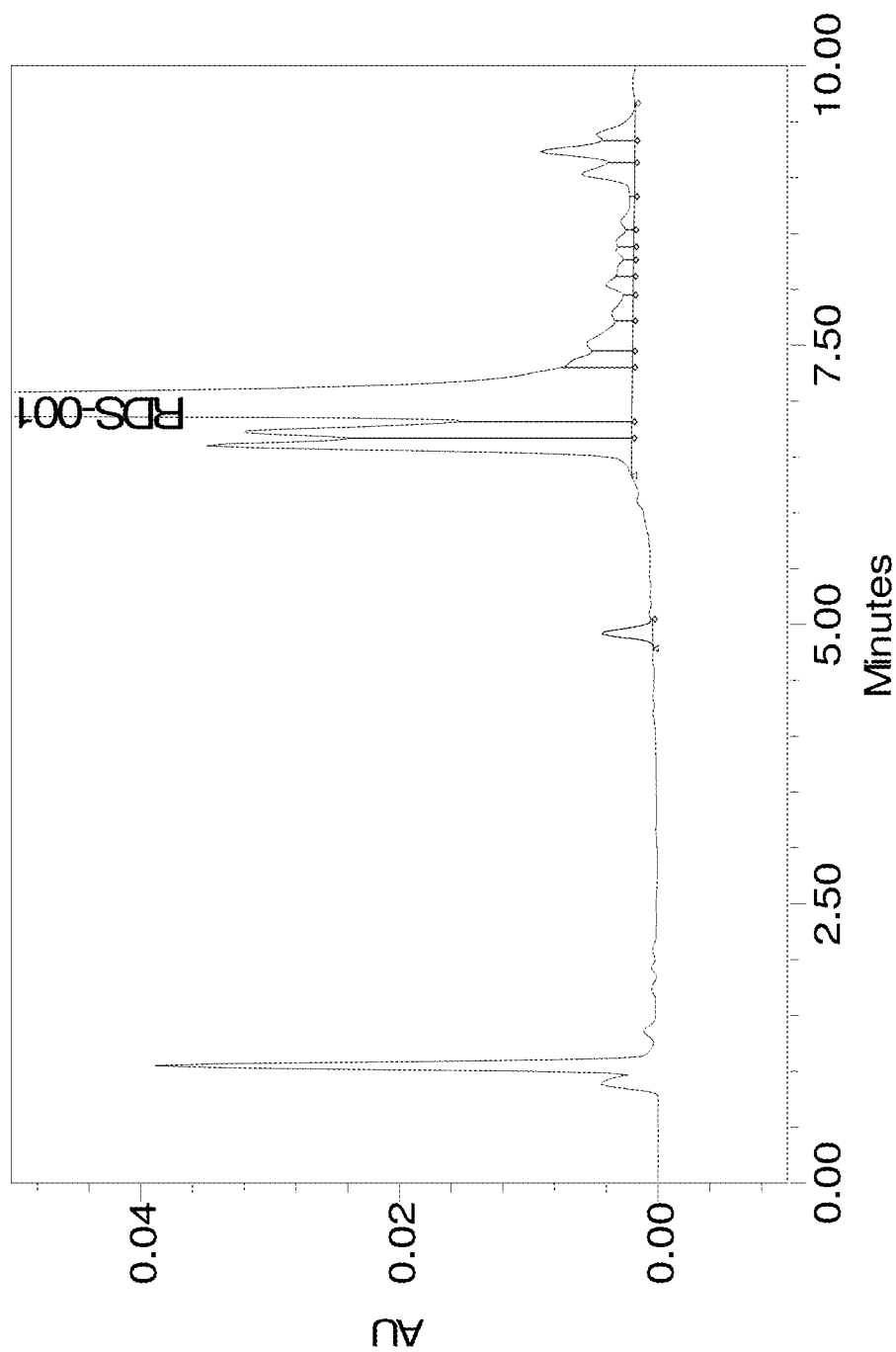
(FIG. 12E)+65° C.
Figure 12F:
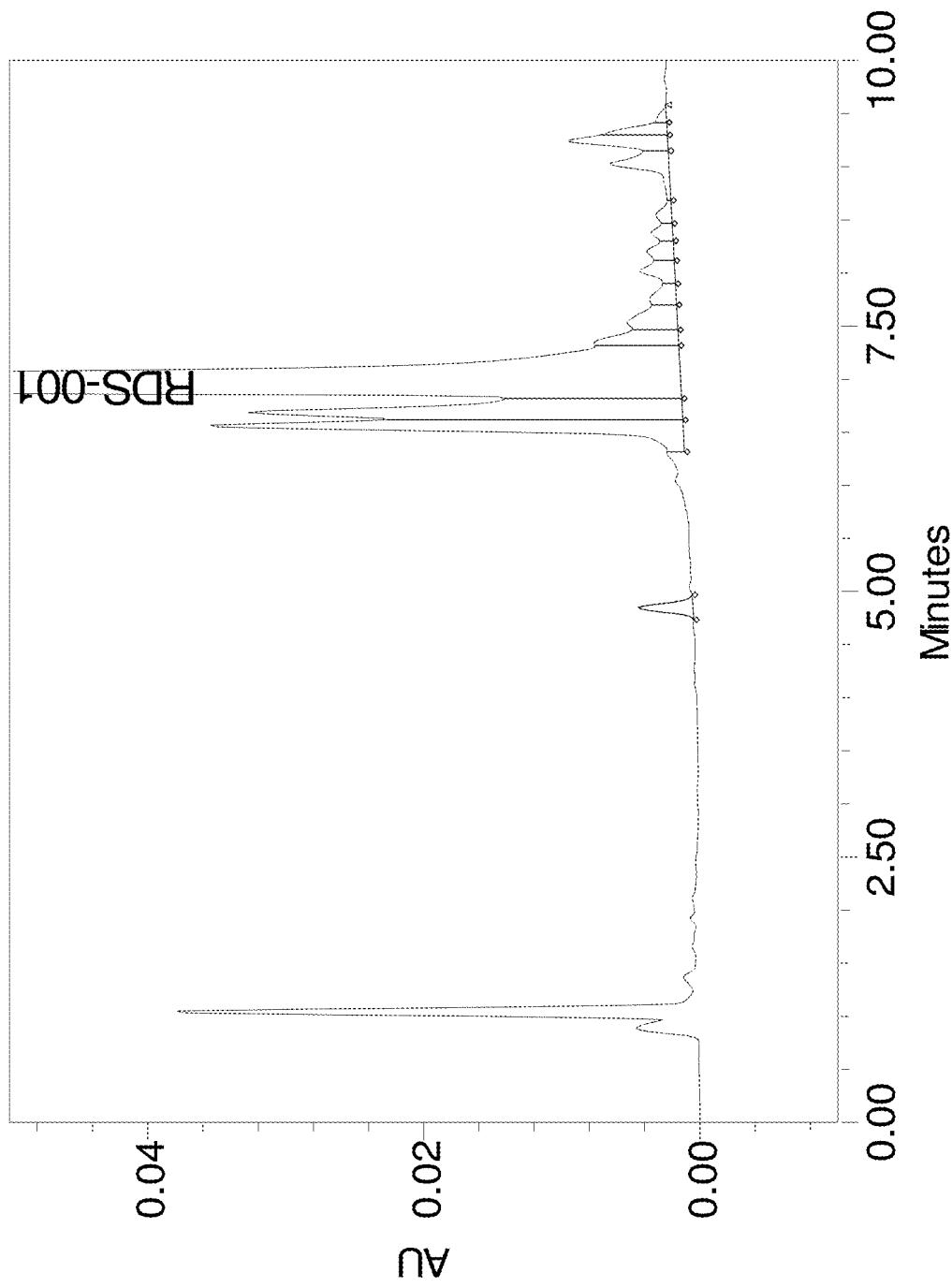
(FIG. 12F)+70° C.
Figure 12G:
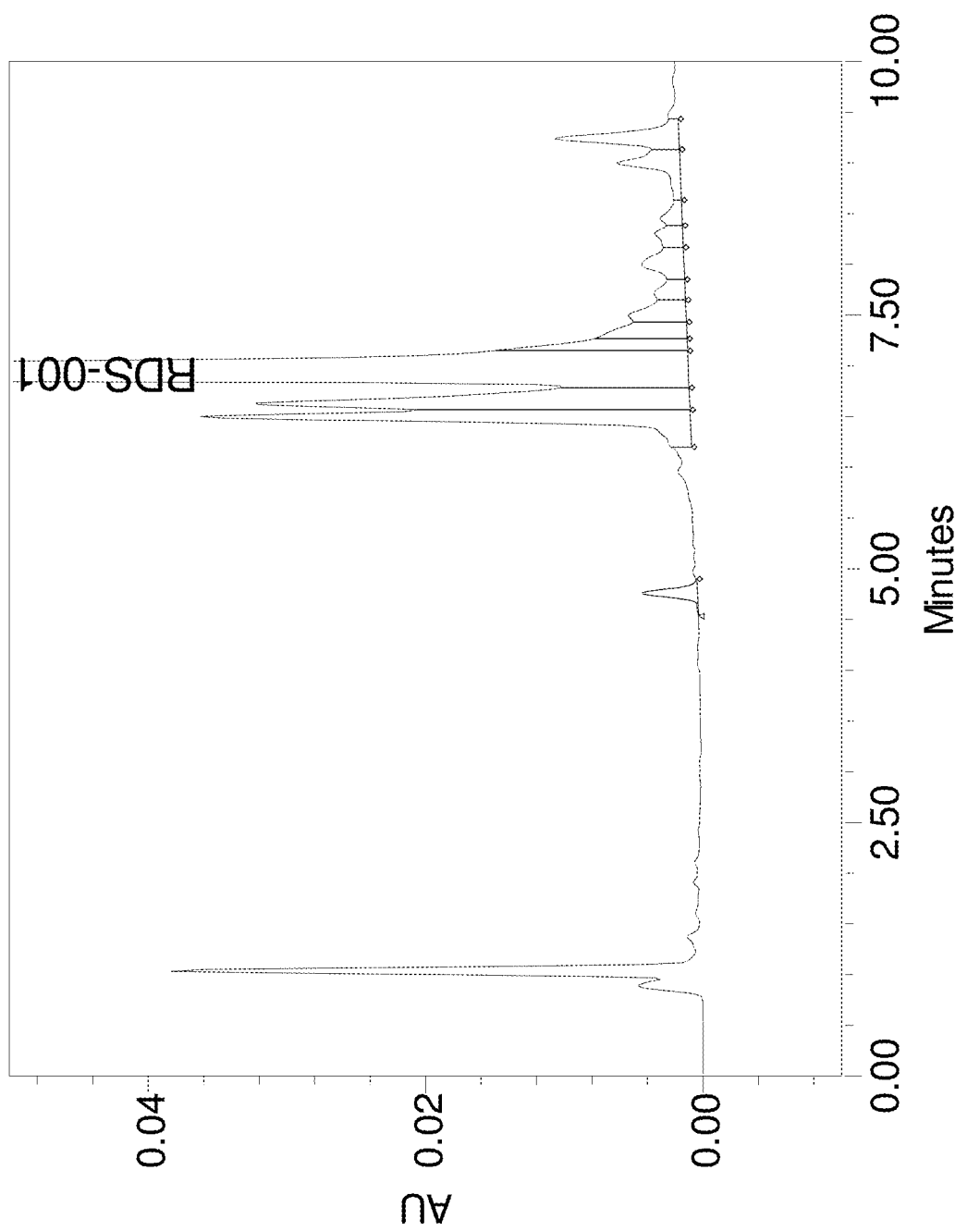
(FIG. 12G)+75° C.
Figure 12H:
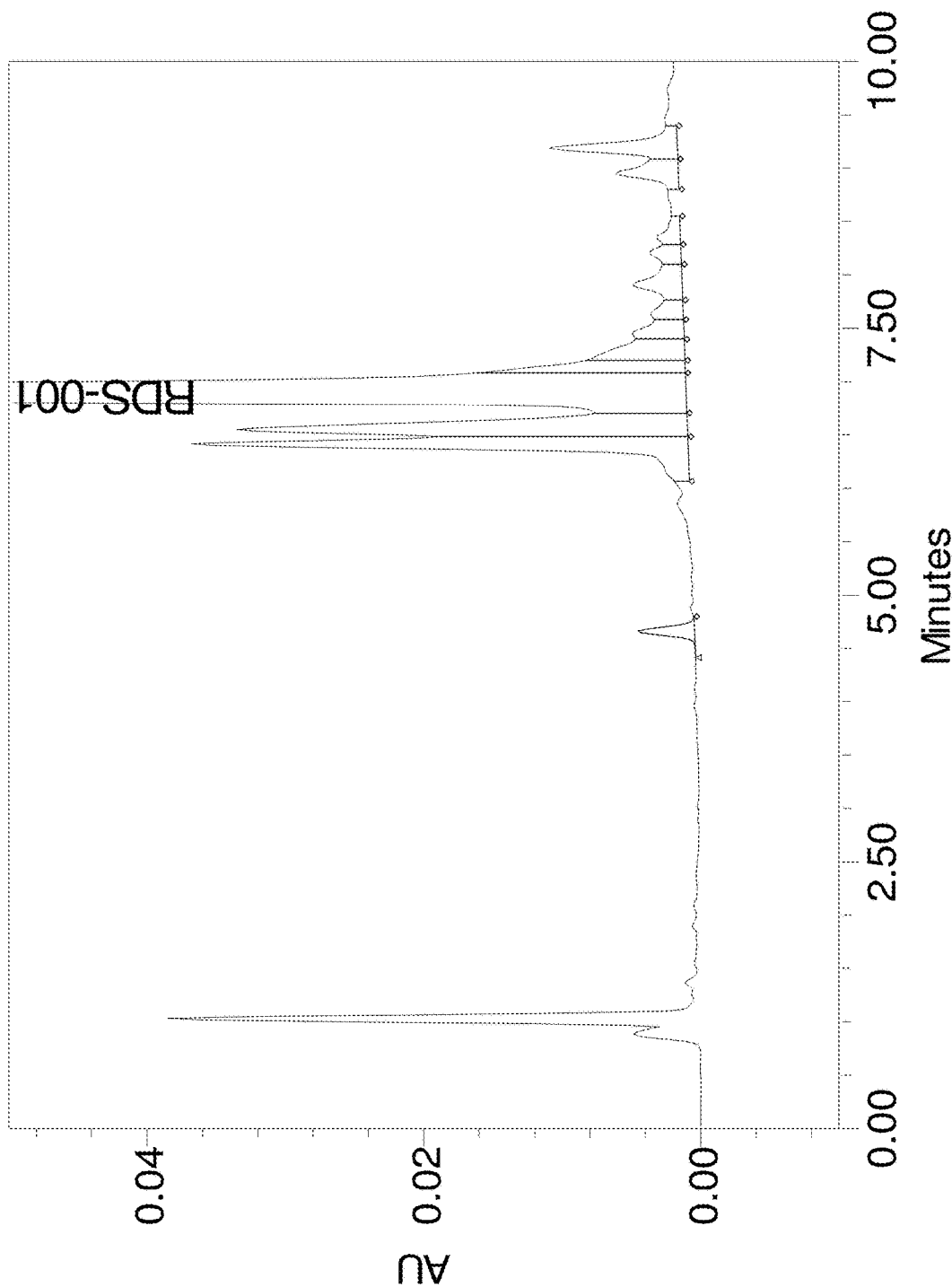
(FIG. 12H)+80° C.
Figure 12I:
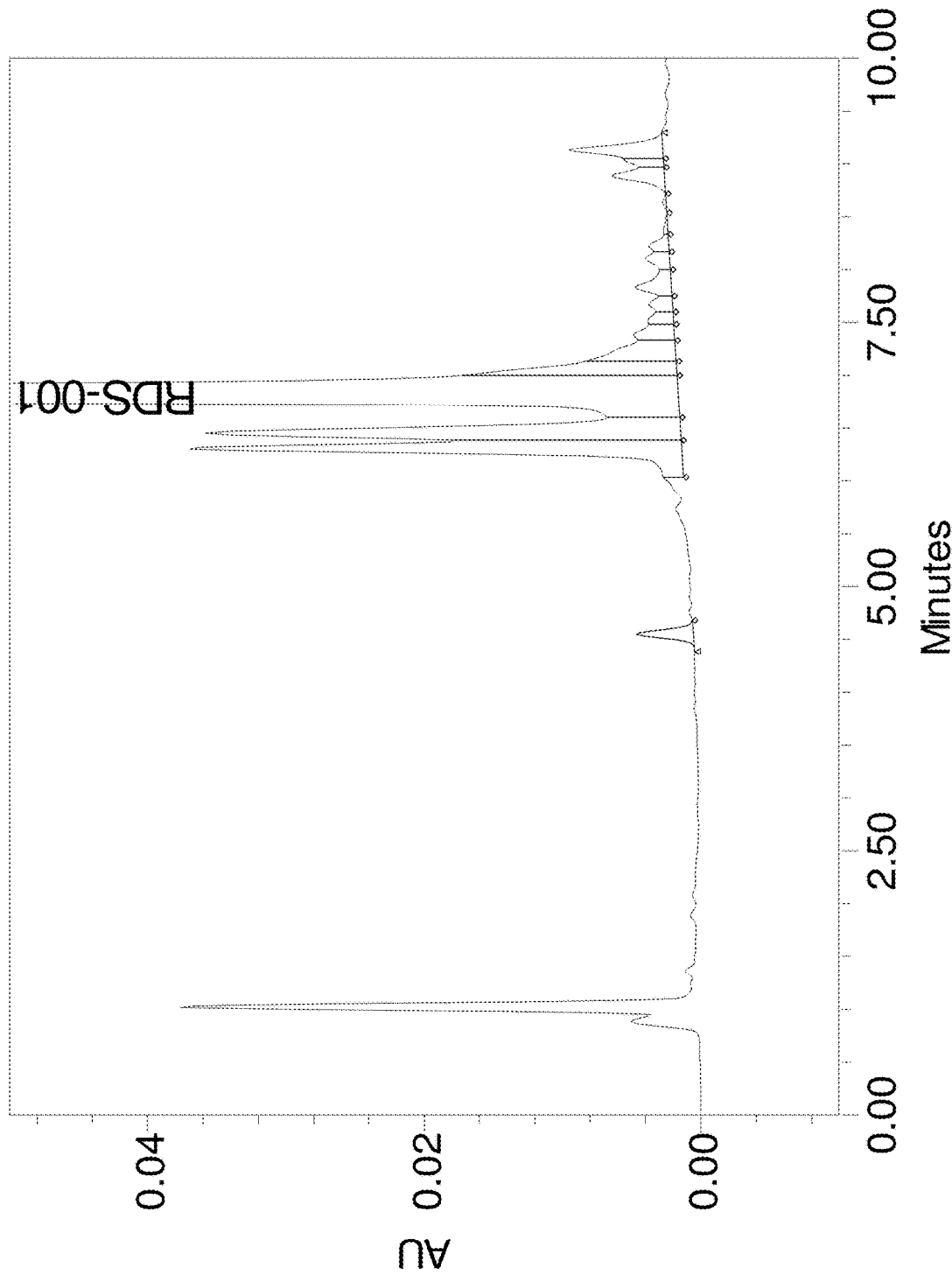
(FIG. 12I)+85° C.
Figure 12J:
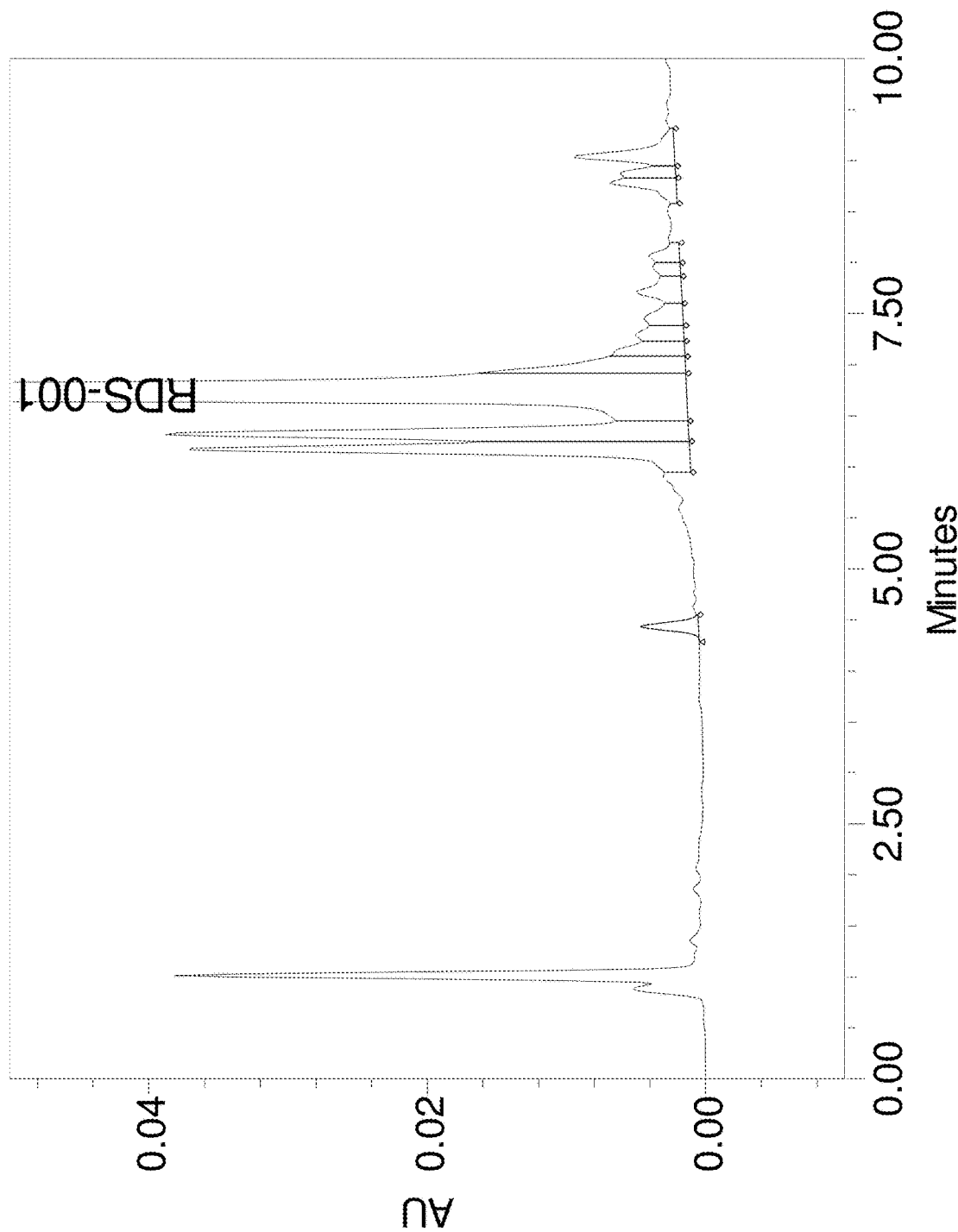
(FIG. 12J)+90° C.

The RDS-001-I06 impurity peak were eluted before the abaloparatide (RDS-001) peak, but the RDS001-I05 impurity peak has the same retention time then the abaloparatide peak (see FIG. 12A). With a faster gradient, the impurities remained under the peak. With an isocratic elution at 50% mobile phase B, the 2 impurities peaks were eluted before the abaloparatide (RDS-001) peak but the RDS-001-I05 peak shape was wide (see FIG. 12B).

Example 4

Development/Optimization of Method 4 in Purifying Abaloparatide Samples Evaluation of Gradient on C18 Column Different gradient systems were tested to assess the best gradient condition to discriminate the truncated peptides (RDS-001-I05 and RDS-001-I06).
Analytical Conditions—UPLC
Columns: UPLC Acquity BEH C18 1,7μ 150*2.1 mm
Mobile phase A: 64 mM $(NH_4)_2HPO_4$ in $H_2O$ pH 7.8
Mobile phase B: (56 mM $(NH_4)_2HPO_4$ pH 7.8 in $H_2O$/ACN 50/50
Flow rate: 400 μl/min
Detection: 220 nm
Gradient: 37% B 1'-37-61% B in 10'
Column temperature: 60° C.
Sample temperature: 10° C.

Figure 12K:
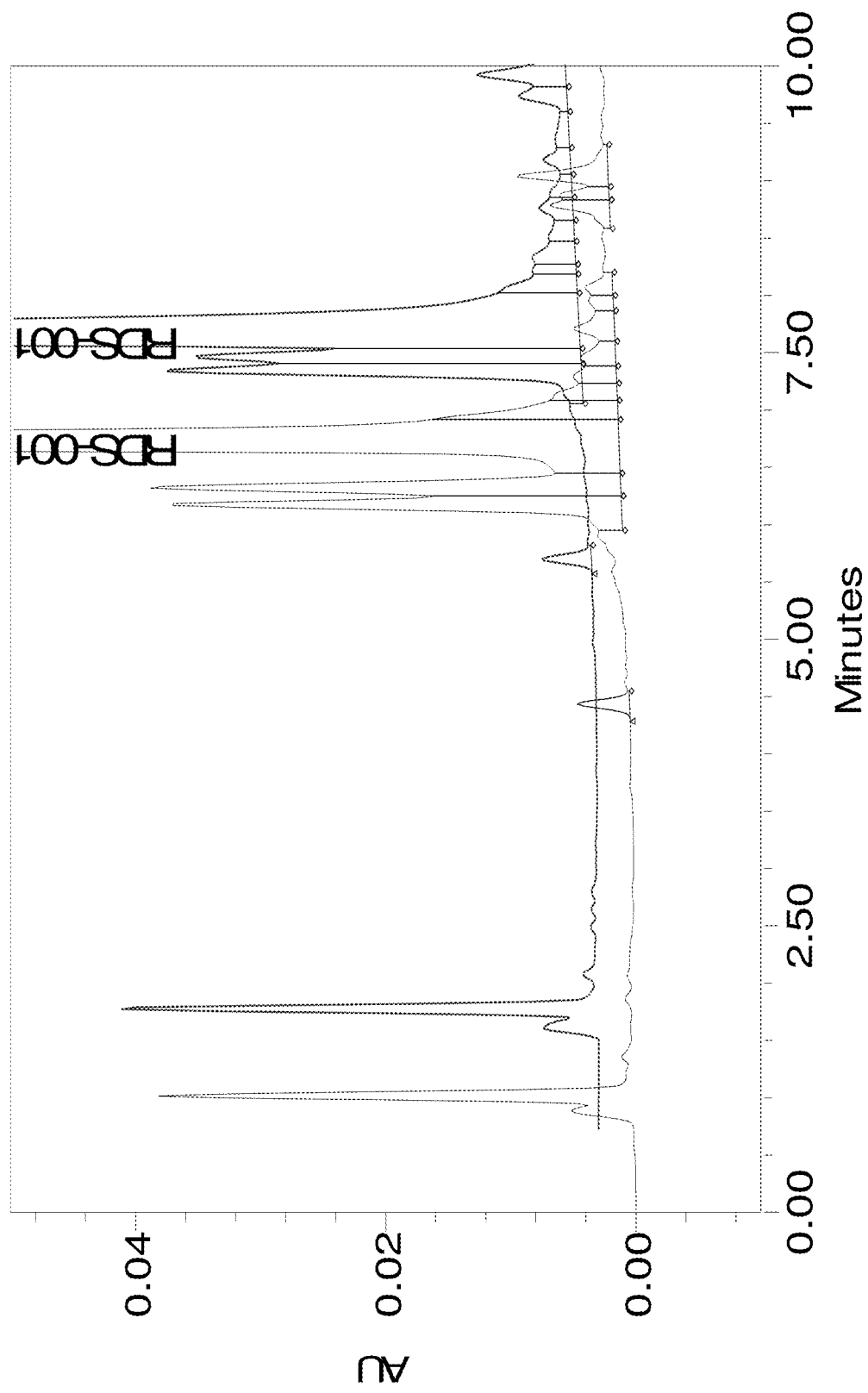
(FIG. 12K) Overlay +55° C. (red) and +90° C. (black).

To avoid crystallizing problems in the B phase, 40% of acetonitrile was prepared instead of the 50%. The isocratic elution was changed to 60% B.
Evaluation of Column Temperature Different column temperatures were tested to assess the best gradient condition to discriminate the truncated peptides (RDS-001-I05 and RDS-001-I06).
Truncated Peptides Impact of the column temperature was tested from 40° C. to 90° C. The 2 peaks began to be separated from main peak at +55° C. and this separation improved until +90° C. Results for each temperature are shown in FIG. 12C-12J, and an overlay of the results for +55° C. and +90° C. is shown in FIG. 12K.
Further Exploration of Conditions Using C18 Column
Analytical Conditions
Columns: UPLC Acquity BEH C18 1,7μ 150*2.1 mm
Mobile phase A: 64 mM $(NH_4)_2HPO_4/H_2O$ pH 7.8
Mobile phase B: (58% 160 mM $(NH_4)_2HPO_4/H_2O$ pH 7.8, 42% $H_2O$)/ACN 60/40

Figure 12L:
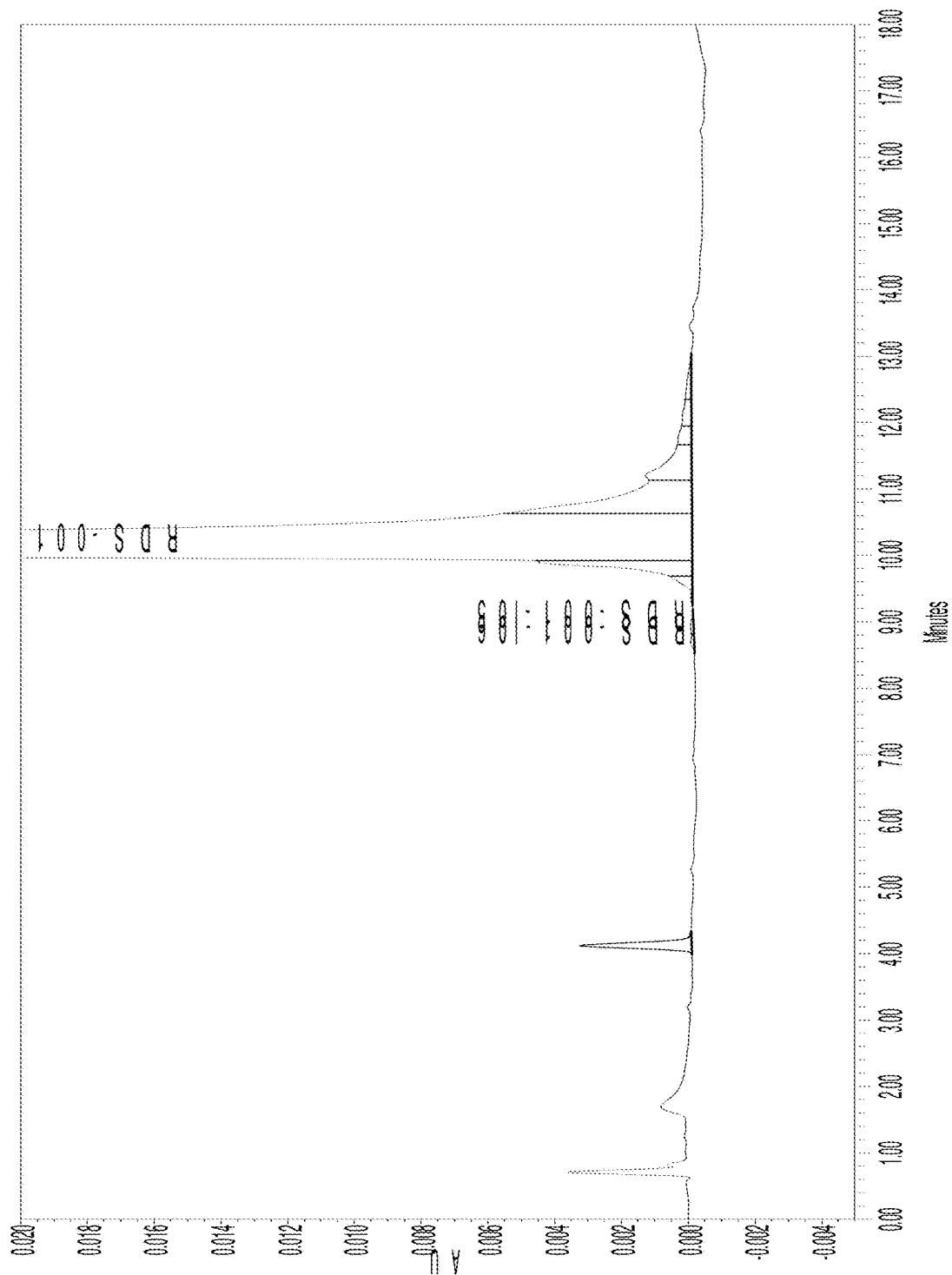
(FIG. 12L) Optimization of C18 conditions.

Flow rate: 0.5 ml/min
Detection: 220 nm
Gradient: 60% B -60-70% B in 15'
Column temperature: 90° C.
Sample temperature: 10° C.
Injected volume:
Sample concentration: 5 μg/5 μl H$_2$O
Truncated Peptides C18 column results are shown in FIG. 12L.

Figure 12M:
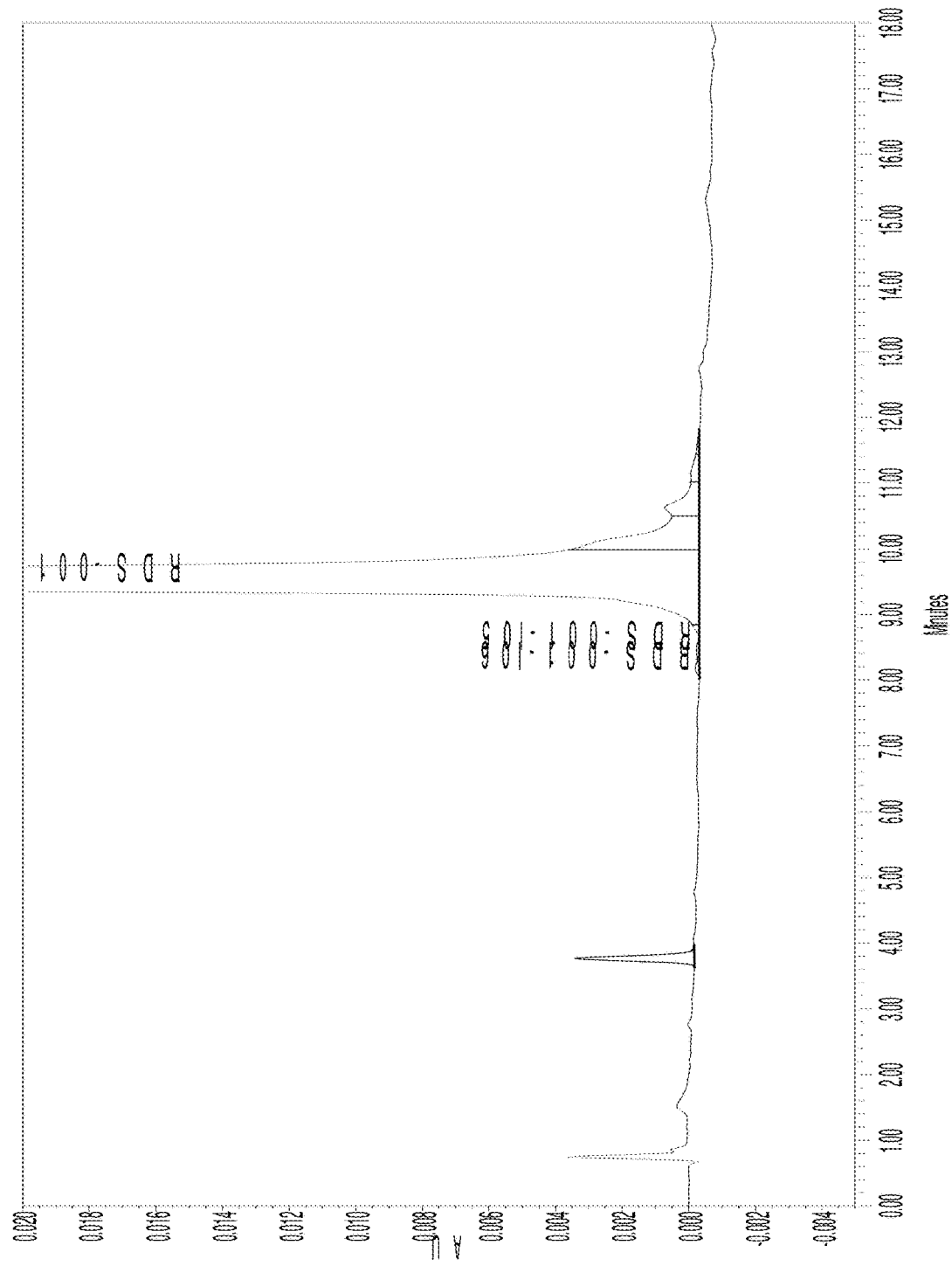
(FIG. 12M) Truncated peptides by Method 4 using C8 column.
Figure 12N:
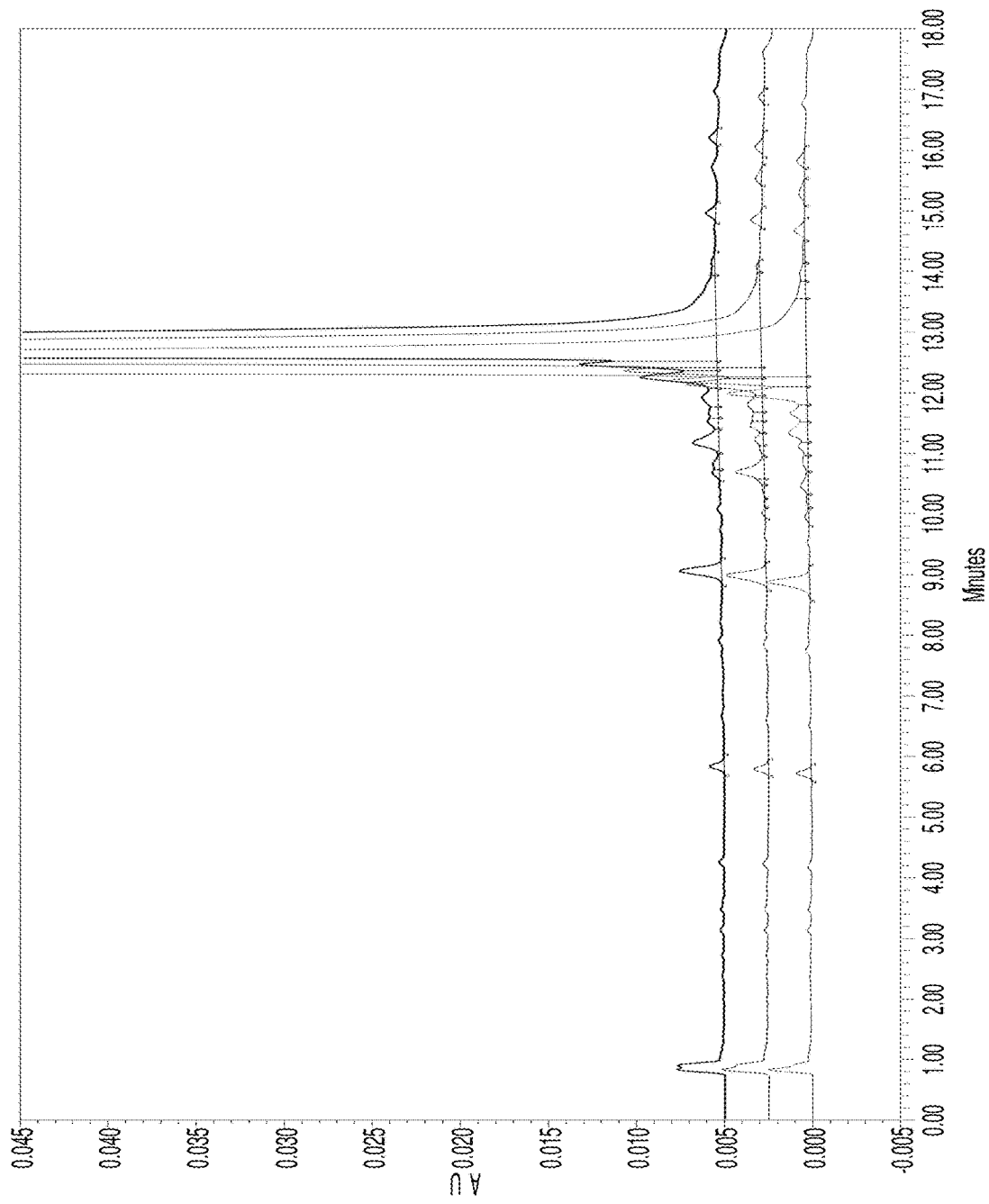
(FIG. 12N) Truncated peptides by phosphate/C4. Blue: Abaloparatide API spiked with RDS-001405. Red: Abaloparatide API spiked with RDS-001-I06. Black: Abaloparatide API unspiked.
Figure 12O:
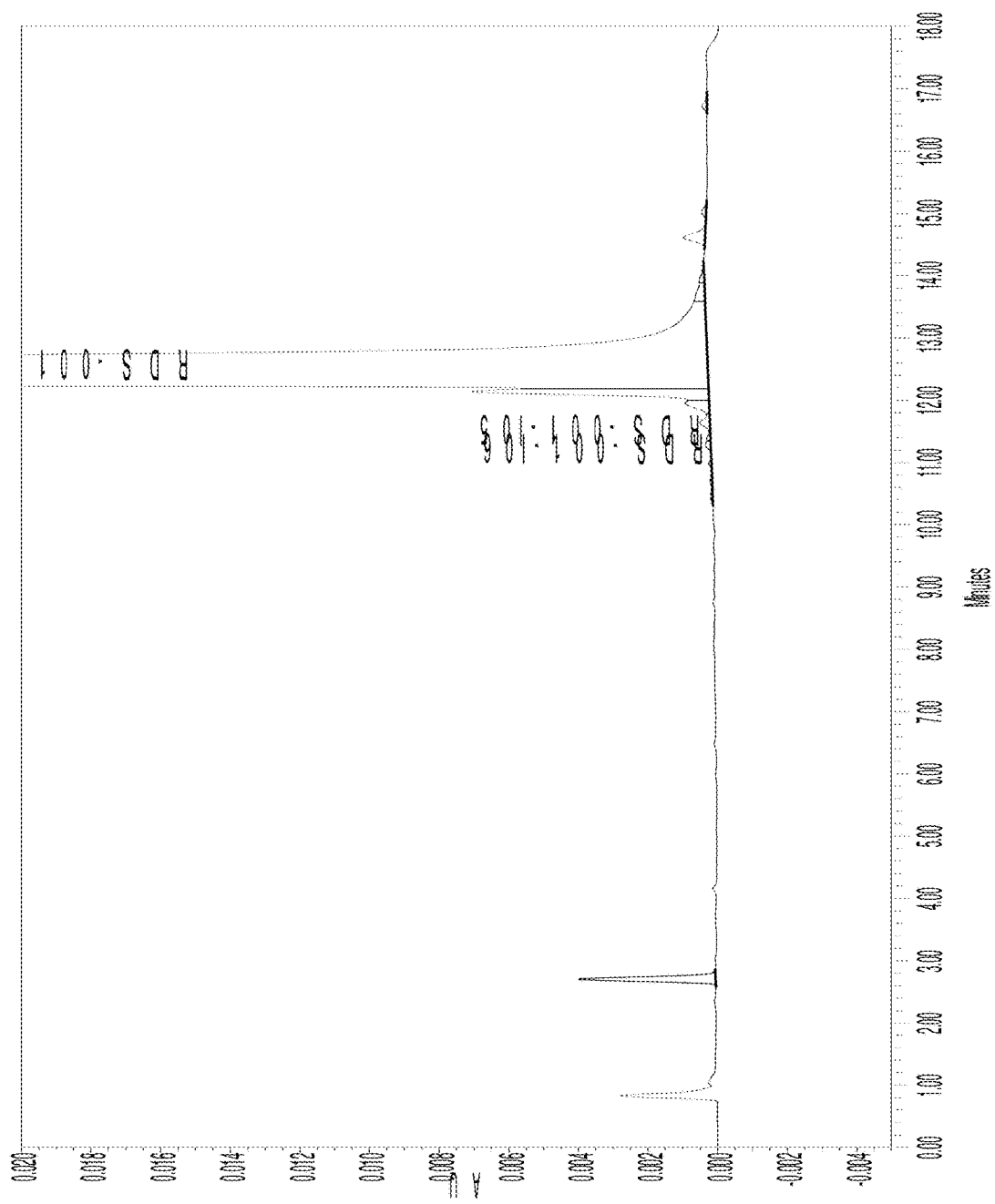
(FIG. 12O) UPLC phosphate/C4-8AG1.
Figure 12P:
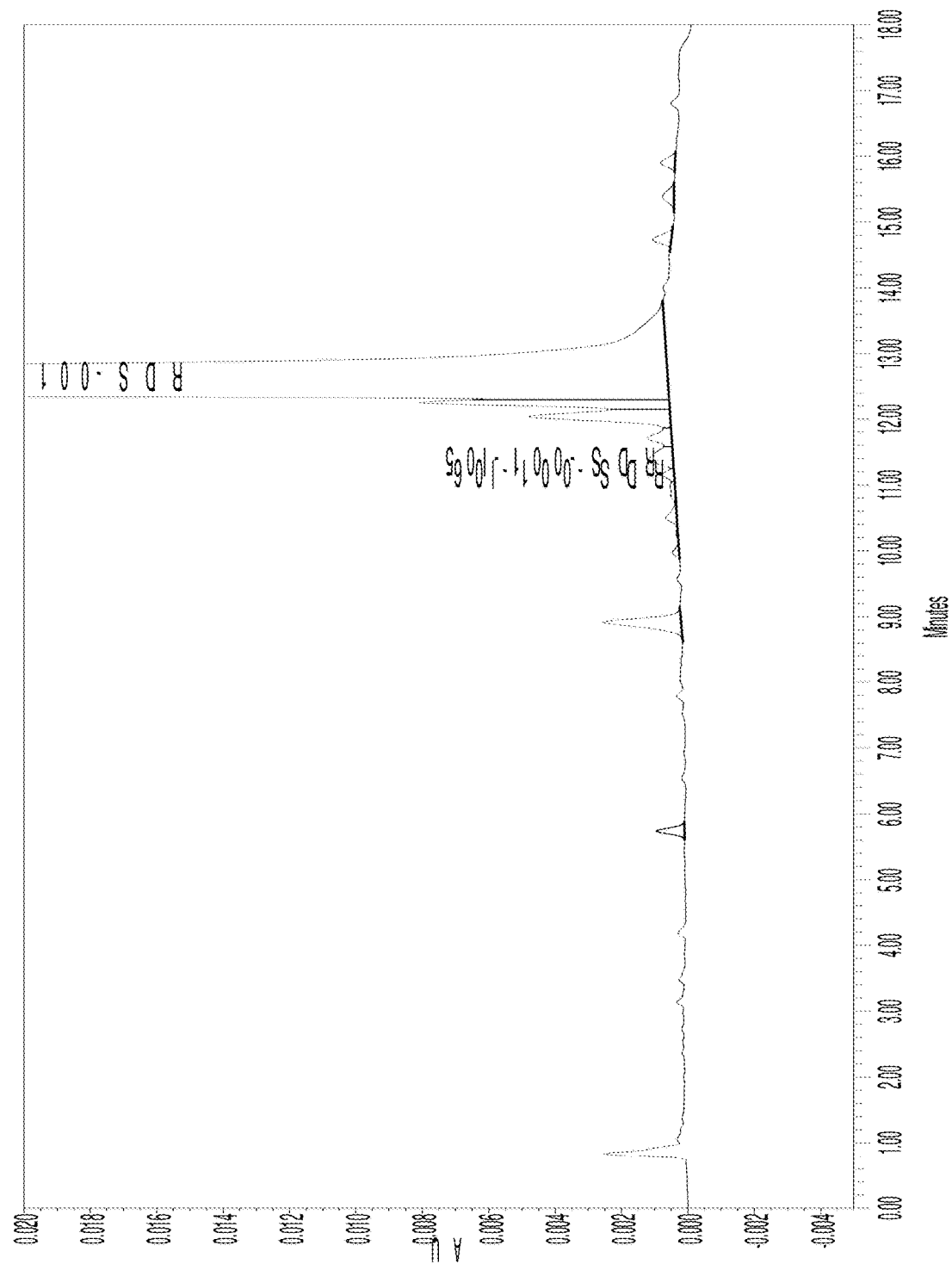
(FIG. 12P) UPLC phosphate/C4—6AG1R.
Figure 12Q:
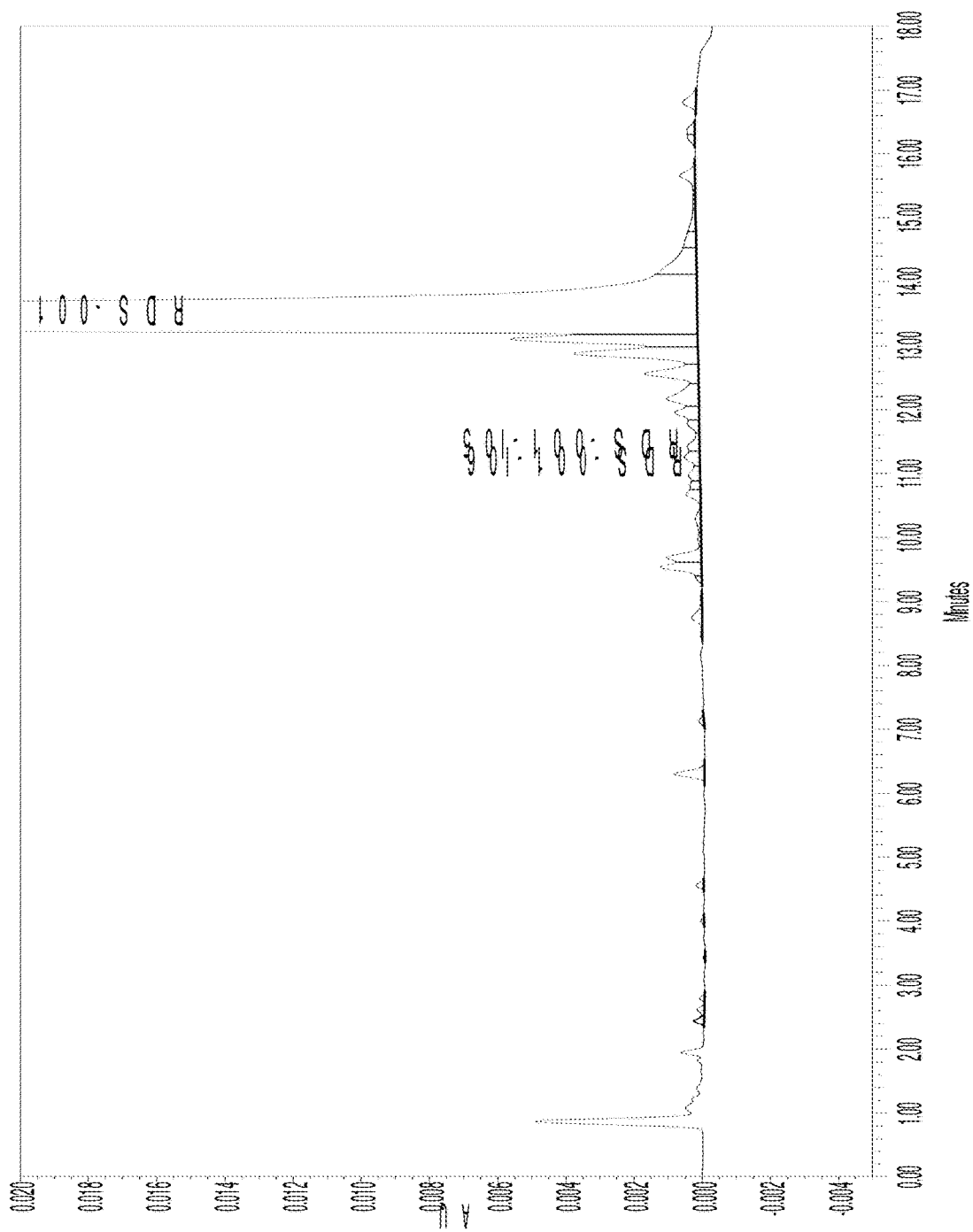
(FIG. 12Q) UPLC phosphate/C4—RDHAG112 Fp1 (representative IPC sample).
Figure 12R:
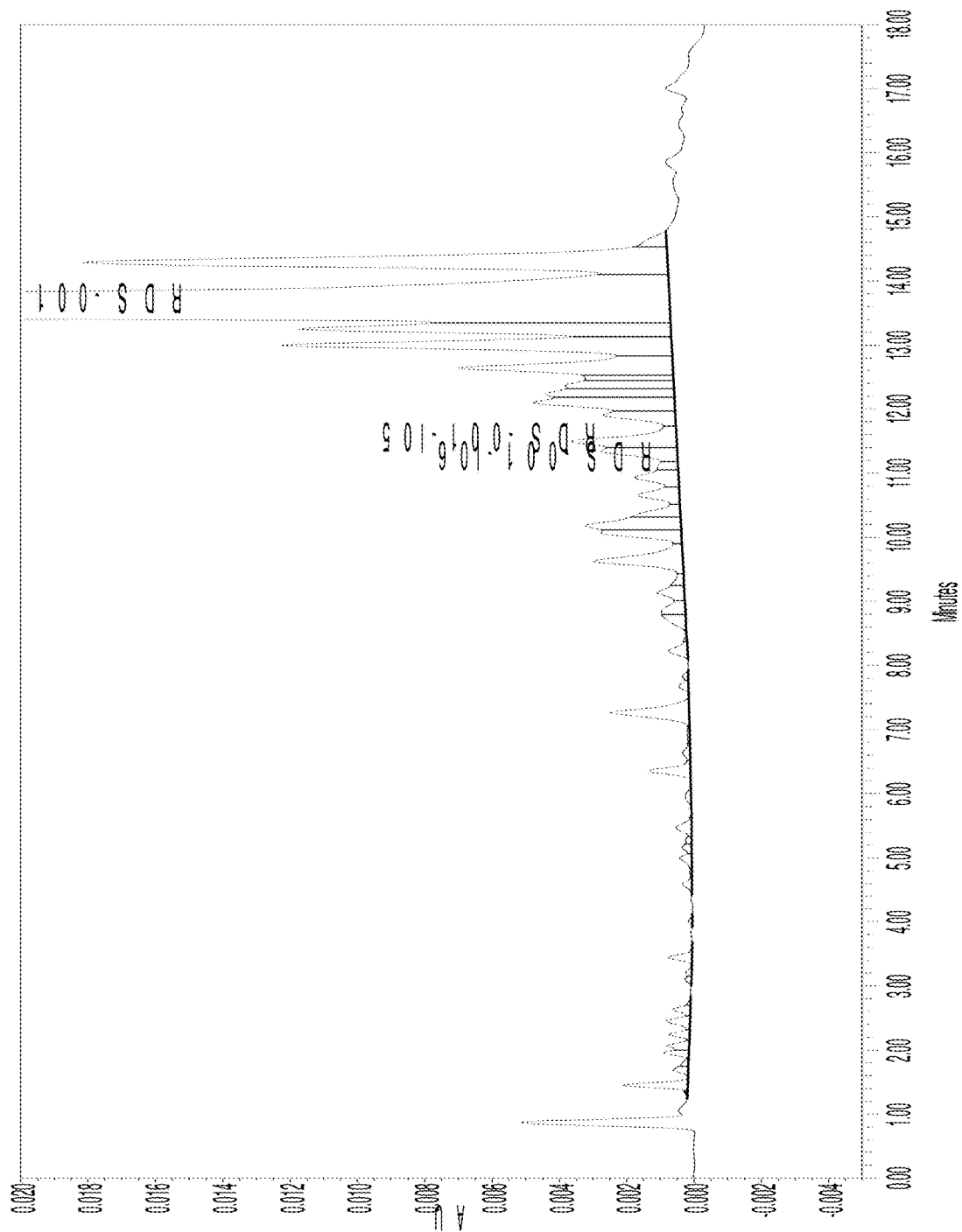
(FIG. 12R) UPLC phosphate/C4—RDHAG112 FpAv (representative IPC sample).

Truncated peptides were well separated from the main peak but columns C4 and C8 were evaluated in the hope that they might improve the discrimination in front peak and decrease the tailing. It was discovered that a C4 column substantially improved both front end discrimination and decreased tailing, particularly after further optimization.
Evaluation of C4 and C8 Columns
Analytical Conditions
Columns: UPLC Acquity BEH C8 1,7μ 150*2.1 mm
Mobile phase A: 64 mM (NH$_4$)$_2$HPO$_4$/H$_2$O pH 7.8
Mobile phase B: (58% 160 mM (NH$_4$)$_2$HPO$_4$/H$_2$O pH 7.8, 42% H$_2$O)/ACN 60/40
Flow rate: 0.5 ml/min
Detection: 220 nm
Gradient: 60%B - 60-70% B in 15'
Column temperature: 90° C.
Sample temperature: 10° C.
Injected volume: 5 μl
Sample concentration: 5 μg/5 μl H$_2$O
Truncated Peptides C8 column results are shown in FIG. 12M. The peak shape was not improved with C8 column.
Phosphate Solvent System Using UPLC/C4 Column
Analytical Conditions
Columns: UPLC Acquity BEH C4 1,7μ 150*2.1 mm
Mobile phase A: 64 mM (NH$_4$)$_2$HPO$_4$/H$_2$O pH 7.8
Mobile phase B: (58% 160 mM (NH$_4$)$_2$HPO$_4$/H$_2$O pH 7.8, 42% H$_2$O)/ACN 60/40
Flow rate: 0.5 ml/min
Detection: 220 nm
Gradient: 55% B - 55-65% B in 15'
Column temperature: 90° C.
Sample temperature: 10° C.
Injected volume: 5 μl
Sample concentration: 5 μg/5 μl H$_2$O FIG. 12N presents the overlay of 3 chromatograms:
Abaloparatide, API spiked with RDS-001-I05 (Blue)
Abaloparatide, API spiked with RDS-001-I06 (Red)
Abaloparatide, API unspiked (Black)

The impurities were better discriminated from the main peak using a C4 column compared to C18-UPLC method, and resolution of impurities in the tailing was better.
Sample Analyses (API and IPC)

Figure 12S:
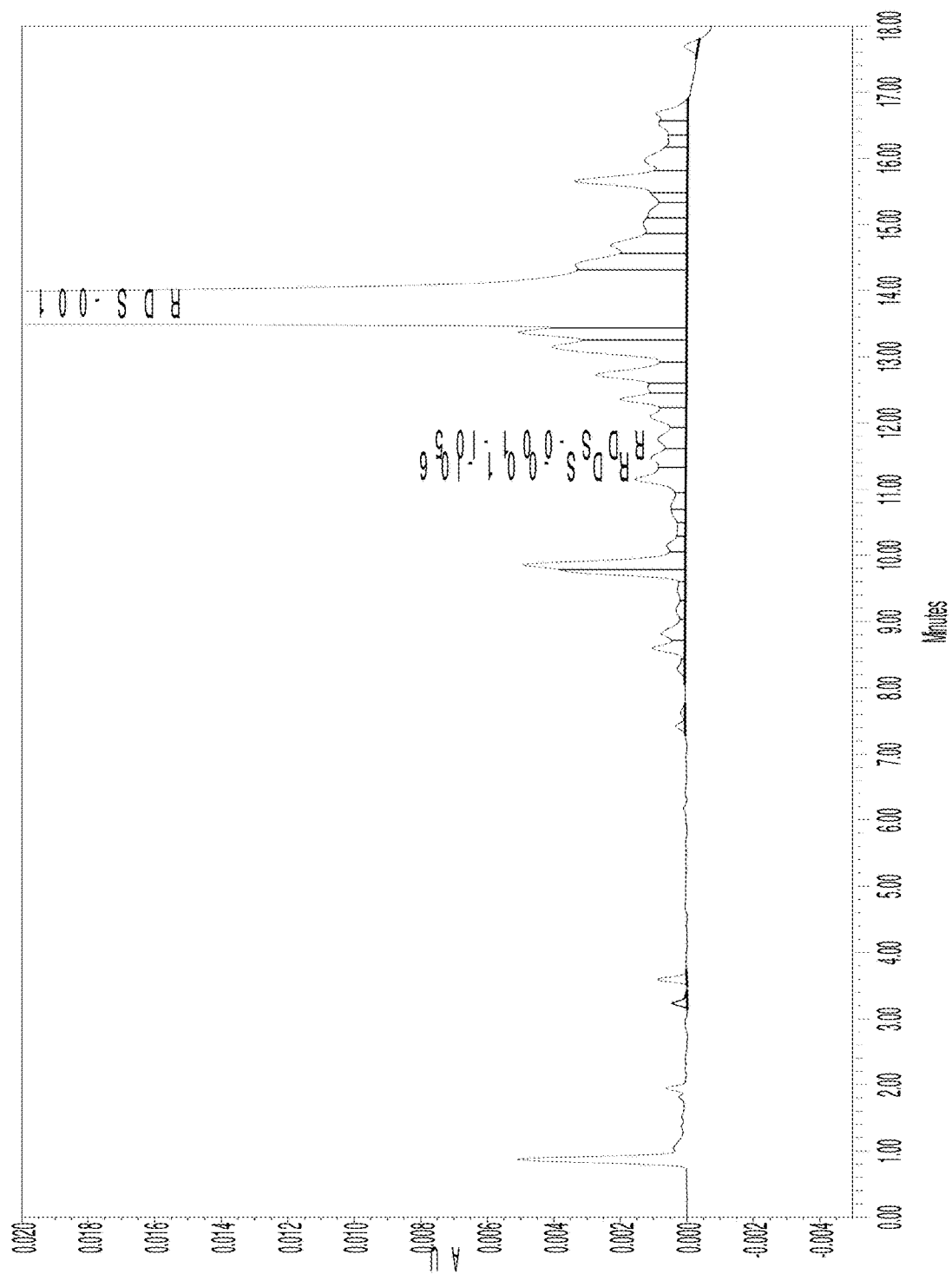
(FIG. 12S) UPLC phosphate/C4—RDHAG112 FpArr.
Figure 12T:
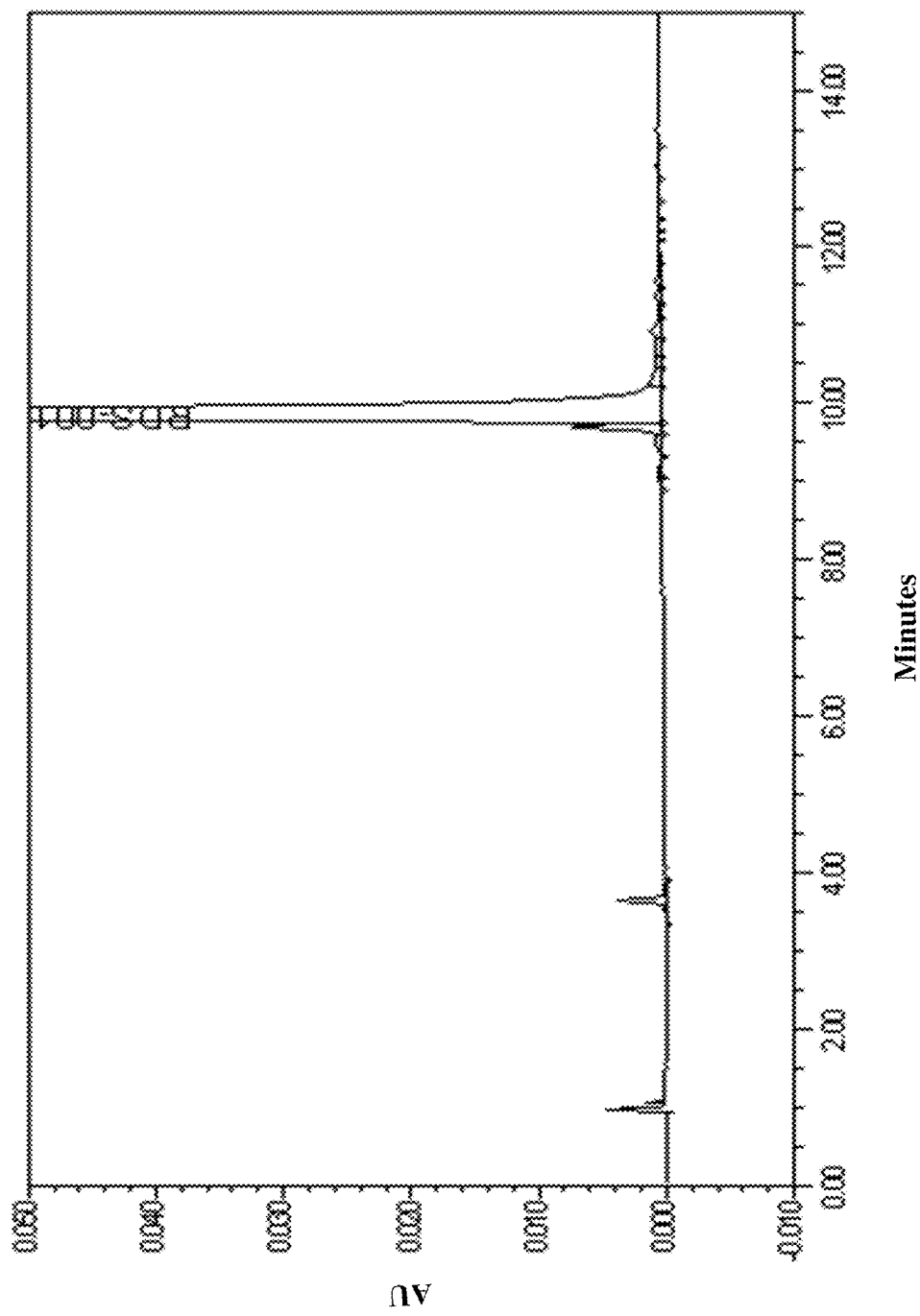
(FIG. 12T) Phosphate/C4—0.4 ml/min—8AG1.
Figure 12U:
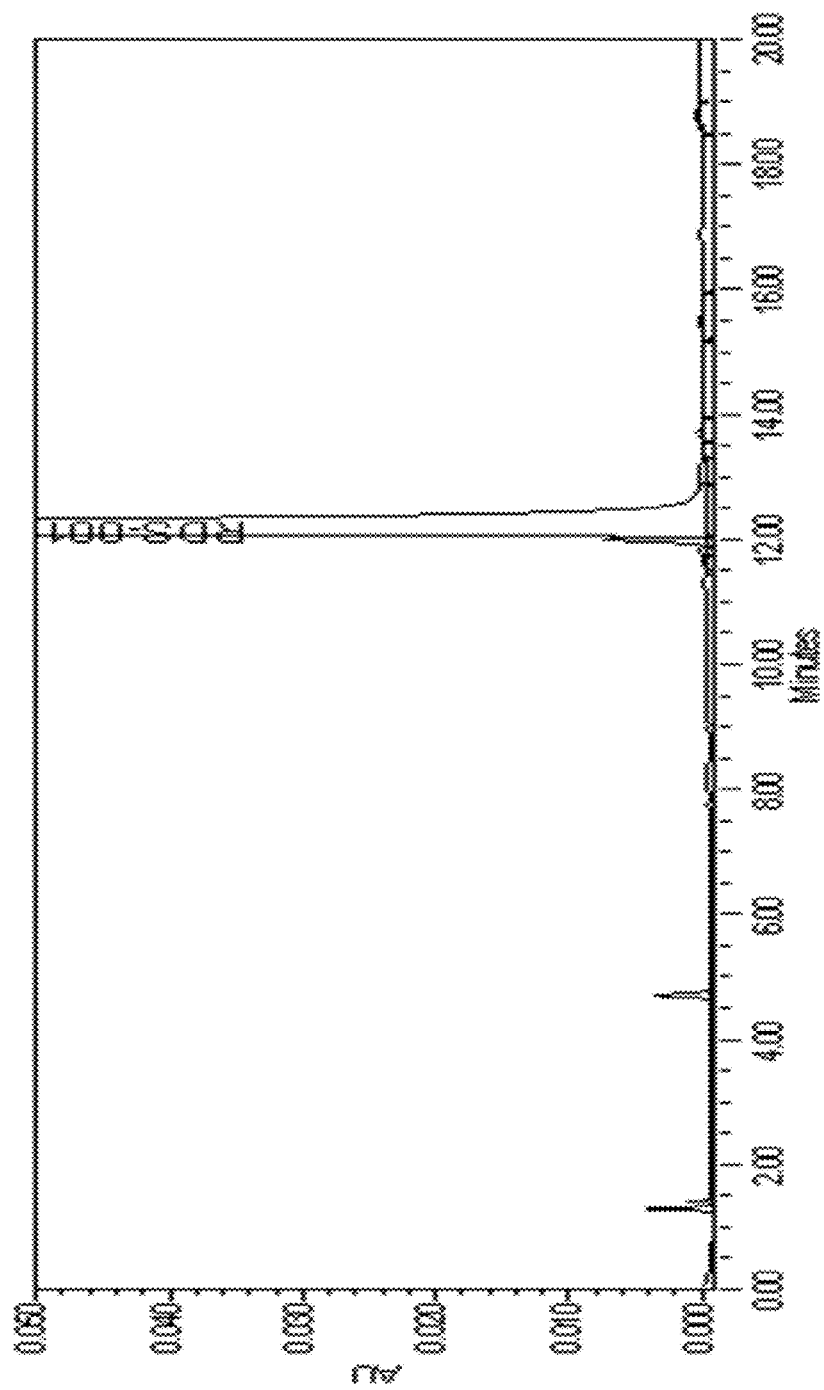

FIGS. 12O-12S show resolution of ATP(3-34) and ATP (4-34) across a number of abaloparatide samples, namely 8AG1 (FIG. 12O), 6AG1R (FIG. 12P), RDHAG112 Fp1 (FIG. 12Q), RDHAG112 FpAv (FIG. 12R), and RDHAG112 FpArr (FIG. 12S).
Evaluation of Flow Rate and Gradient to Obtain Similar Separation Characteristics as Obtained by Using +90° C. as Column Temperature While a column temperature of (+90° C.) was very effective in improving the separation of impurities as explained above, such a high temperature may add or accelerate to the degradant profile of the drug. Two different flow rates (reduced) were evaluated at column temperature of (+60° C.) with an adapted gradient using a C4 column.
Analytical Conditions
Columns: UPLC Acquity BEH C4 1,7μ 150*2.1 mm
Mobile phase A: 64 mM (NH$_4$)$_2$HPO$_4$/H$_2$O pH 7.8
Mobile phase B: (58% 160mM (NH$_4$)$_2$HPO$_4$/ H$_2$O pH 7.8, 42% H$_2$O)/ACN 60/40
Flow rate: 0.4 ml/min and 0.3 ml/min
Detection: 220 nm
Gradient: 45% B 1.5'-45-60% B in 15'
Column temperature: 60° C.
Sample temperature: 10° C.
Injected volume: 5 μl
Sample concentration: 5 μg/5 μl H$_2$O FIG. 12T and FIG. 12U show the effect of flow rate on peak shape and resolution for 8AG1 on the phosphate/C4 column.

The column temperature at +60° C. was kept for future analyses. Both HPLC (Method 3) and UPLC (Method 4) used similar phosphate buffer. Several batches were analysed comparing HPLC and UPLC methods and the impurity profiles have been compared.

The impurities with a higher RRT than the main peak were better separated from the main peak in UPLC phosphate buffer method (Method 4) than HPLC phosphate buffer method (Method 3). The tailing of the main peak obtained in Method 3 may also contribute to the lower resolution of impurities from the main peak observed.

The UPLC analytical method showed improved resolution of impurities from API main peak compared to the HPLC method using the same solvent system.

TABLE 11

Peaks of impurities RDS-001-I05 and RDS-001-I06 under Method 4

|  | TR | RRT vs RDS-001 |
|---|---|---|
| RDS-001-I05 | 11.182 | 0.882 |
| RDS-001-I06 | 10.700 | 0.851 |

TABLE 12

Impurity profiles under Method 3 conditions

| | Method 3 - HPLC | | | | | | | | | |
|---|---|---|---|---|---|---|---|---|---|---|
| RRT | 4AI1 | 4AI2 | 4AI1R | 3AJ1 | 8AK1R | 8AK1 | 3AL1 | 7AL1 | 10AL1 | 10AL2 |
| 0.73-0.74 | 0.08 | 0.09 | 0.08 | — | — | — | 0.10 | 0.07 | 0.10 | — |
| 0.88-0.89 | 0.05 | — | — | 0.05 | — | — | — | — | — | — |
| 0.91-0.92 | 0.13 | 0.11 | 0.11 | — | — | 0.05 | — | 0.05 | — | — |
| 0.94 | 0.18 | 0.17 | 0.17 | 0.10 | — | 0.06 | 0.08 | 0.19 | 0.15 | 0.11 |
| 0.97-0.98 | 0.29 | 0.28 | 0.28 | 0.25 | 0.85 | 0.87 | 0.31 | 0.27 | 0.42 | 0.32 |

TABLE 12-continued

Impurity profiles under Method 3 conditions

Method 3 - HPLC

| RRT | 4AI1 | 4AI2 | 4AI1R | 3AJ1 | 8AK1R | 8AK1 | 3AL1 | 7AL1 | 10AL1 | 10AL2 |
|---|---|---|---|---|---|---|---|---|---|---|
| 1.00 | 98.42 | 98.89 | 98.17 | 98.76 | 98.46 | 98.39 | 98.21 | 99.20 | 98.94 | 99.25 |
| 1.06-1.07 | 0.56 | 0.60 | 0.62 | 0.51 | 0.34 | 0.34 | 0.66 | — | — | — |
| 1.09-1.10 | 0.14 | 0.09 | 0.28 | 0.12 | — | — | — | — | — | — |
| 1.13-1.14 | 0.13 | 0.25 | 0.19 | | 0.23 | 0.25 | 0.37 | 0.14 | 0.06 | 0.15 |
| 1.15-1.16 | — | 0.07 | — | 0.11 | — | — | 0.14 | — | — | — |
| 1.2 | — | 0.07 | — | — | — | — | — | — | — | — |

TABLE 13

Impurity profiles according to Method 4

Method 4 - UPLC

| RRT | 4AI1 | 4AI2 | 4AI1R | 3AJ1 | 8AK1R | 8AK1 | 3AL1 | 7AL1 | 10AL1 | 10AL2 |
|---|---|---|---|---|---|---|---|---|---|---|
| 0.74 | 0.04 | 0.05 | 0.05 | 0.05 | — | — | 0.08 | 0.05 | 0.05 | — |
| 0.79 | 0.06 | 0.06 | 0.07 | — | — | — | — | — | 0.08 | — |
| 0.89 | 0.10 | 0.10 | 0.12 | — | — | — | — | 0.05 | 0.10 | — |
| 0.90 | — | — | — | — | — | — | — | — | 0.07 | — |
| 0.93 | 0.11 | 0.13 | 0.11 | — | — | — | 0.05 | | 0.10 | — |
| 0.94 | 0.08 | 0.05 | 0.14 | 0.09 | 0.14 | 0.10 | 0.08 | 0.10 | 0.13 | 0.09 |
| 0.95 | 0.06 | 0.08 | — | — | — | 0.05 | — | — | — | — |
| 0.97 | 0.18 | 0.19 | 0.20 | 0.15 | 0.10 | 0.11 | 0.06 | 0.11 | 0.10 | 0.16 |
| 1.00 | 98.88 | 98.83 | 98.57 | 99.30 | 99.32 | 99.36 | 99.37 | 99.31 | 98.79 | 99.37 |
| 1.13-1.14 | 0.07 | 0.08 | 0.11 | — | — | — | 0.08 | 0.11 | 0.11 | 0.06 |
| 1.14 | — | — | — | — | — | — | 0.08 | — | — | — |
| 1.16-1.17 | 0.17 | 0.24 | 0.15 | 0.23 | 0.39 | 0.39 | 0.22 | 0.17 | 0.19 | 0.14 |
| 1.18 | 0.09 | — | 0.15 | — | — | — | — | — | — | — |
| 1.21-1.22 | — | 0.07 | 0.11 | 0.10 | — | — | — | 0.05 | 0.09 | 0.09 |
| 1.23-1.24 | — | — | 0.04 | — | — | — | — | — | 0.06 | — |
| 1.25-1.26 | 0.13 | 0.12 | 0.14 | 0.08 | 0.05 | — | — | 0.05 | 0.11 | 0.10 |

Example 5

Stability Indicating Methods

TFA Solvent System Methods (Methods 1 and 2) HPLC v UPLC

Figure 13A:
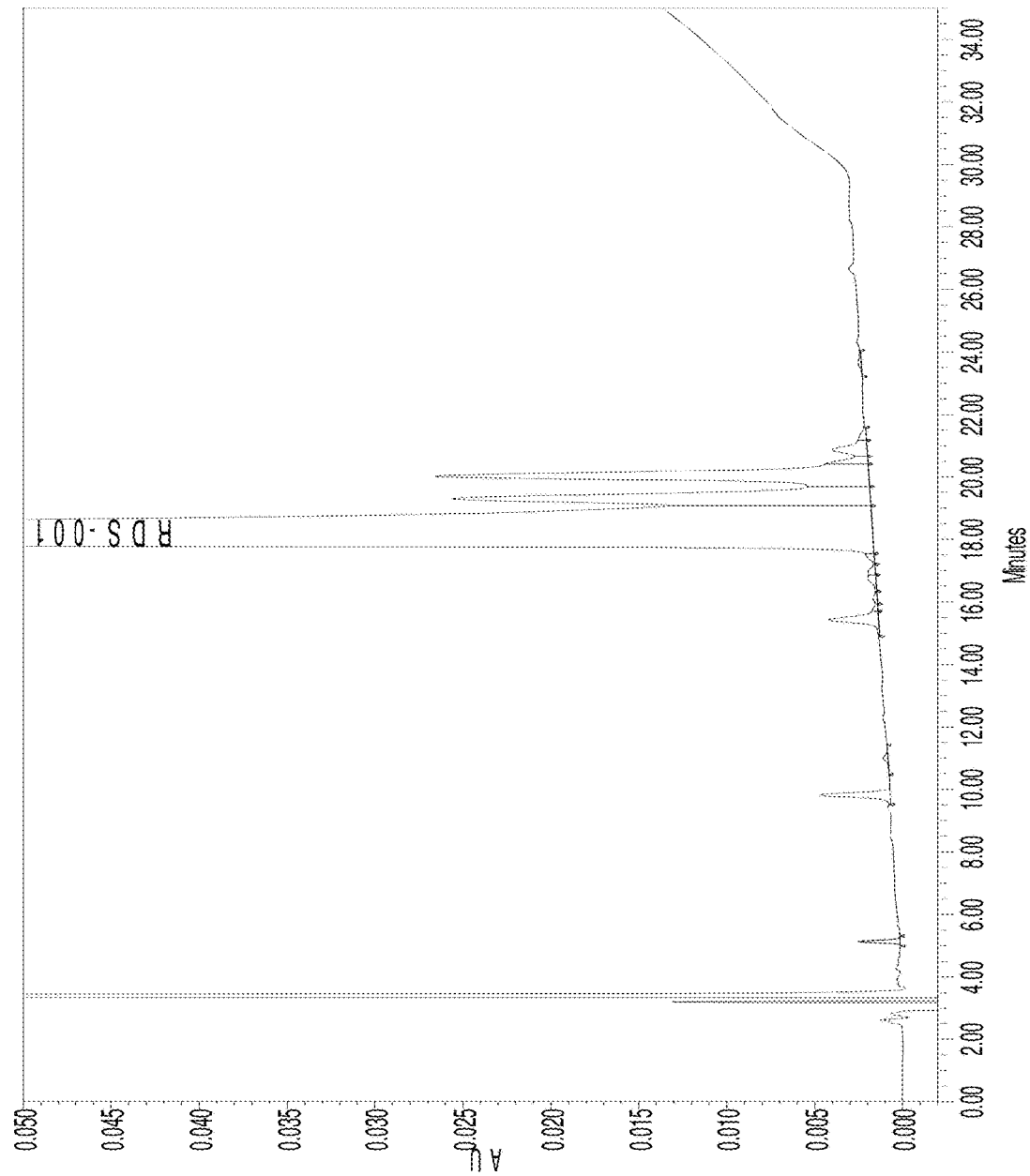
FIGS. 13A-13L: Acid, base, and heat stress results for Methods 1-4.
Figure 13B:
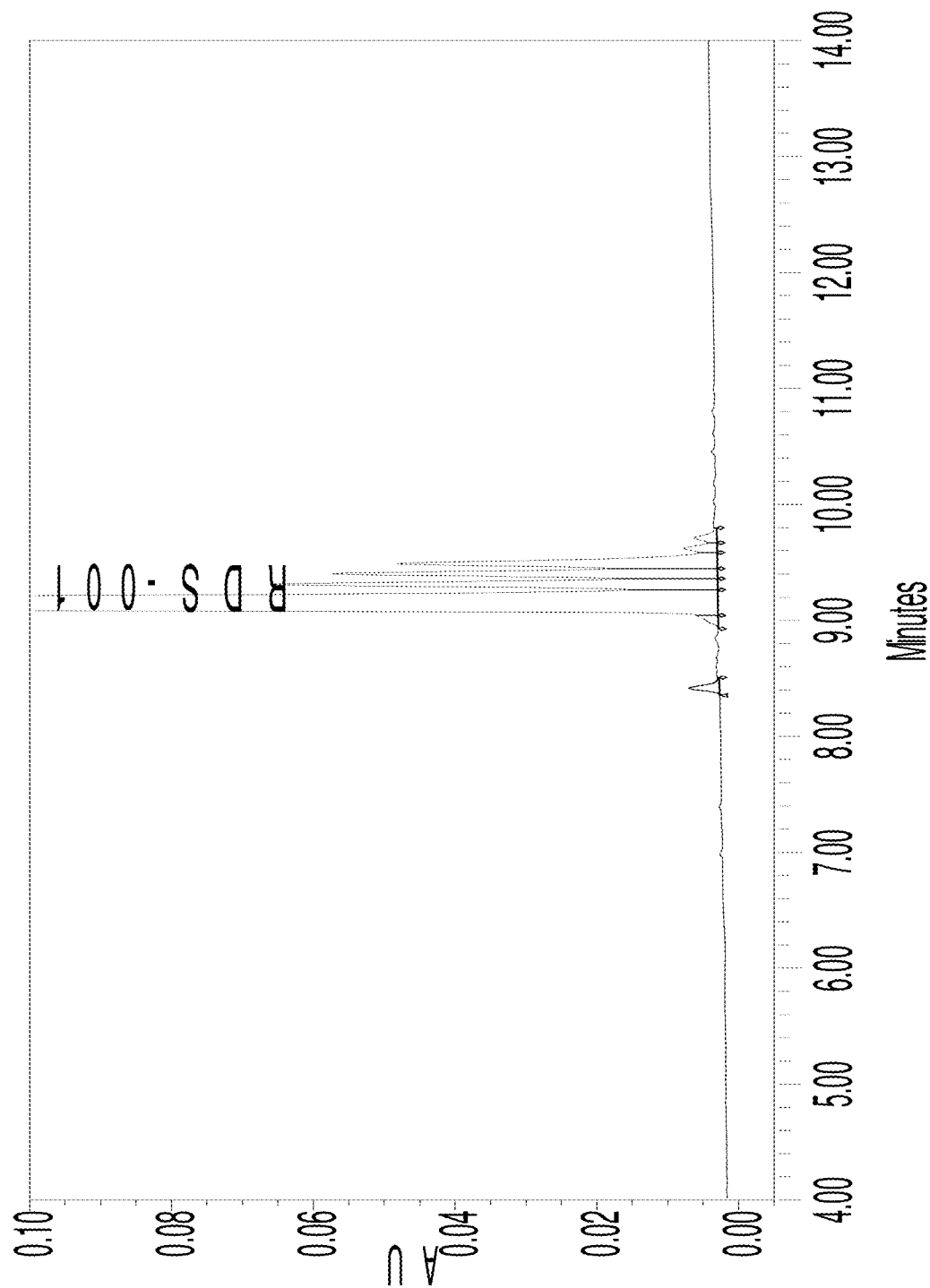
Figure 13C:
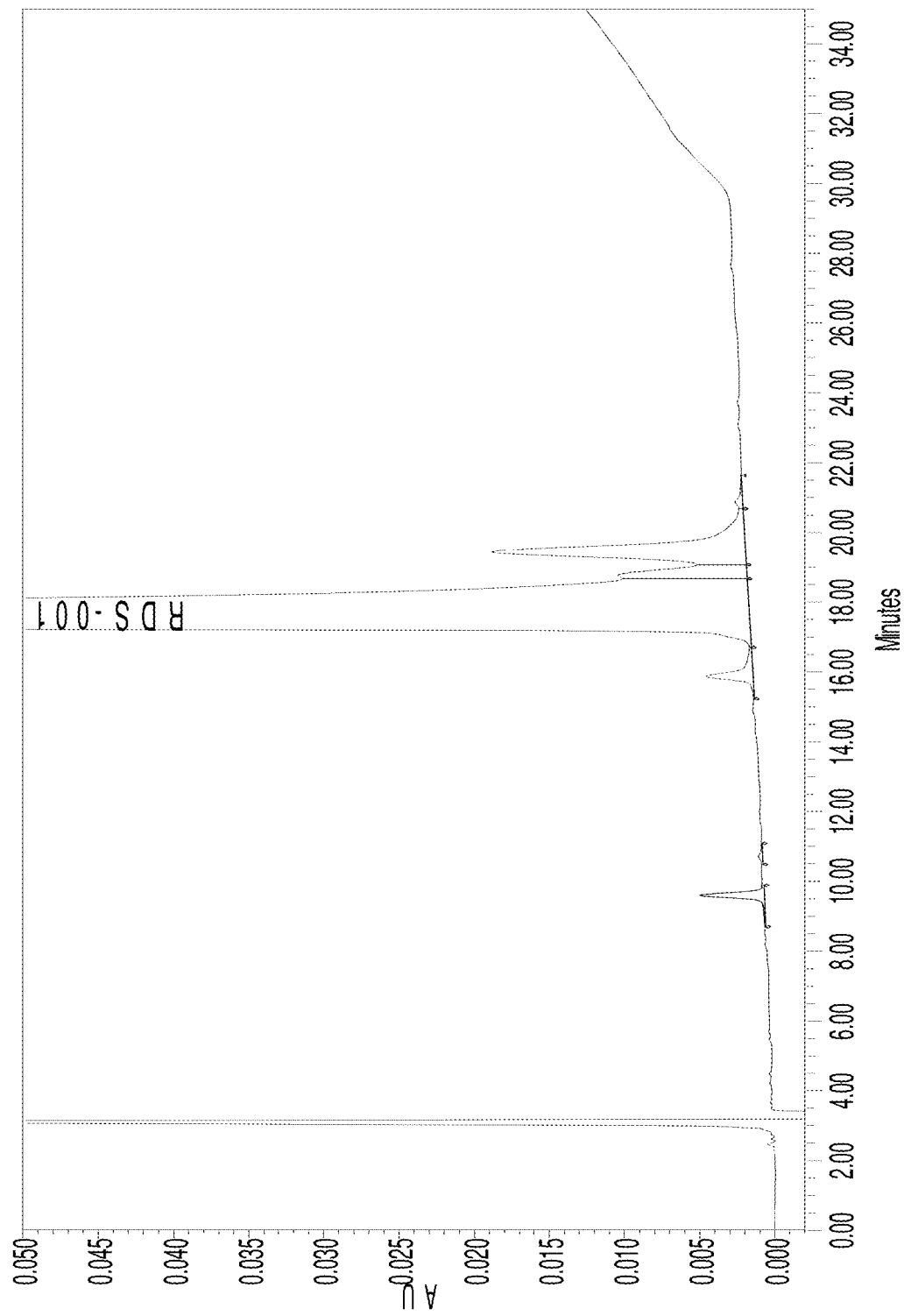
Figure 13D:
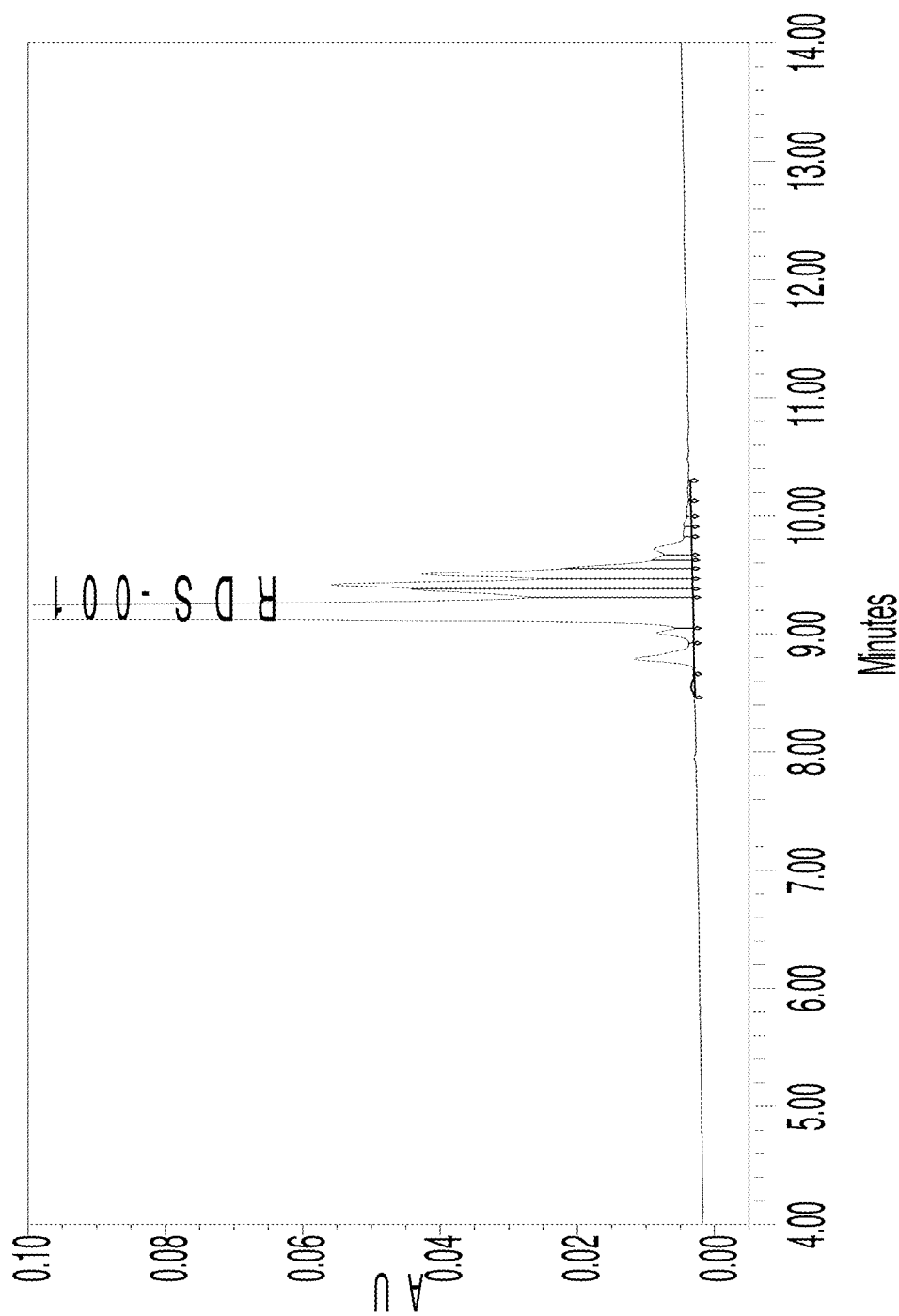
Figure 13E:
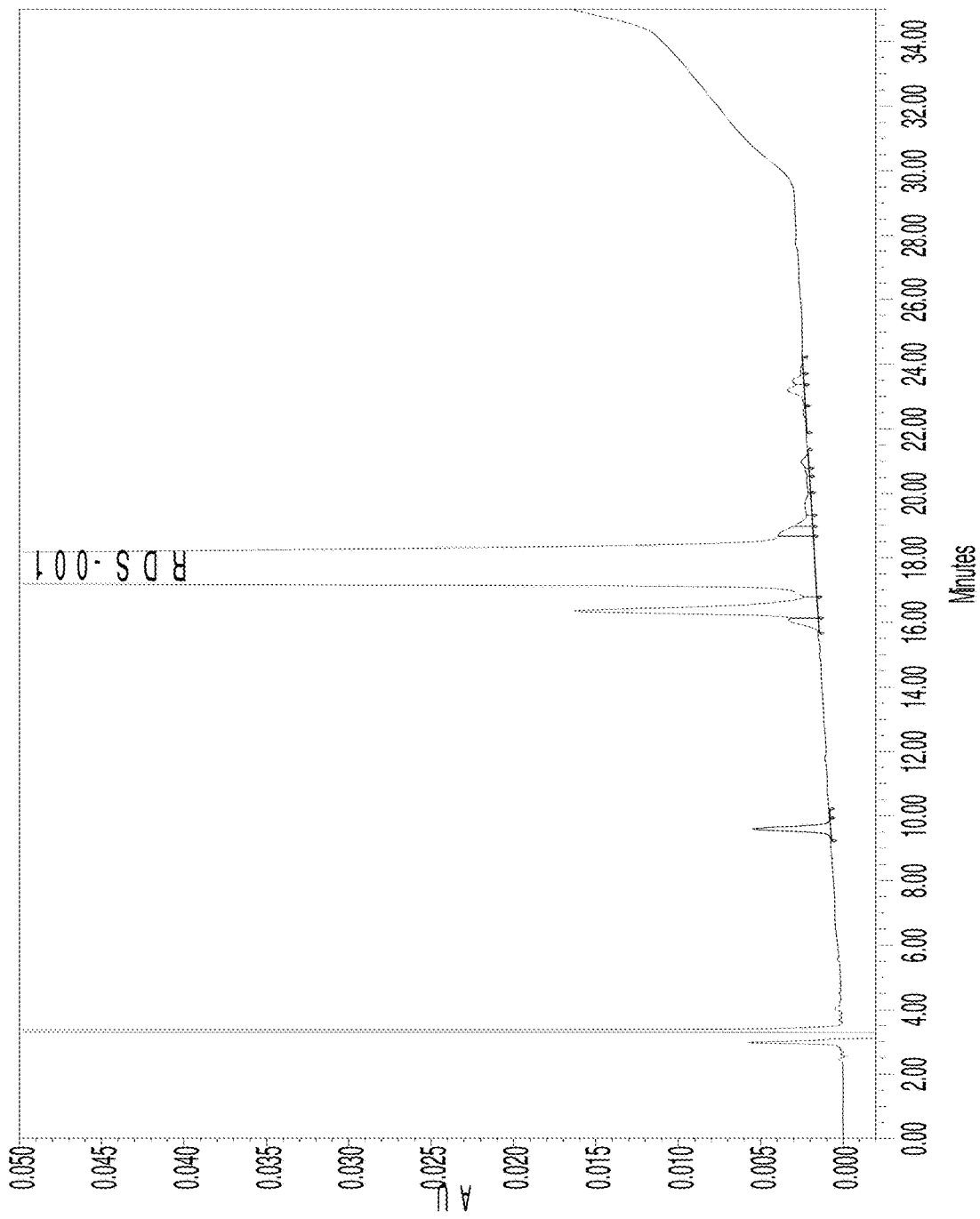
Figure 13F:
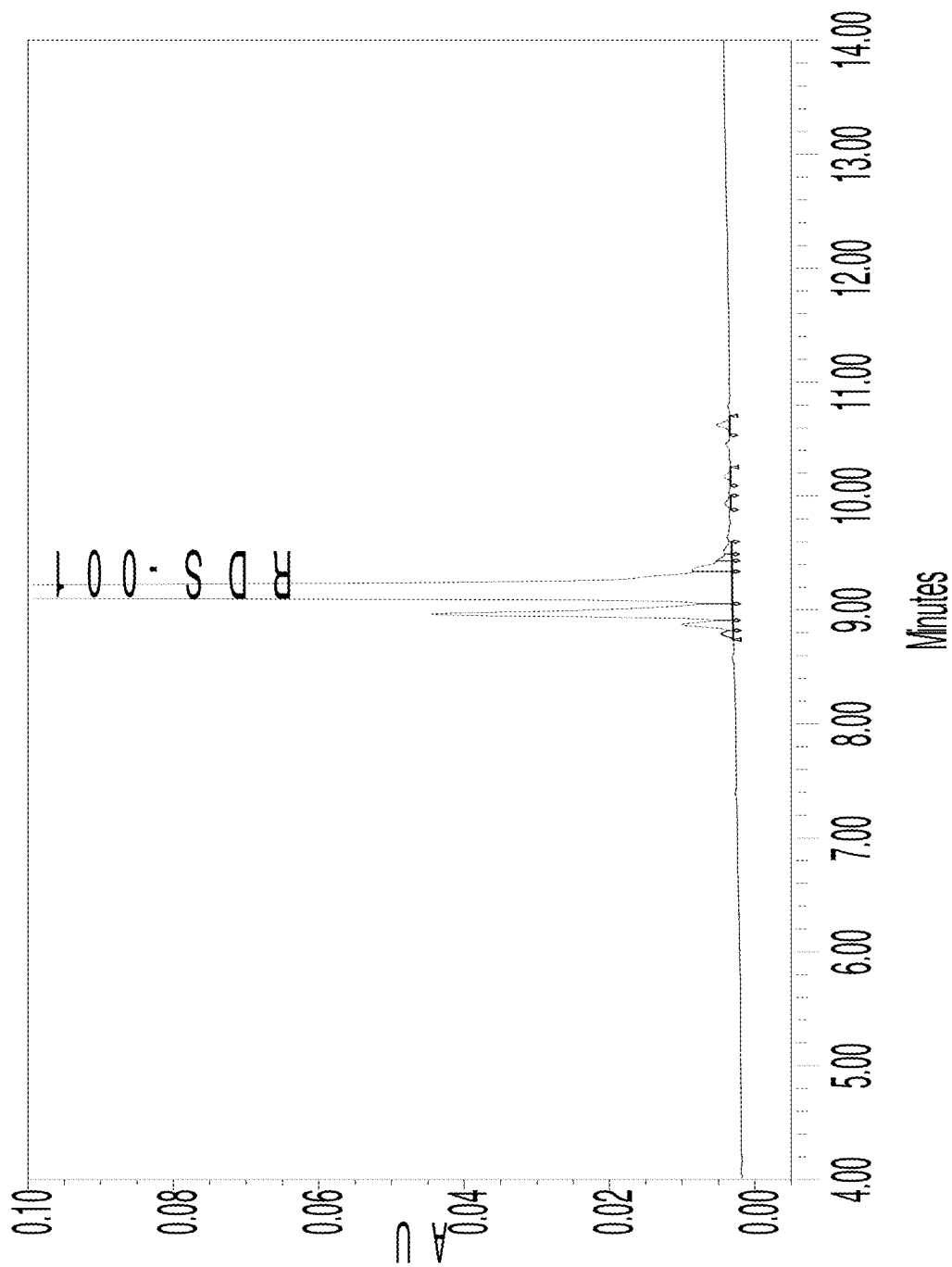

Chromatograms for acid stress (HCl 1N), base stress (NaOH 0.01N), and heat stress (+80° C.) for Method 1 are set forth in FIGS. 13A, C, and E, respectively. Chromatograms for acid stress (HCl 1N), base stress (NaOH 0.01N), and heat stress (+80° C.) for Method 2 are set forth in FIGS. 13B, D, and F, respectively.

Ammonium Phosphate Solvent Methods (Method 3 and Method 4)

Figure 13G:
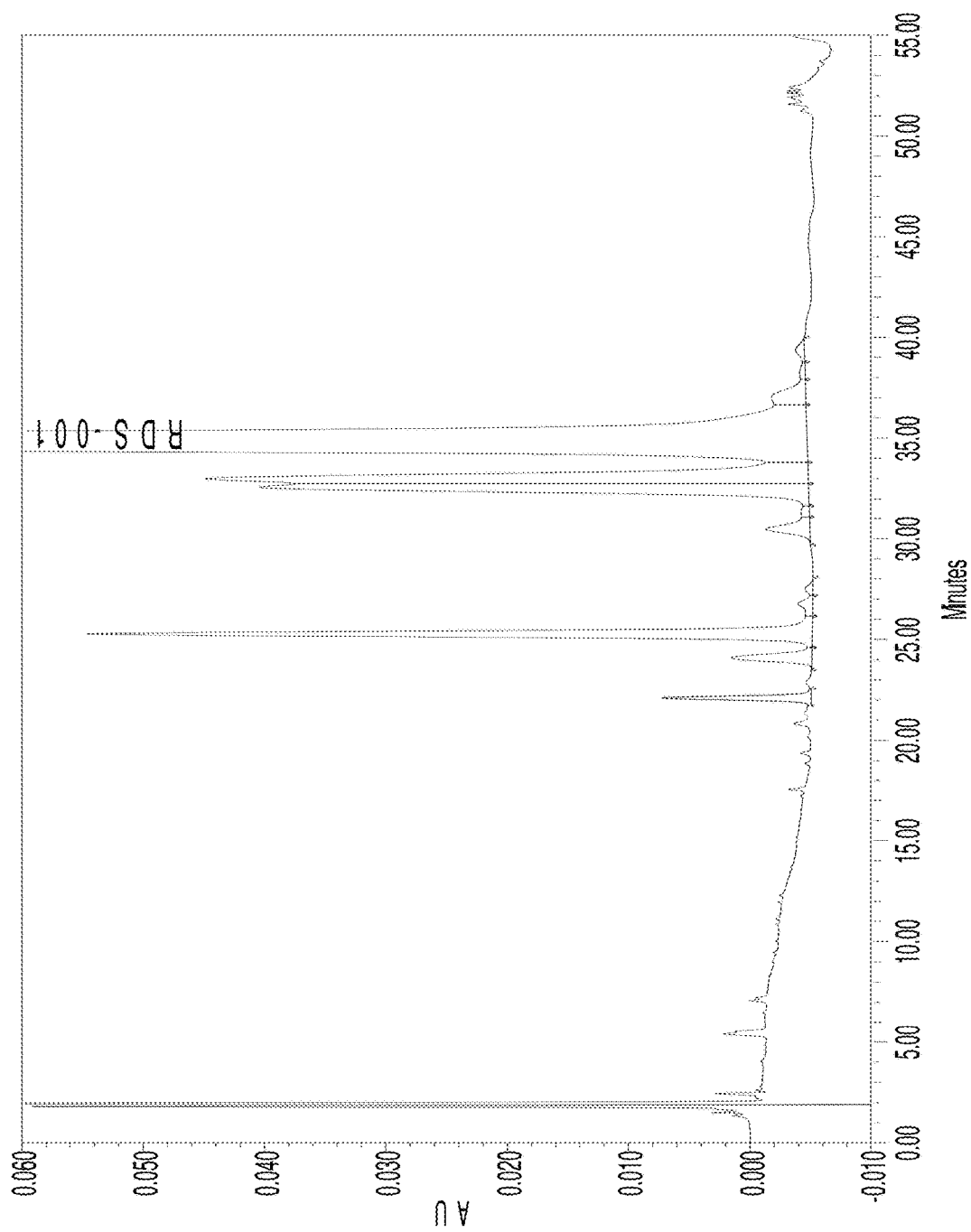
Figure 13H:
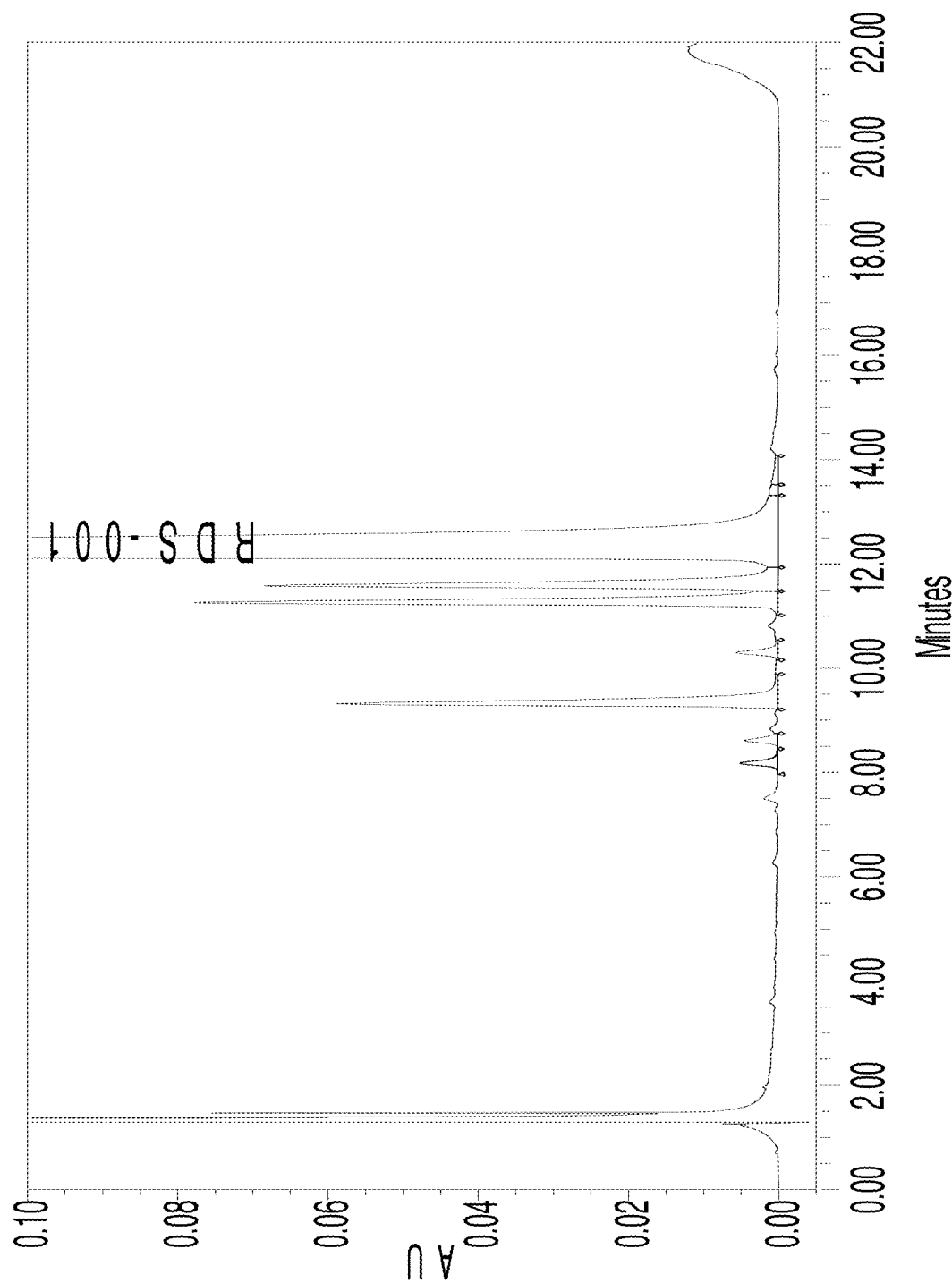
Figure 13I:
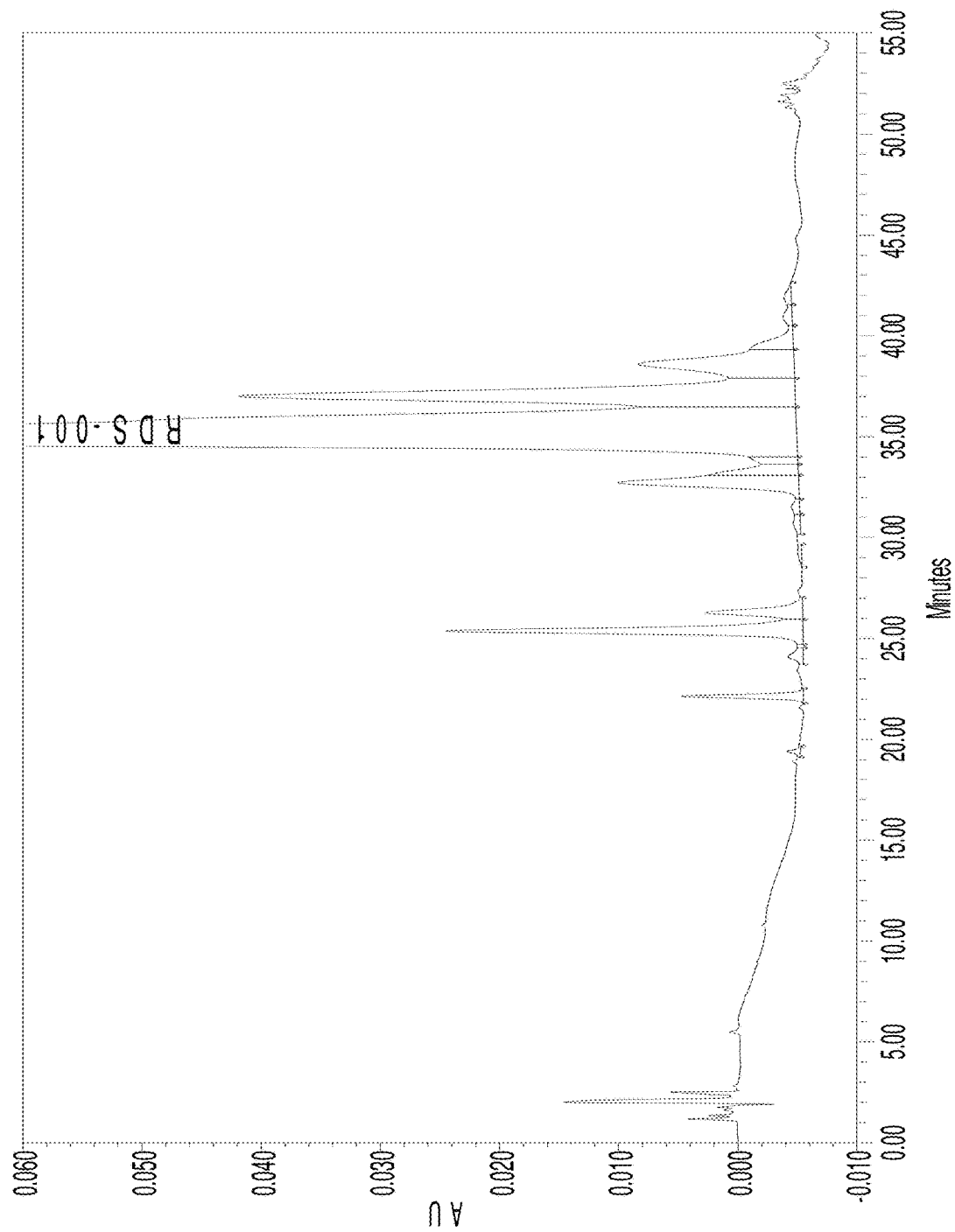
Figure 13J:
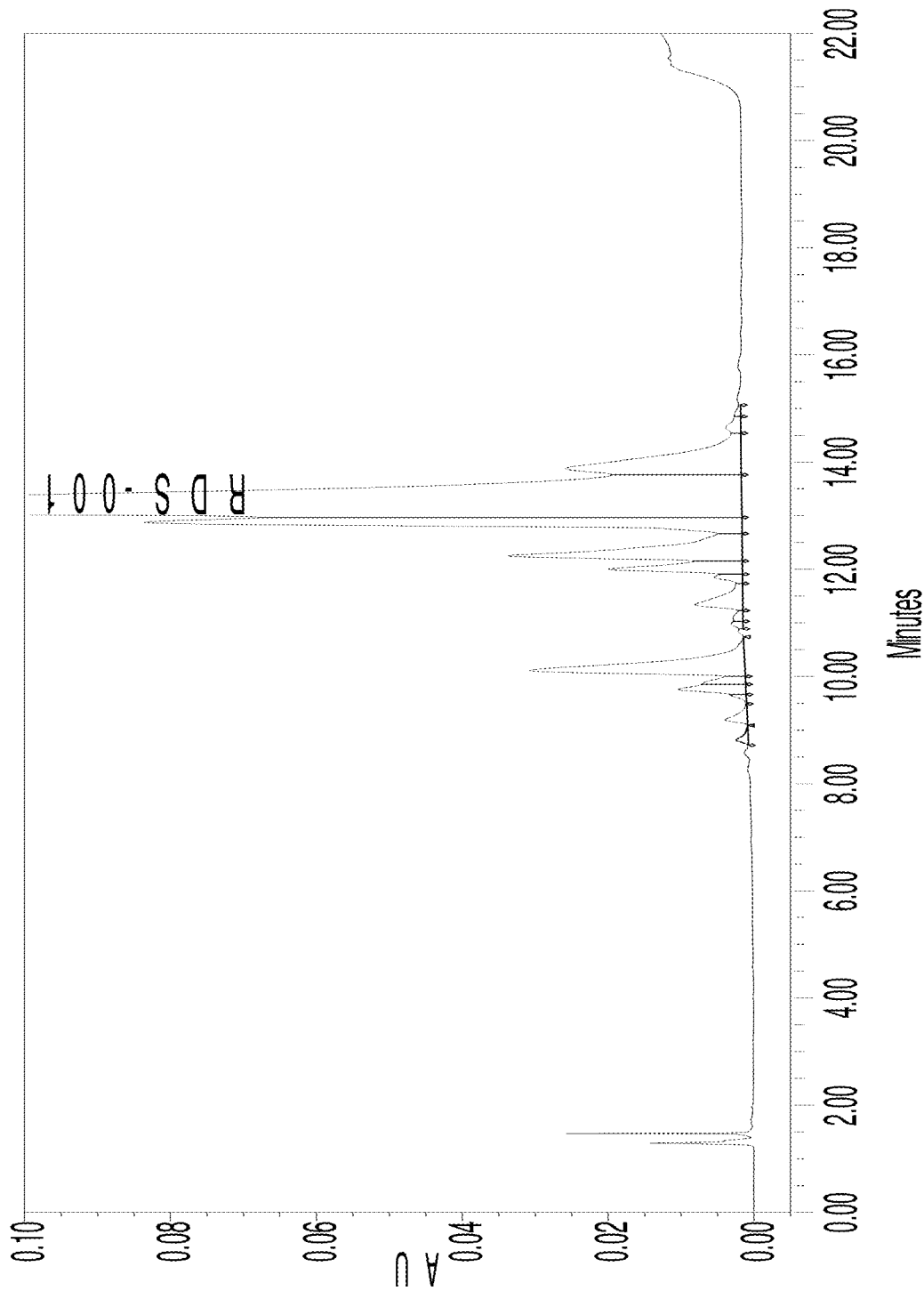
Figure 13K:
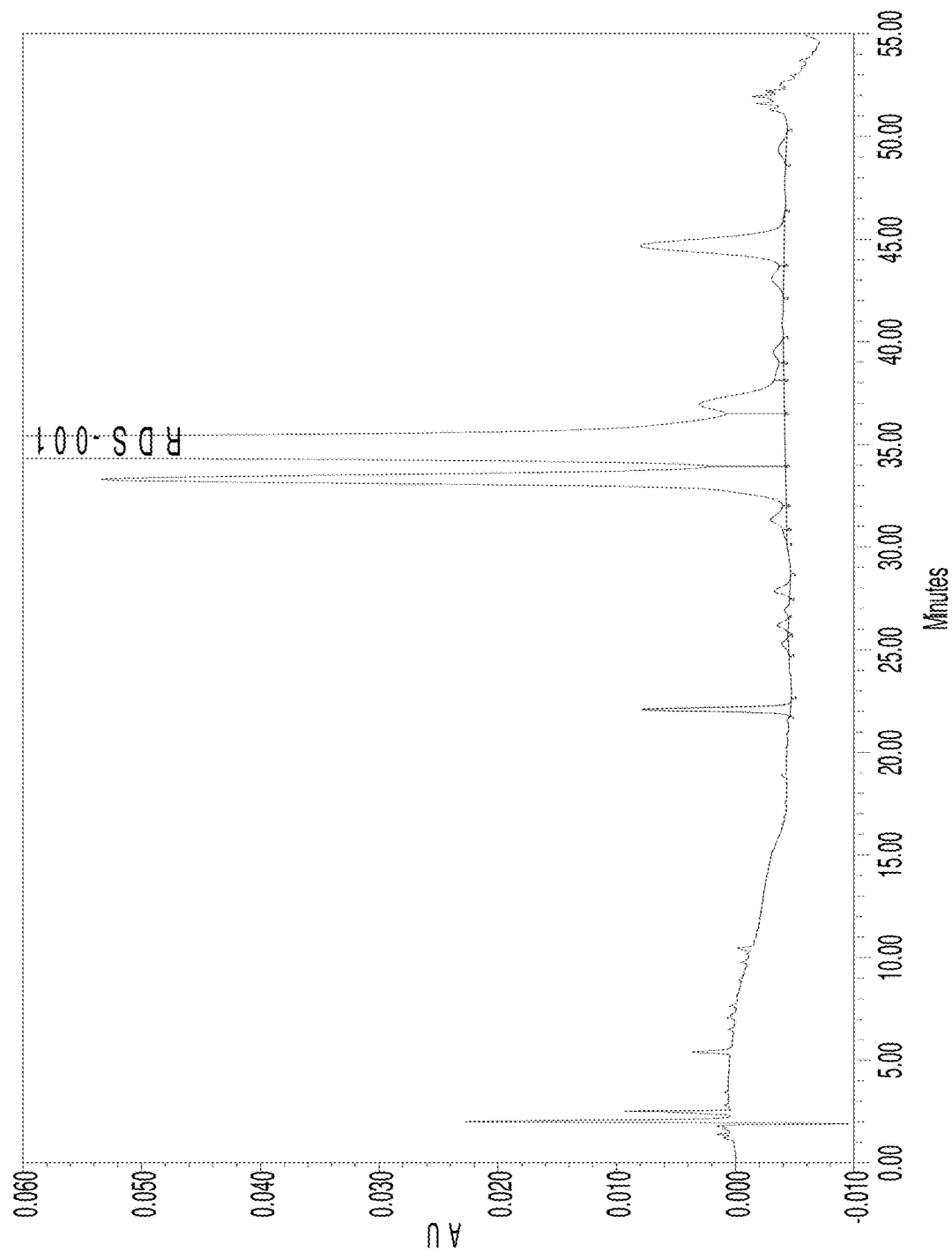
Figure 13L:
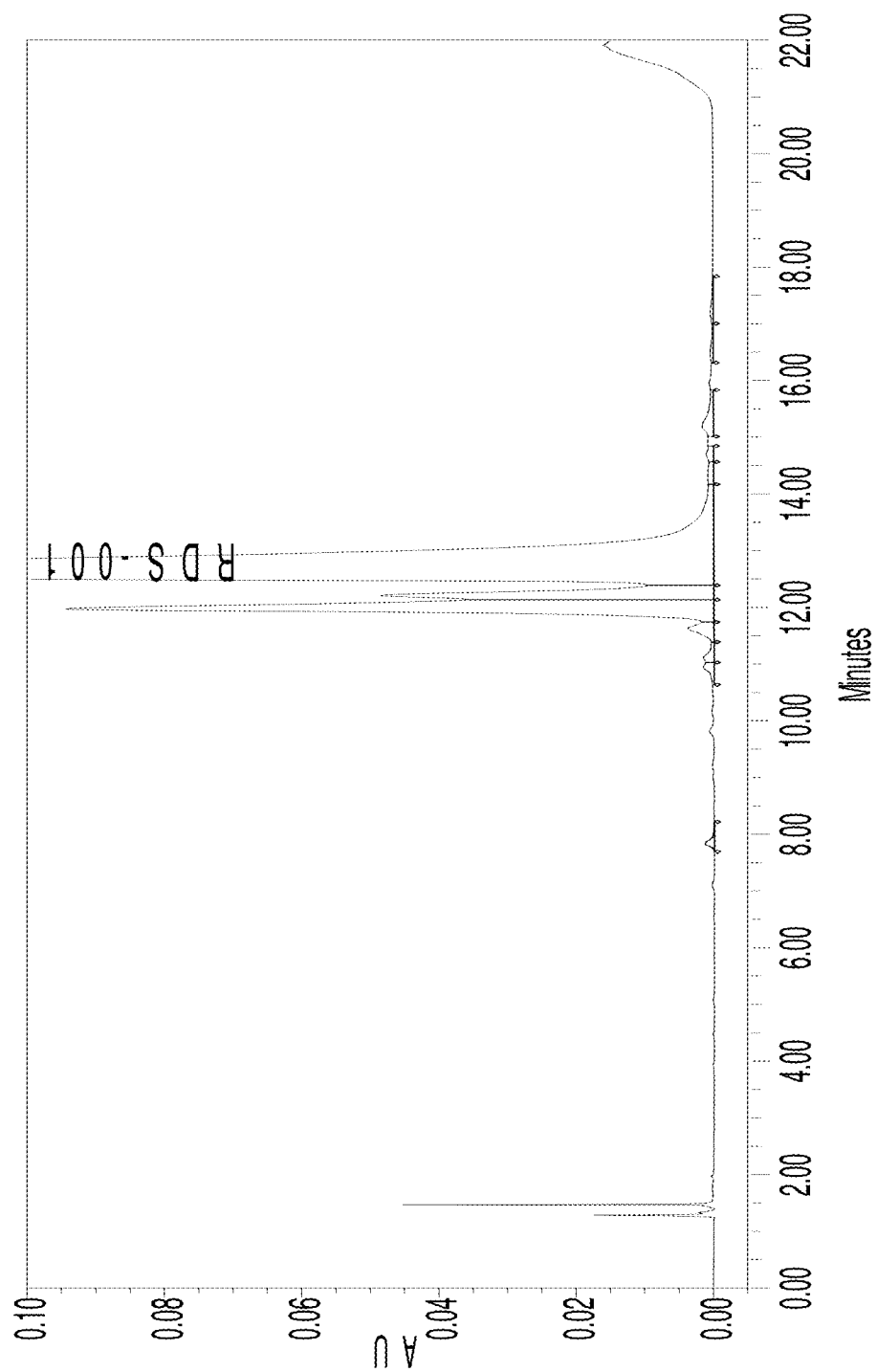

Chromatograms for acid stress (HCl 1N), base stress (NaOH 0.01N), and heat stress (+80° C.) for Method 3 are set forth in FIG. 13G, I, and K, respectively. Chromatograms for acid stress (HCl 1N), base stress (NaOH 0.01N), and heat stress (+80° C.) for Method 4 are set forth in FIGS. 13H, J, and L, respectively.

HPLC and UPLC using the phosphate-buffer (methods 3 and 4) provided similar impurity profiles. However, UPLC method (Method 4) provide better impurities discrimination and reduced tailing effects. As can be seen, methods 3 and 4 were considerably better at resolving stress-derived impurities in the chromatograms.

Examples of the methods disclosed herein are summarized below.

TABLE 14

TFA Solvent System (Method 1 and Method 2)

| | Method 1 | | | Method 2 | | |
|---|---|---|---|---|---|---|
| Column | Zorbax 300SB C8 5 µm 250 × 4.6 mm (or equivalent) | | Column | Waters Acquity CSH C18 1.7 µm, 100 × 2.1 mm | | |
| Column Temperature | +50° C. | | Column Temperature | +40° C. | | |
| Autosampler temperature | +10° C. | | Autosampler temperature | +10° C. | | |
| Flow rate | 0.9 mL/min | | Flow rate | 300 µL/min | | |
| Detection wavelength | UV: 220 nm | | Detection wavelength | UV: 220 nm | | |
| Injection volume | 20 µL | | Injection volume | 2 µL | | |
| Elution conditions | Gradient: | | Elution conditions | Gradient: | | |
| Time (min.) | % mobile phase A | % mobile phase B | Time (min.) | % mobile phase A2 | % mobile phase B2 | |
| 0.0 | 71 | 29 | 0.0 | 68 | 32 | |
| 25.0 | 65 | 35 | 0.5 | 68 | 32 | |
| 35.0 | 65 | 35 | 14.5 | 40 | 60 | |
| 36.0 | 71 | 29 | 15.0 | 20 | 80 | |
| 45.0 | 71 | 29 | 15.5 | 20 | 80 | |
| | | | 15.6 | 68 | 32 | |
| | | | 18.0 | 68 | 32 | |
| Analysis stop time | 35 minutes | | Analysis stop timer | 14.5 minutes | | |

TABLE 15

Ammonium Phosphate Solvent System (Method 3/Method 4)

| | Method 3 | | | Method 4 | | |
|---|---|---|---|---|---|---|
| Column | X-Bridge C18, 5 µm, 150 × 4.6 mm | | Column | Waters BEH300 C4 1.7 µm, 150 × 2.1 mm | | |
| Column Temperature | +60° C. | | Column Temperature | +60° C. | | |
| Autosampler temperature | +15° C. | | Autosampler temperature | +10° C. | | |
| Flow rate | 0.8 mL/min | | Flow rate | 300 µL/min | | |
| Detection wavelength | UV: 214 nm | | Detection wavelength | UV: 220 nm | | |
| Injection volume | 20 µL | | Injection volume | 5 µL | | |
| Elution conditions | Gradient: | | Elution conditions | Gradient: | | |
| eta | % mobile phase A | % mobile phase B | Time (min.) | % mobile phaseA2 | % mobile phaseB2 | |
| 0.0 | 77 | 23 | 0.0 | 52 | 48 | |
| 12.0 | 53 | 47 | 1.5 | 52 | 48 | |
| 46.0 | 53 | 47 | 18.5 | 39 | 61 | |
| 56.0 | 43 | 57 | 19.0 | 1 | 99 | |
| 58.0 | 0 | 100 | 21.0 | 1 | 99 | |
| 63.0 | 0 | 100 | 21.5 | 52 | 48 | |
| 65.0 | 77 | 23 | 25.0 | 52 | 48 | |
| 75.0 | 77 | 23 | | | | |
| Analysis stop time | 60 minutes | | Analysis stop timer | 21.0 minutes | | |

Example 6

Kinetics of beta-Asp10 Formation And Appropriate Storage Determination

When older clinical lots of abaloparatide-SC (aqueous formulated drug product) that had been kept in refrigerated storage for more than 36 months (C12689, D26565, and D28382) were analyzed using the new HPLC method (Example 3), a new degradant was separated that had not been detected by previous chromatographic methods. Subsequent analyses demonstrated that this degradant was also present in varying amounts in API (though less than formulated and stored samples). The new degradant was isolated, purified, and analyzed, and structural analysis indicated that it was beta-Asp10. Beta-Asp10 contains a rearrangement of the Asp residue at position 10 arising from a temperature-dependent hydrolysis reaction. This reaction is illustrated in FIGS. 1A-C.

Analysis of the older lots (i.e., older than 36 months) indicated that more than 3% of the abaloparatide in the formulation could be converted to abaloparatide (beta-Asp10). Analysis of newer clinical lots stored at one month for room temperature indicated that the percentage of (beta-Asp10) in the formulation could be more than 1%. Table 16 summarizes these analyses, and shows the differences in impurity detection between the original HPLC method (no buffer)("original test method") and the improved method (buffered) ("current test method").

TABLE 16

Comparative analysis of abaloparatide-SC drug product clinical and stability batches

| Method | Specifications | Clinical & Stability Batch C12689 | | Clinical & Stability Batch D26565 | | Clinical & Stability Batch D28382 | |
|---|---|---|---|---|---|---|---|
| | | Original test method 5° C. 36 months | Current test Methods 5° C. ~54 months | Original test method 5° C. 36 months | Current test Methods 5° C. ~41 months | Original test method 5° C. 36 months | Current test Methods 5° C. ~38 months |
| Abaloparatide Assay[1] (mg/mL) | 1.8-2.2 | 2.00 | — | 1.97 | — | 1.94 | — |
| Total impurities[1] (%) | ≤3.0 | 0.3 | — | 0.2 | — | 0.2 | — |
| Abaloparatide Assay[2] (mg/mL) | 1.8-2.2 | — | 1.91 | — | 1.95 | — | 1.90 |
| Total impurities[2] (%) | ≤3.0 | — | 5.3 | — | 4.0 | — | 3.8 |
| beta-Asp10 isomer content (%) | | ND | 4.0 | ND | 3.1 | ND | 3.0 |

[1]Testing performed with original methodology, HPLC method - TG1
[2]Testing performed with revised methodology, UPLC method FG2
ND = not detected As can be seen, the new methods of analysis allowed for significant resolution of abaloparatide samples when compared to older methods using HPLC and/or non-ionic buffering solvents.

of significance was the identification and qualification of a heretofore unidentified isomer of abaloparatide, (beta-Asp10) abaloparatide. By comparing a number of samples stored under different conditions, the rate of formation of (beta-Asp10) abaloparatide could be accurately quantified and plotted on a time course at a given temperature.

The predictability of (beta-Asp10) abaloparatide formation in the formulated drug product was established and the isomerization of abaloparatide to the isomer occurred according to strictly zero order kinetics.

(beta-Asp10) abaloparatide analog levels (mean) in registration batches at different storage conditions are given in the Table 17 immediately below.

TABLE 17

(beta-Asp10) abaloparatide levels in formulated samples by time

| | Time Point | | | | | | | |
|---|---|---|---|---|---|---|---|---|
| Temp | 0 M | 1 M | 3 M | 6 M | 9 M | 12 M | 18 M | 24 M |
| 5° C. Long term storage condition (%) | 0.3 | — | 0.5 | 0.76 | 0.96 | 1.03 | 1.66 | 1.93 |
| 25° C. (Accelerated condition) (%) | 0.3 | 1.26 | 3.26 | 6.3 | 9.43 | 11.96 | 16.73 | 20.73 |
| 40° C. (Stress condition) (%) | 0.3 | 7.10 | 18.76 | 32.9 | — | — | — | — |

Figure 7:
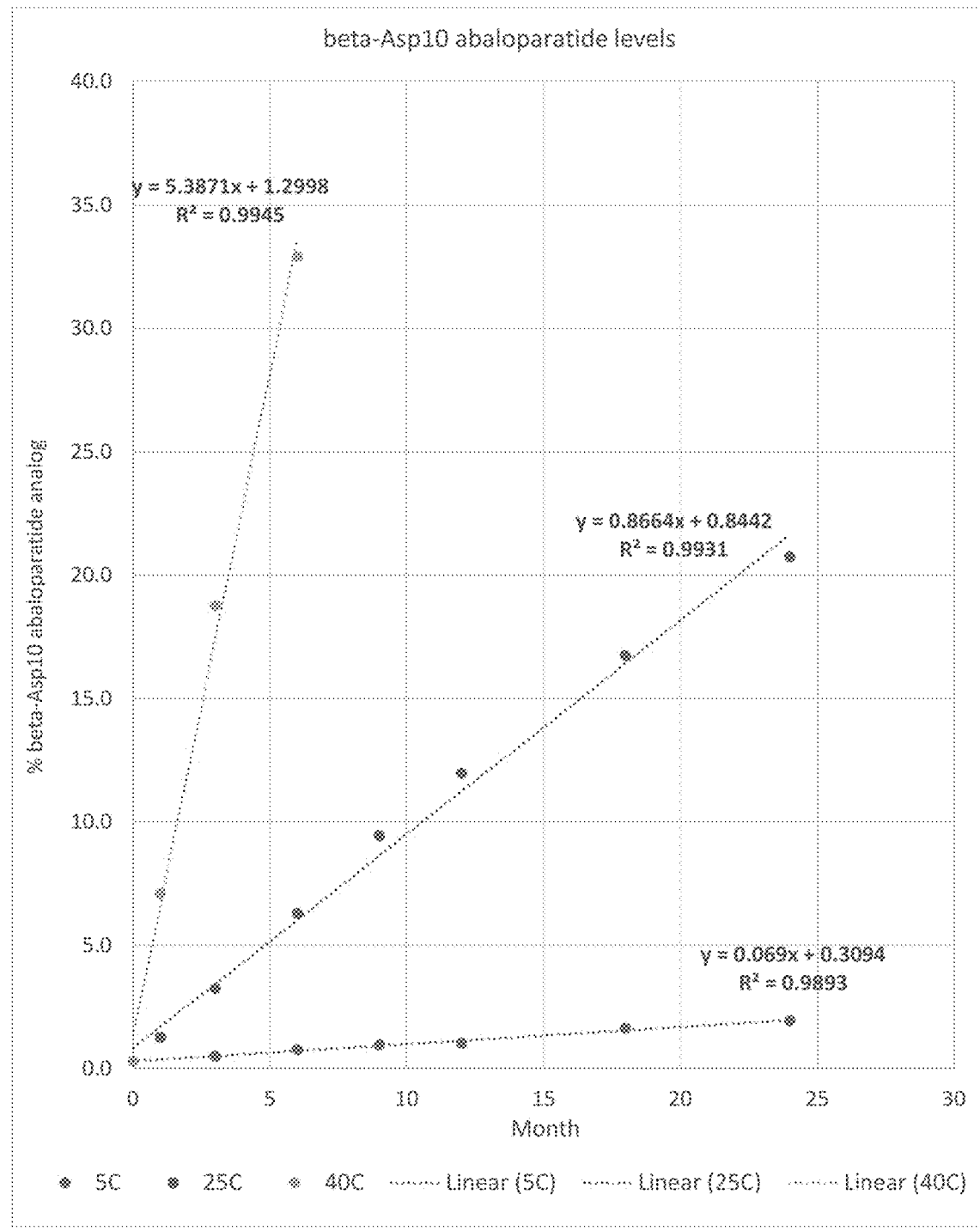
FIG. 7: Formation of beta-Asp10 abaloparatide from abaloparatide analog plotted against time.

Formation of (beta-Asp10) abaloparatide analog was plotted against time in months (see FIG. 7), which resulted in an excellent straight line fit for data at each temperature condition, suggesting that rate of formation of (beta-Asp10) abaloparatide, and therefore rate of isomerization for abaloparatide, follows zero order kinetics. The slope of the straight line for each temperature was the observed rate constant ($K_{obs}$) for formation of (beta-Asp10) abaloparatide. Rate constants at each temperature are tabulated in the top row of Table 18.

TABLE 18

Observed rate constant at various temperature

| Temp | 40° C. | 25° C. | 5° C. |
|---|---|---|---|
| $k_{obs}$ (%/month) | 5.38 | 0.993 | 0.0690 |
| $K_{calc}$ (%/month) | 5.19 | 0.938 | 0.0674 |
| Difference (%) | 3.5 | −5.6 | 2.3 |

Arrhenius Plot and Calculation of Activation Energy for Abaloparatide Degradation.

Figure 8:
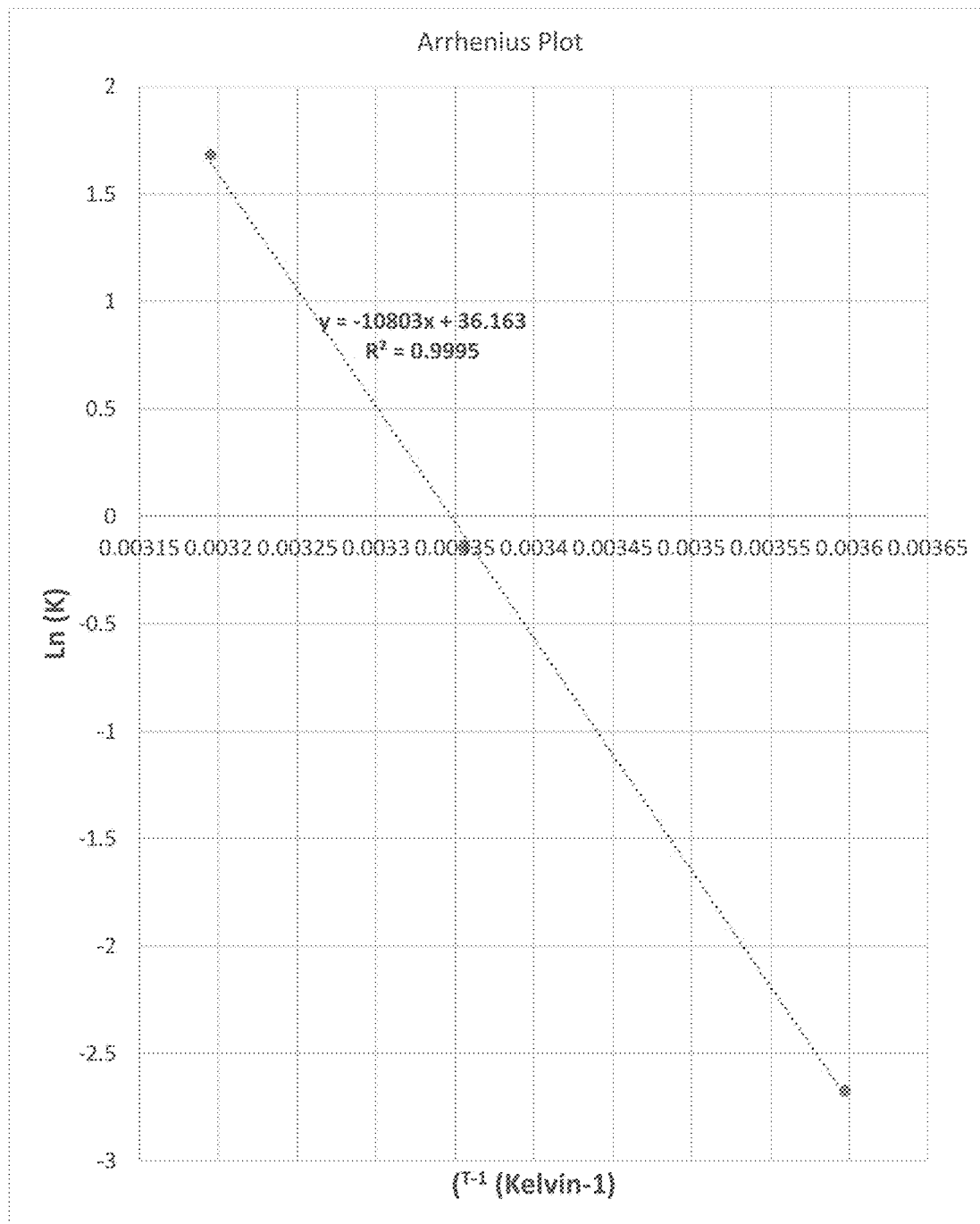
FIG. 8: Arrhenius plot of beta-Asp10 formation.

An Arrhenius plot was constructed (FIG. 8) by plotting the natural logarithm of the rate constants (k) for three storage temperatures, against the reciprocals of those temperatures in Kelvin. The plot indicates that the rate of formation of (beta-Asp10) abaloparatide is highly predictable at temperatures between 5° C. and 40° C., with a R2 value of 0.9997 for best linear regression fit of the data. The activation energy, Ea, derived with high accuracy from the slope of a linear regression best fit of the Arrhenius plot is Ea=91,670 J/mol. This activation energy can be used to calculate the rate constant for abaloparatide isomerization and (beta-Asp10) abaloparatide formation at any temperature. A comparison of the calculated rate constants to the corresponding, measured real time rate constants derived from a linear fit of the data in Table 18, demonstrates predictability with high precision. For example, the observed rate constant at 5° C., $K_{obs}$=0.0655%/month agrees well with the predicted value, $K_{calc}$=0.0644%/month, with only a 0.0011% absolute difference and a 1.7% relative difference. [000169] The amount of b-Asp10 in the API must be determined with rigor and set accordingly to achieve the desired stability profile after pre-specified storage conditions. Previously, this could not be done as the methods used were insufficient for its identification and quantification. Therefore, not only has a new degradant been discovered but the methods described herein have allowed the formation rate equation to be determined and thus allow for setting its specification in the API when coupled with a desired storage stability profile. Based on calculations from the extrapolated data demonstrating a very linear time-product course across different temperatures including refrigerated conditions (2-8° C.) and room temperature (e.g., 20-25° C.), it was determined that a predetermined set point of ≤5% of (b-Asp10) could be secured using abaloparatide API starting with ≤0.5% (b-Asp10) and stored for up to 23 months at refrigerated conditions followed by up to one month at room temperature. It was also shown that the desired ≤5% (beta-Asp10) abaloparatide level could be secured using abaloparatide API starting with ≤0.5%; as storage for 35 months at refrigerated conditions followed by up to one month room temperature contained desired ≤5% (beta-Asp10) abaloparatide. A method of stability confirmation is also provided comprising the storage of abaloparatide for 23 months under refrigerated conditions followed by one month at room temperature, or 35 months under refrigerated conditions followed by one month at room temperature, wherein evaluating for (beta-Asp10) in the starting API predicts the ultimate acceptability of an aqueous formulation containing abaloparatide. In order for the required purity to be met for abaloparatide drug product, the API must be analyzed as enabled by the novel methods of LC analysis described herein and needs to be ≤0.5% (b-Asp10). Similarly, the API, once formulated into cartridges is tested for purity including evaluation for (b-Asp10) right after the cartridge is formulated. This is also an important evaluation point for (b-Asp10) because the formulation itself requires time to complete mixing and filling prior to refrigeration. Therefore, the evaluation of formulated abaloparatide at this time point (designated t=0 here) is undertaken and it has been determined that the (b-Asp10) amount needs to be ≤1.0% for the desired purity level of the final drug.

As indicated above, the hydrophobicity of the column can be optimized effectively to the particular result required. Accordingly, in some embodiments of this disclosure a method of analyzing an abaloparatide sample is disclosed wherein a Cx-Silicon based reversed phase column is employed. In certain embodiments, the carbon component of the column is 16 carbons, 8 carbons or 4 carbons in linear length. In certain embodiments, the linear chain is further branched with varying alkyl groups (e.g., isopropyl). In certain embodiments, the column temperature was elevated above rt. For example, a column temperature of between 40-90° C. can be effectively employed across a range of Cx-Si reverse phase columns. In certain embodiments, a range of temperatures between 40-80° C., 40-70° C. or 40-60° C. can also be effectively used. In particular, column temperatures of about 40° C., 45° C., 50° C., 55° C., or 60° C. are all effective embodiments.

Biological characterization of (beta-Asp10) abaloparatide was evaluated in a qualified cell base potency assay for functional PTH activity using the production of cAMP as a measure of bioactivity. The results obtained in this study showed that the $EC_{50}$ was 3.297 ng/mL for (beta-Asp10) abaloparatide and the $EC_{50}$ of abaloparatide was 0.325 ng/mL for abaloparatide.

As stated above, the foregoing is merely intended to illustrate various embodiments of the present invention. The specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference as if fully set forth herein.

What is claimed is:

1. A method of analyzing a sample containing abaloparatide comprising using an HPLC and/or UPLC using a binary solvent system with a mobile phase comprising an aqueous buffer, wherein said aqueous buffer has a pH range of between 7-9 prior to mixing with any additional mobile phase solvent, wherein analyzing a sample comprises detecting and quantifying the presence of ≤5% w/w beta-Asp10 of the total peptide content.

2. The method of claim 1, wherein said aqueous buffer has a pH of between 7.5 and 8.5, prior to mixing with any additional mobile phase solvent.

3. The method of claim 2, wherein said aqueous buffer has a pH of between 7.6 and 8.0, prior to mixing with any additional mobile phase solvent.

4. The method of claim 3, wherein said aqueous buffer has a pH of about 7.8 prior to mixing with any additional mobile phase solvent(s).

5. The method of claim 1, wherein said aqueous buffer comprises ammonium phosphate (($NH_4$)$H_2PO_4$).

6. The method of claim 1, wherein analyzing the sample comprises detecting and quantifying the presence of ≤1.0% w/w beta-Asp10 of the total peptide content.

7. The method of any one of the preceding claims, wherein the sample containing abaloparatide is a formulated abaloparatide drug product.

8. The method of claim 7, wherein the sample containing abaloparatide is initially prepared, has been stored for up to 23 months at 2-8° C., has been stored for 23 months at 2-8° C. followed by a month at 20-25° C., or has been stored for 35 months at 2-8° C. followed by a month at 20-25° C.

9. A method of establishing the suitability of a formulated abaloparatide drug product for administration to a subject, the method comprising:
detecting and quantifying the presence of ≤5% w/w beta-Asp10 of the total peptide content in a formulated abaloparatide drug product using an HPLC and/or UPLC using a binary solvent system with a mobile phase comprising an aqueous buffer, wherein said aqueous buffer has a pH range of between 7.5-8.5 prior to mixing with any additional mobile phase solvent.

10. The method of claim 9, wherein the formulated abaloparatide drug product is an initially prepared, formulated abaloparatide drug product.

11. The method of claim 9, wherein the formulated abaloparatide drug product has been stored for 23 months at refrigerated conditions, followed by one month at room temperature.

12. The method of claim 9, wherein the formulated abaloparatide drug product has been stored for 35 months at refrigerated conditions, followed by one month at room temperature.

13. The method of any one of claims 9-12, comprising using a C4 Silicon-based, reverse phase column comprising particles with an average mean particle diameter of less than 3.0 microns.

14. A formulated abaloparatide drug product comprising ≤5% w/w beta-Asp10 of the total peptide content, and an aqueous buffer having a pH from 4.5-5.5, wherein said formulated abaloparatide drug product has an abaloparatide concentration of between 1.8 mg/mL and 2.2 mg/mL, wherein the suitability of the formulated abaloparatide drug product for administration to a subject has been established by a method comprising: detecting and quantifying the presence of ≤5% w/w beta-Asp10 of the total peptide content in the formulated abaloparatide drug product.

15. The formulated abaloparatide drug product of claim 14, comprising ≤1.0% w/w beta-Asp10 of the total peptide content.

* * * * *